United States Patent
Chang et al.

(10) Patent No.: US 11,504,394 B2
(45) Date of Patent: Nov. 22, 2022

(54) TARGETED IONOPHORE-BASED METAL DELIVERY

(71) Applicant: The Regents of the University of California, Oakland, CA (US)

(72) Inventors: Christopher J. Chang, Berkeley, CA (US); Timothy Su, Berkeley, CA (US); Marie Heffern, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 355 days.

(21) Appl. No.: 16/594,798

(22) Filed: Oct. 7, 2019

(65) Prior Publication Data

US 2020/0113937 A1  Apr. 16, 2020

Related U.S. Application Data

(60) Provisional application No. 62/744,840, filed on Oct. 12, 2018.

(51) Int. Cl.

| | |
|---|---|
| *A61K 33/34* | (2006.01) |
| *A61K 47/54* | (2017.01) |
| *A61K 47/64* | (2017.01) |
| *A61K 47/60* | (2017.01) |
| *A61P 1/16* | (2006.01) |
| *A61K 45/06* | (2006.01) |

(52) U.S. Cl.
CPC ............ *A61K 33/34* (2013.01); *A61K 47/545* (2017.08); *A61K 47/549* (2017.08); *A61K 47/60* (2017.08); *A61K 47/64* (2017.08); *A61P 1/16* (2018.01); *A61K 45/06* (2013.01)

(58) Field of Classification Search
CPC .................................................... A61K 33/34
See application file for complete search history.

(56) References Cited

PUBLICATIONS

Xie et al (Inorg Chem. Jun. 5, 2017;56(11):6429-6437). (Year: 2017).*
Su, et al.; "A Modular Ionophore Platform for Liver-Directed Copper Supplementation in Cells and Animals"; J. Am. Chern. Soc.; vol. 140, No. 42, pp. 13764-13774 (Oct. 24, 2018).

* cited by examiner

*Primary Examiner* — Benjamin J Packard
(74) *Attorney, Agent, or Firm* — Bozicevic Field & Francis, LLP; Paula A. Borden; Rudy J. Ng

(57) ABSTRACT

The present disclosure provides ionophore compounds, which are useful for facilitating delivery of a metal ion to a cell, tissue or organ of interest. The present disclosure provides compositions comprising the subject ionophore compounds. The present disclosure provides methods of delivering a metal ion intracellularly to a target cell. The present disclosure also provides methods of treating a condition associated with a metal deficiency in an individual.

21 Claims, 49 Drawing Sheets

TARGETED IONOPHORE-BASED METAL DELIVERY

CROSS-REFERENCE

This application claims the benefit of U.S. Provisional Patent Application No. 62/744,840, filed Oct. 12, 2018, which application is incorporated herein by reference in its entirety.

STATEMENT REGARDING FEDERALLY SPONSORED RESEARCH

This invention was made with government support under Grant Nos. GM079465 and GM122248 awarded by the National Institutes of Health. The government has certain rights in the invention.

INTRODUCTION

Metal deficiency is implicated in a variety of genetic, neurological, cardiovascular, and metabolic diseases. Current approaches for addressing metal deficiency rely on generic metal ion supplementation, which can potentially lead to detrimental off-target metal accumulation in unwanted tissues and subsequently trigger oxidative stress and damage cascades.

Copper is a required nutrient for all living organism, enabling fundamental life processes spanning respiration, antioxidant defense, neurotransmitter synthesis, metabolism, and cell signaling. Biological copper deficiency hinders these essential functions and correlates with various pathologies including Menkes disease, familial amyotrophic lateral sclerosis, neurodegenerative disorders, cardiovascular disease, and metabolic disorders.

SUMMARY

The present disclosure provides ionophore compounds, which are useful for facilitating delivery of a metal ion to a cell, tissue or organ of interest. The present disclosure provides compositions comprising the subject ionophore compounds. The present disclosure provides methods of delivering a metal ion intracellularly to a target cell. The present disclosure also provides methods of treating a condition associated with a metal deficiency in an individual.

BRIEF DESCRIPTION OF THE DRAWINGS

The invention is best understood from the following detailed description when read in conjunction with the accompanying figures. The patent or application file contains at least one figure executed in color. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

DEFINITIONS

Figure 1A:
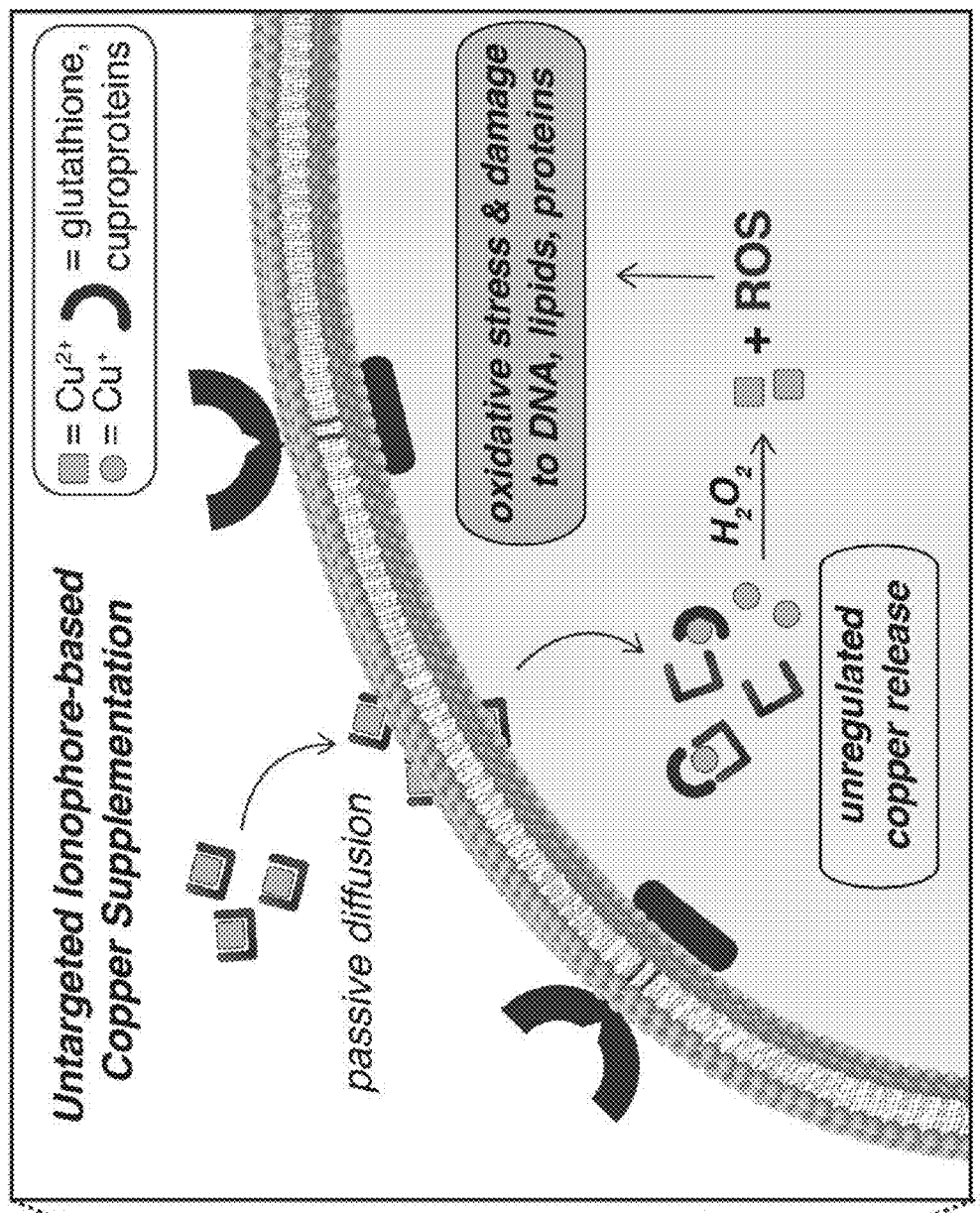
FIG. 1A shows that conventional ionophores increase copper levels in many organs due to the non-specific nature of passive diffusion.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Substituted alkylene" refers to an alkylene group having from 1 to 3 hydrogens replaced with substituents as described for carbons in the definition of "substituted" below.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated C$_3$-C$_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, C$_1$-C$_8$ alkoxy, C$_1$-C$_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" or "azide" refers to the group —N$_3$.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, $NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)^2R^{70}$, —$S(O)^2O^-M^+$, —$S(O)^2OR^{70}$, —$OS(O)^2R^{70}$, —$OS(O)^2O^-M^+$, —$OS(O)^2OR^{70}$, —$P(O)(O^-)^2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

By the term "functional groups" is meant chemical groups such as halo, hydroxyl, sulfhydryl, C1-C24 alkoxy, C2-C24 alkenyloxy, C2-C24 alkynyloxy, C5-C20 acyloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—$NH_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N+≡C—), cyanato (—O—C≡N), isocyanato (—O—N+≡C—), isothiocyanato (—S—C≡N), azido (—N═N+═N—), formyl (—(CO)—H), thioformyl (—(CS)—H), amino (—NH$_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR═NH where R=hydrogen, C1-C24 alkyl, C5-C20 aryl, C6-C20 alkaryl, C6-C20 aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), epidithio (—S—S—), carbonyldioxy (—O—CO—O—), alkyldioxy (—O—(CH2)n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$)alkyl), which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

As used herein, the term "hydrophilic group" by itself refers to a monovalent or multivalent group which includes a hydrophilic moiety and an optional linker. In some cases, a hydrophilic group is attached to the hydrophilic masking moiety and the hydrophilic tail moiety of the subject endosomal disruptors. The hydrophilic moiety is a moiety that is well solvated in aqueous environments, e.g., under reverse phase (RP) chromatography conditions, and that imparts increased water solubility on the group to which it is attached or incorporated (e.g., the linker). In some cases, the hydrophilic moiety is referred to as a hydrophilic functional group. In some cases, the hydrophilic moiety is a heterocycle. In certain cases, the hydrophilic moiety is a heteroaryl. In some cases, the hydrophilic moiety is charged (e.g., ionic). In some cases, the hydrophilic moiety is polar and neutral (e.g., non-ionic). It is understood that certain functional groups may be present in either an ionic or a non-ionic form, dependent on the surrounding conditions, e.g., solvent, pH and the like, and that all such forms of the hydrophilic moieties described herein are meant to be included in the present disclosure. For example, the hydrophilic moiety can be a basic group which is neutral until protonated, e.g., under aqueous conditions of a suitable pH, or the hydrophilic moiety can be an acidic group which is neutral until deprotonated, e.g., under aqueous conditions of a suitable pH.

A hydrophilic moiety can increase the solubility of the group to which it is attached in a predominantly aqueous solution, as compared to a control group which lacks the hydrophilic moiety. A hydrophilic moiety is different from a hydrophobic moiety which is not well solvated in aqueous environments. In certain instances, a hydrophilic group includes at least one neutral polar functional group per 5 carbons, or at least one charged functional group per 7 carbons. In some instances, a hydrophilic group (e.g., the hydrophilic group in isolated form as a discrete molecule) has solubility in water of at least 1% by weight.

Hydrophilic groups and hydrophilic moieties of interest include, but are not limited to, Nitrogen-containing heterocycle, amide, carbamate, carboxylic acid carboxy ester, methyl ether, cyano, amine, sulfonamide, sulfonate, urea, thiourea, sulfonic acid, carboxylate, phosphonate, phosphate, sulfate, sulfinate, sulfonium, polyethylene glycols (PEG) and modified PEGs, hydroxyl, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO3M', —PO3M', —NR3+, Y', (CH2CH2O)pR and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH2CH2O) yyCH2CH2XRyy, —(CH2CH2O) yyCH2CH2X—, —X(CH2CH2O) yyCH2CH2-, glycol, and polyethylene glycol, wherein yy is selected from 1 to 1000, X is selected from O, S, and NRZZ, and RZZ and RYY are independently selected from H and C1-3 alkyl. In some cases, a hydrophilic moiety is (CH2)x(OCH2CH2)yOCH3 where each x is independently an integer from 0-20, each y is independently an integer from 0 to 50.

Nitrogen-containing heterocycles of interest that find use as hydrophilic moieties include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, and substituted versions thereof.

As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a functional group (e.g., as described herein). Any convenient linking groups may be utilized at the terminal of a PEG to connect the group to a moiety of interest including but not limited to, alkyl, aryl, hydroxyl, amino, acyl, acyloxy, carboxyl ester and amido terminal and/or substituent groups.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be metabolized into a pharmaceutically active derivative.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes lipoproteins, glycoproteins, and the like.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ionophore" includes a plurality of such ionophores and reference to "the targeting moiety" includes reference to one or more targeting moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions of other terms and concepts appear throughout the detailed description below.

DETAILED DESCRIPTION

The present disclosure provides ionophore compounds, which are useful for facilitating delivery of a metal ion to a cell, tissue or organ of interest. The present disclosure provides compositions comprising the subject ionophore compounds. The present disclosure provides methods of delivering a metal ion intracellularly to a target cell. The present disclosure also provides methods of treating a condition associated with a metal deficiency in an individual.

Ionophore Compounds

The present disclosure provides ionophore compounds which are useful for facilitating delivery of a metal ion to a cell, tissue or organ of interest. An ionophore compound of the present disclosure includes one or more targeting moieties, an ionophore capable of complexing a metal ion and one or more linkers between the target moiety and the ionophore. In certain cases, the targeting moiety recognizes a specific cell surface receptor localized to cells or tissues of interest. The targeting moiety-cell surface receptor recognition triggers endocytosis and internalization of the ionophore complex. The ionophore complex comprises a metal ion and is capable of releasing the metal ion in the endolysosomal pathway through either intracellular reduction or degradation. In certain cases, the ionophore is complexed to a metal ion in a first oxidation state and releases a metal ion in a second oxidation state. The released metal ion is capable of binding to metal storage or trafficking proteins, which can then utilize the metal as needed. It is understood that any convenient ionophore capable of complexing a metal ion and releasing a metal ion intracellularly can be utilized in the subject ionophore compounds. It will also be understood that any convenient targeting moiety capable of recognizing a specific cell surface receptor localized to cells or tissues of interest can be utilized in the subject ionophore compounds. Without being bound to any particular theory, the targeting moiety should be large or hydrophilic enough to hinder passive diffusion such that metal release is receptor-mediated. Accordingly, the subject ionophore compound pair metal-delivering ionophores with targeting moieties that recognize specific cell surface receptors localized to cells and tissues of interest, thus providing a versatile approach to site-specific metal ion delivery In some cases, the subject ionophore compound of the formula (I):

wherein:
T is a targeting moiety (e.g., a cell targeting moiety, a tissue targeting moiety or an organ targeting moiety);
L is a linker;
M is a metal ion;
Z is an ionophore capable of complexing M; and
n is an integer from 1 to 20 (e.g., 1 to 10, 1 to 6, 1 to 3 or 1 to 2).

According to certain embodiments, an ionophore compound of the present disclosure includes a targeting moiety. The targeting moiety may vary and may be selected based, e.g., on the nature of the cell surface molecule on the target cell. Targeting moieties that may be employed include cell targeting moieties, tissue targeting moieties or organ targeting moieties. In certain cases, the targeting moiety is selected from a liver-targeting moiety, a mitochondria-targeting moiety, a nucleus-targeting moiety, an adipose-targeting moiety, a heart-targeting moiety and a brain targeting moiety. It will be understood that any convenient targeting group that generates site-specific delivery of a metal ion may be used in the present ionophore compounds. Non-limiting examples of targeting moieties of the subject ionophore compounds include, saccharides, polysaccharides, multivalent saccharides, amino sugars, peptides, small molecule drugs, small molecule drug fragments and phosphonium cations.

In certain aspects, the targeting moiety specifically binds to the cell surface molecule. As used herein, a targeting moiety that "specifically binds to the cell surface molecule" or is "specific for the cell surface molecule" refers to a targeting moiety that binds the cell surface molecule with greater affinity than with other cell surface molecules. In some cases, the targeting moiety has specific affinity for a molecule on the surface of a target cell, wherein the targeting agent of the subject compound binds to the target cell and subsequently are internalized into the target cell.

According to certain embodiments, the targeting moiety exhibits a binding affinity to the cell surface molecule of a $K_d$ of less than or equal to about $10^{-5}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis, surface plasmon resonance (SPR) technology (e.g., the BIAcore 2000 instrument, using general procedures outlined by the manufacturer), radioimmunoassay, or by another method.

In certain embodiments, the targeting moiety is a small molecule. By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain cases, the small molecule is not made of repeating molecular units such as are present in a polymer. In certain cases, the target cell surface molecule is a receptor for which the targeting moiety is a small molecule, and the small molecule of the ionophore compound is the small molecule ligand (or a derivative thereof) of the receptor. Small molecules that find use in targeting a ionophore compound to a target cell or specific tissue of interest may be known. See, e.g., Alsaggar et al. (2018) J. Drug Target 26, 385. As just one example, N-acetylgalactosamine (GalNAc) derivatives have been shown to effectively bind to the asialoglycoprotein receptor (ASPGR), which is specifically expressed in the liver at high levels. See e.g., Mamidyala et al. (2012) J. Am. Chem. Soc. 134, 1978; and D'Souza et al. (2015), J. Control. Release 203, 126. In certain cases, an ionophore compound of the present disclosure includes a small molecule as the targeting moiety, in which it has been demonstrated in the context of a small molecule drug conjugate (SMDC) that the small molecule is effective at targeting a conjugate to a target cell of interest by binding to a cell surface molecule on the target cell.

In some cases, the targeting moiety is a protein or peptide, such as an antibody, or active binding fragment thereof. In some instances, delivery of the subject compounds can be achieved by attaching antibodies specific to cardiac, vascular, endothelial, or matrix proteins to the molecule. Cardiac proteins useful for targeting the heart include, for example, cardiac specific proteins such as myosin, troponin, and light chain myosin. The cell-targeting agent can be an aptamer.

In some cases, the targeting moiety is a saccharide. In some cases, the targeting moiety is a polysaccharide. In some cases, the targeting moiety is a multivalent saccharide. In some cases, the targeting moiety is an amino sugar. A multivalent saccharide is a targeting moiety that includes two or more targeting saccharide moieties. In some cases, the multivalent saccharide may include two or more different saccharides, such that the multivalent saccharide is capable of targeting two or more different cells or tissues. In some cases, the multivalent saccharide may include two or more of the same saccharide, such that the multivalent saccharide is a cell-specific or tissue-specific targeting moiety.

In some cases, the target is a cell carbohydrate receptor. Cell carbohydrate receptors of interest that may be targeted according to the present disclosure is selected from a hepatocyte asialoglycoprotein receptor, a Kupffer cell mannose receptor, and a liver endothelial cell mannose receptor.

In some cases, the targeting moiety is a cell targeting agent selected from asialoglycoprotein, galactose and mannose. In some embodiments, the targeting moiety is galactose, a galactose derivative or a multivalent galactose conjugate. In some cases, the targeting moiety is an amino sugar derivative of galactose or a multivalent amino sugar derivative of galactose.

In certain cases, the targeting moiety is an amino sugar derivative of galactose described by the structure:

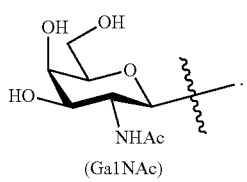
(GalNAc)

In certain cases, the targeting moiety is a multivalent GalNAc conjugate (i.e. contains more than one GalNAc moiety).

In some cases, a mannoside can be incorporated into the subject compounds to preferentially target macrophages and attain enhanced cellular uptake both in vitro and in vivo with better in vitro/in vivo correlation than for control compounds. Mannosylation can be achieved by the incorporation of agent such as an alkyl mannoside, cholesten-5-yloxy-N-(4-((1-imino-2-α-thioglycosylethyl)amino)butyl) formamide (Mann-C4-Chol), Mann-His-C4-Chol, Man2DOG, 4-aminophenyl-a-D-mannopyranoside, and manntriose (Man3)-DPPE into the subject compound.

In some cases, the targeting moiety is a peptide. Cell targeting peptides (CTPs) and cell penetrating peptides (CPPs) can be linked to the ionophore compound to provide cell-specific targeting. As just one example, peptide sequences such as CKGGRAKDC (SEQ ID NO:1) have been shown to selectively associate with adipose tissue. In another example, peptide sequences such as APWHLSSQYSRT (SEQ ID NO:2) have been shown to selectively associate with the heart. In yet another example, peptide sequences such as TFFYGGSRGKRNNFKTEEY (SEQ ID NO:3) have been shown to selectively associate with the brain. For example, peptide sequences such as GGPNLTGRW (GGP-peptide) (SEQ ID NO: 4) have been shown to selectively associate with neutrophils and monocytes.

In some cases, the targeting moiety is a small molecule drug. In some cases, the targeting moiety is a small molecule drug fragment.

In some cases, the targeting moiety is a nucleus targeting small molecule described by the structure:

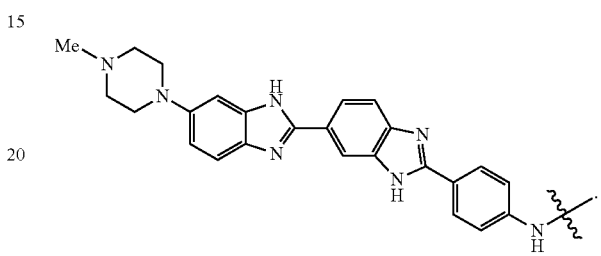

In some cases, the targeting moiety is a heart targeting small molecule described by the structure:

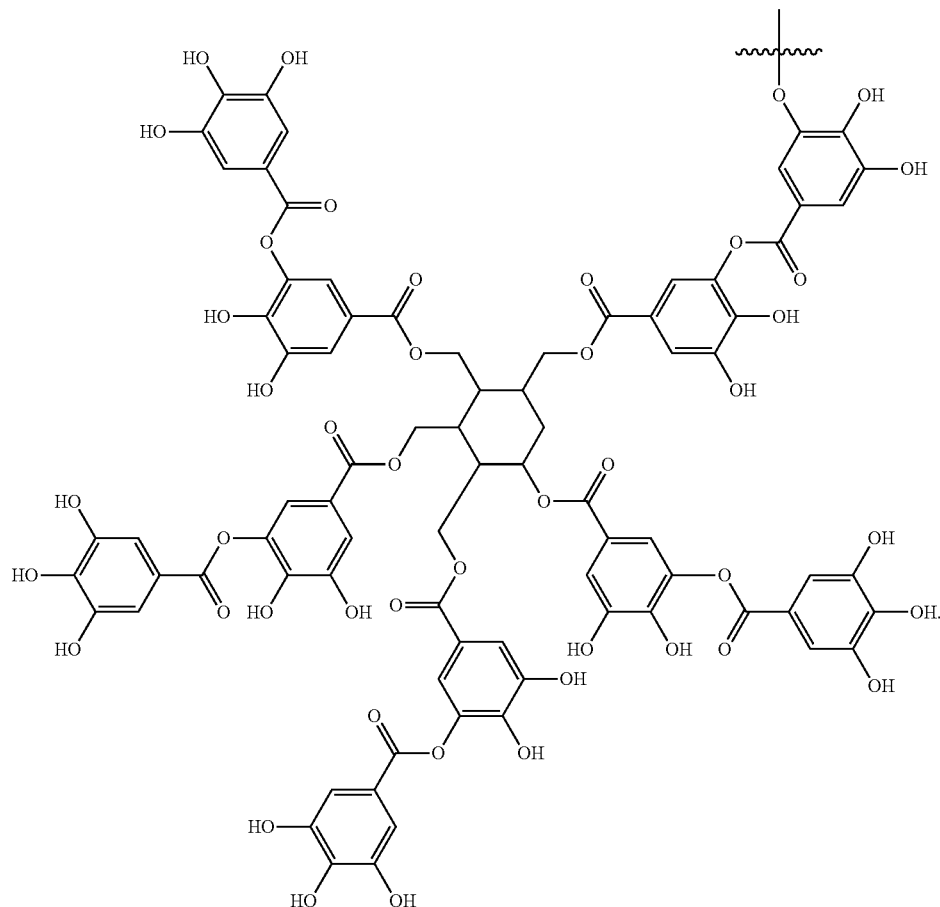 [SMILES: *Oc1cc(C(=O)Oc2cc(C(=O)OCC3CC(OC(=O)c4cc(O)c(O)c(OC(=O)c5cc(O)c(O)c(O)c5)c4)C(COC(=O)c4cc(O)c(O)c(OC(=O)c5cc(O)c(O)c(O)c5)c4)C(COC(=O)c4cc(O)c(O)c(OC(=O)c5cc(O)c(O)c(O)c5)c4)C3COC(=O)c3cc(O)c(O)c(OC(=O)c4cc(O)c(O)c(O)c4)c3)cc(O)c2O)cc(O)c1O]

In certain cases, the targeting moiety is an adipose targeting small molecule described by the structure:

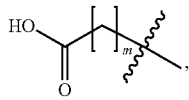

wherein m is an integer from 1 to 20.

In other cases, the targeting moiety is a phosphonium cation. In certain cases, the phosphonium cation is mitochondria targeting moiety described by the structure:

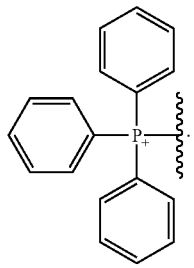

According to certain embodiments, an ionophore compound of the present disclosure includes an ionophore capable of complexing a metal ion. Any of the metal-binding agents and chelators described herein can be used according to the present disclosure, as well as any other chelator not mentioned. The term "ionophore" refers to molecules capable of selectively forming a complex with a metal ion. The word selectively in this context indicates that the ionophore favors formation of a complex with a target ion to the substantial exclusion of forming complexes with other ions. An ionophore is a molecule that delivers and releases a metal ion into, e.g., cells rather than sequester and remove metals from cells as can occur with a metal ion chelator. The ionophores should bind the target ion tightly and specifically, such that the ionophore does not release the ion until it reaches its specific target intracellular destination whereby it may be released by intracellular reduction or degradation. In certain cases, the subject ionophores are selective for classes of ions. For example, certain ionophores will preferentially form complexes with divalent ions to the exclusion of monovalent. In certain other cases, the ionophores will preferentially form complexes with trivalent ions to the exclusion of divalent ions. The term ion will be understood to represent either an individual ion or a class of ions, such as transition metal ions, divalent ions, trivalent ions, or some other grouping of ions. In certain cases, the subject ionophores selectively form complexes with a copper, iron, zinc, cobalt or manganese ions. In certain cases, the subject ionophores selectively form complexes with a first ionic form of a metal ion and release a second ionic form of the metal ion intracellularly. It will be understood that any convenient ionophore capable of complexing a metal ion selected from copper, iron, zinc, cobalt or manganese may find use in the present ionophore compounds.

Copper ionophores include, but are not limited to, copper complexes with histidine, bisthiosemicarbazones, 8-hydroxyquinolines, and others. In some cases, the ionophore can chelate copper in the $Cu^{2+}$ +2 oxidation state, until contact with a reducing intracellular environment sufficient to act as a redox trigger for reduction of the metal complex and subsequent release of $Cu^+$ in the +1 oxidation state to provide for copper-binding molecules and proteins (FIG. 1A).

In certain cases, the ionophore complexes $Cu^{2+}$ and has decreased affinity for $Cu^+$. In certain cases, the ionophore is capable of complexing $Cu^{2+}$ ($K_d$ approximately $10^{-18}M^{-1}$) much more tightly than $Cu^+$ ($K_d$ approximately $10^{-13}M^{-1}$). In some cases, the ionophore complexes $Cu^{2+}$ and releases $Cu^+$ upon reduction in the intracellular medium. In certain other cases, the ionophore complexes $Fe^{3+}$ and has decreased affinity for $Fe^{2+}$, such that the ionophore complexes $Fe^{3+}$ and releases $Fe^{2+}$ upon reduction in the intracellular medium.

Any convenient iron chelating agents can be adapted for use as an iron carrying ionophores of the subject compounds. Iron ionophores may be classified into bidentate, tridentate or hexadentate chelators. Iron ions can have six electrochemical coordination sites. Such chelators are termed "hexidentate", of which desferrioxamine is an example. Specific bidentate iron ionophores include, but are not limited to, 1,2-dimethyl-3-hydroxypyridin-4-one (Deferiprone, DFP or Ferriprox) and 2-deoxy-2-(N-carbamoylmethyl-[N'-2'-methyl-3 '-hydroxypyridin-4'-one])-D-glucopyranose (Feralex-G).

Specific tridentate iron-binding ionophores comprise pyridoxal isonicotinyl hydrazone (PIH), 4,5-dihydro-2-(2,4-dihydroxyphenyl)-4-methylthiazole-4-carboxylic acid (GT56-252), 4,5-dihydro-2-(3'-hydroxypyridin-2'-yl)-4-methylthiazole-4-carboxylic acid (desferrithiocin or DFT) and 4-[3,5-bis(2-hydroxyphenyl)-[1,2,4-]triazol-1-yl]benzoic acid (deferasirox). Substituted 3,5-diphenyl-1,2,4-triazoles, e.g., 4-[3,5-bis(2-hydroxyphenyl)-[1,2,4]triazol-1-yl]benzoic acid (deferasirox), their process of manufacture and use thereof are disclosed in the international patent application WO 97/49395. An advantageous pharmaceutical preparation of such compounds in the form of dispersible tablets is disclosed in the international patent application WO 2004/035026.

Specific hexadentate iron-binding ionophores comprise N,N'-bis(o-hydroxybenzyl) ethylenediamine-N,N'-diacetic acid (HBED), N-(5-C3-L (5-aminopentyl)hydroxycarbamoyl)-propionamido)pentyl)-3(5-(N-hydroxyacetoamido)-pentyl)carbamoyl)-proprionhydroxamic acid (deferoxamine, desferoxamine or DFO) and hydroxymethyl-starch-bound deferoxamine (S-DFO). Further derivatives of DFO include aliphatic, aromatic, succinic and methylsulphonic analogs of DFO and specifically, sulfonamide-deferoxamine, acetamide-deferoxamine, propylamide deferoxamine, butylamide-deferoxamine, benzoylamide-deferoxamine, succinamide-derferoxamine and methylsulfonamide-deferoxamine.

A further class of iron-binding ionophores is the biomimetic class, such as those described by Meijler et al. (Meijler et al., 2002, J. Am. Chem. Soc., 124, 12666-12667). Certain substituted 3,5-diphenyl-1,2,4-triazoles also have valuable pharmacological properties for iron chelation (Bergeron et al., 1991, J. Med. Chem., 34, 2072-2078). Other iron chelators which can be used according to the invention are polyanionic amines, substituted polyaza compounds and desferrithiocon.

One class of iron-binding ionophores includes the exochelins. The use of exochelins and exochelin variants to chelate free iron is described in detail in U.S. Pat. No. 5,721,209. Proteins that bind iron are also known to those of skill in the art. Such proteins include, but are not limited to ferritin, hemoglobin, and the like.

In some cases, the iron ionophore is selected from deferiprone, deferoxamine, deferasirox, polyanionic amines, substituted polyaza compounds, desferrithiocon, hydroxybenzyl-ethylenediamine-diacetic acid, pyridoxal isonicotinoyl hydrazine, ferrichrome, PBT434, PIH (pyridoxal isonicotinoyl hydrazone), rhodotorulic acid, HBED (N,N'-Bis(2-hydroxybenzyl)ethylenediamine-N,N-diacetic acid), HBPD (N,N'-Bis(2-hydroxybenzyl)propylene-1,3-diamine-N,N-diacetic acid), 2,3-dihydroxybebzoic acid, DTPA (diethyltriamine pentaacetic acid), 5-chloro-7-iodo-8-hydroxyquinoline (clioquinol), pseudan, iron chelators produced by bacterial siderophores, and derivatives thereof.

In certain embodiments, the ionophore capable of complexing a metal ion is selected from:

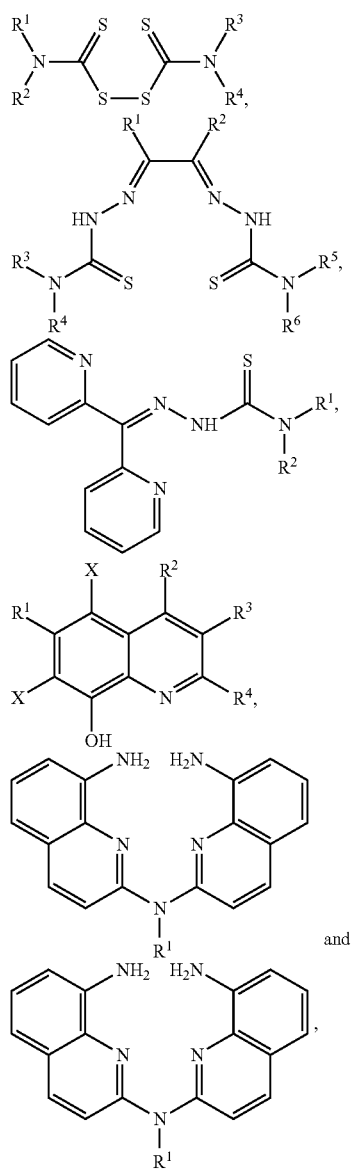

and wherein:
X is a halogen; and
$R^1$, $R^2$, $R^3$, $R^4$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl and substituted acyl.

In some cases, the ionophore capable of complexing a metal ion is described by the structure:

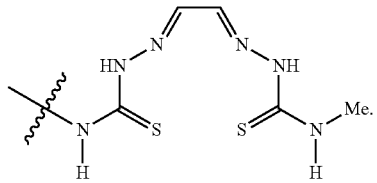 [SMILES: *NC(=S)N/N=C/C=N/NC(=S)NC]

According to certain embodiments, an ionophore compound of the present disclosure includes one or more linkers between the target moiety and the ionophore. In certain cases, linker is selected from a linear or branched alkyl, alkenylene, alkynylene, arylene, alkarylene, aralkylene, alkoxy, alkamine, polyethylene glycol (PEG), a modified PEG, an oligoethyleneglycol, a phosphate, a phosphonate, a boric acid, a carboxylate, a sulfate, a sulfonate, an amine, a glycerol, a sugar, an amino acid and a substituted amino acid.

In certain instances, the linker includes a $C_1$-$C_{20}$ alkyl group, such as an alkyl group comprising 2, 3, 4, 5, 6, 7, 8, 9, 10, 11, 12, 13, 14, 15, 16, 17, 18, 19 or 20 carbon atoms. In certain instances, the linker is a $C_1$-$C_{20}$ alkyl group such as an alkyl group comprising 2, 3, 4, 5, 6, 7, 8, 9 or 10 carbon atoms. In certain cases, the linker includes a group selected from, ethyl, propyl, butyl, pentyl, hexyl, pentyl and octyl.

In certain embodiments, the ionophore compound of the present disclosure includes a hydrophilic linker group. In certain cases, the hydrophilic linker group is selected from polyethylene glycol (PEG), modified PEG and a oligoethyleneglycol. In some cases, the hydrophilic linker includes a PEG moiety. In certain instances, the linker includes more than 1 PEG unit, such as 2, 3, 4, 5, 6, 7, 8, 9 or 10 PEG units. In certain instances, the linker includes less than 10 PEG units, such as 9, 8, 7, 6, 5, 4, 3, 2 or 1 PEG unit. In certain cases, the linker includes a group composed of 3 PEG units. In certain cases, the hydrophilic linker group is a triethylene glycol chain.

In certain embodiments of formula (I), the structure of the ionophore compound has the formula (II)

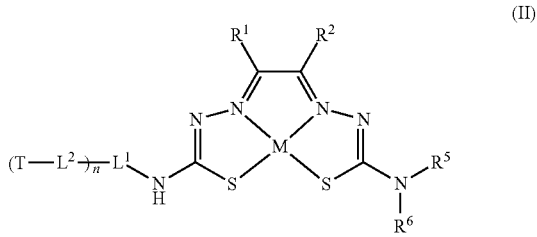

(II)

wherein:
$R^1$, $R^2$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl, substituted acyl and -$L^1(L^2$-$T)_n$;
T is a targeting moiety;
$L^1$ is a bond or a linker;
$L^2$ are each independently a linker selected from a linear or branched alkyl, alkenylene, alkynylene, arylene, alkarylene, aralkylene, alkoxy, alkamine polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid and a substituted amino acid;

M is a metal ion; and n is an integer from 1 to 20.

In certain embodiments of formula (II), $R^1$, $R^2$, $R^5$ and $R^6$ are each H. In certain cases of formula (II), $R^1$, $R^2$ and $R^6$ are each H and $R^5$ is an alkyl group or a substituted alkyl group. In certain cases, $R^5$ is an alkyl group. In certain cases, $R^5$ is a methyl group.

In certain embodiments of formula (II), one or more of $R^1$, $R^2$, $R^5$ and $R^6$ are described by the formula -$L^1(L^2$-$T)_n$, such that more than one targeting moiety is linked to the ionophore core. In certain cases, $R^1$ is described by the formula -$L^1(L^2$-$T)_n$. In certain cases, $R^2$ is described by the formula -$L^1(L^2$-$T)_n$. In certain cases, $R^5$ is described by the formula -$L^1(L^2$-$T)_n$. In certain cases, $R^6$ is described by the formula -$L^1(L^2$-$T)_n$. In certain cases, at least two of $R^1$, $R^2$, $R^5$ and $R^6$ are described by the formula -$L^1(L^2$-$T)_n$. In certain cases, one of $R^1$, $R^2$, $R^5$ and $R^6$ is described by the formula -$L^1(L^2$-$T)_n$. In certain other cases, at least three of $R^1$, $R^2$, $R^5$ and $R^6$ are described by the formula -$L^1(L^2$-$T)_n$. In yet other cases, all of $R^1$, $R^2$, $R^5$ and $R^6$ are described by the formula -$L^1(L^2$-$T)_n$.

In certain embodiments of formula (II), one or more of $R^1$, $R^2$, $R^5$ and $R^6$ is an aryl or a substituted aryl group. In certain cases, $R^1$ is an aryl or a substituted aryl group. In certain cases, $R^2$ is an aryl or a substituted aryl group. In certain cases, $R^5$ is an aryl or a substituted aryl group. In certain cases, $R^6$ is an aryl or a substituted aryl group. In certain cases, at least two of $R^1$, $R^2$, $R^5$ and $R^6$ are aryl or a substituted aryl groups. In certain cases, one of $R^1$, $R^2$, $R^5$ and $R^6$ is an aryl or a substituted aryl group. In certain other cases, at least three of $R^1$, $R^2$, $R^5$ and $R^6$ are aryl or a substituted aryl groups. In yet other cases, all of $R^1$, $R^2$, $R^5$ and $R^6$ are aryl or substituted aryl groups.

In certain embodiments of formula (II), one or more of $R^1$, $R^2$, $R^5$ and $R^6$ is an alkoxy or a substituted alkoxy group. In certain cases, $R^1$ is an alkoxy or a substituted alkoxy group. In certain cases, $R^2$ is an alkoxy or a substituted alkoxy group. In certain cases, $R^5$ is an alkoxy or a substituted alkoxy group. In certain cases, $R^6$ is an alkoxy or a substituted alkoxy group. In certain cases, at least two of $R^1$, $R^2$, $R^5$ and $R^6$ are alkoxy or a substituted alkoxy groups. In certain cases, one of $R^1$, $R^2$, $R^5$ and $R^6$ is an alkoxy or a substituted alkoxy group. In certain other cases, at least three of $R^1$, $R^2$, $R^5$ and $R^6$ are alkoxy or a substituted alkoxy groups. In yet other cases, all of $R^1$, $R^2$, $R^5$ and $R^6$ are alkoxy or substituted alkoxy groups.

In certain embodiments of formula (II), one or more of $R^1$, $R^2$, $R^5$ and $R^6$ is an acyl or a substituted acyl group. In certain cases, $R^1$ is an acyl or a substituted acyl group. In certain cases, $R^2$ is an acyl or a substituted acyl group. In certain cases, $R^5$ is an acyl or a substituted acyl group. In certain cases, $R^6$ is an acyl or a substituted acyl group. In certain cases, at least two of $R^1$, $R^2$, $R^5$ and $R^6$ are acyl or a substituted acyl groups. In certain cases, one of $R^1$, $R^2$, $R^5$ and $R^6$ is an acyl or a substituted acyl group. In certain other cases, at least three of $R^1$, $R^2$, $R^5$ and $R^6$ are acyl or a substituted acyl groups. In yet other cases, all of $R^1$, $R^2$, $R^5$ and $R^6$ are acyl or substituted acyl groups.

In certain embodiments of formula (II), the targeting moiety (T) is a cell targeting moiety, a tissue targeting moiety or an organ targeting moiety (e.g., as described herein). In certain cases, the targeting moiety (T) is selected from, a peptide comprising the sequence CKGGRAKDC, a peptide comprising the sequence APWHLSSQYSRT, a peptide comprising the sequence TFFYGGSRGKRNNFKTEEY,

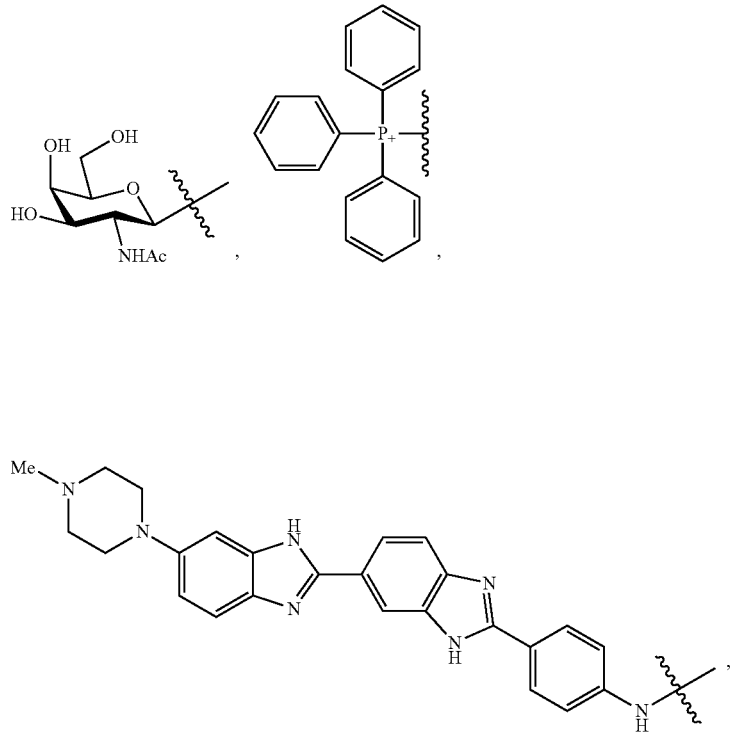

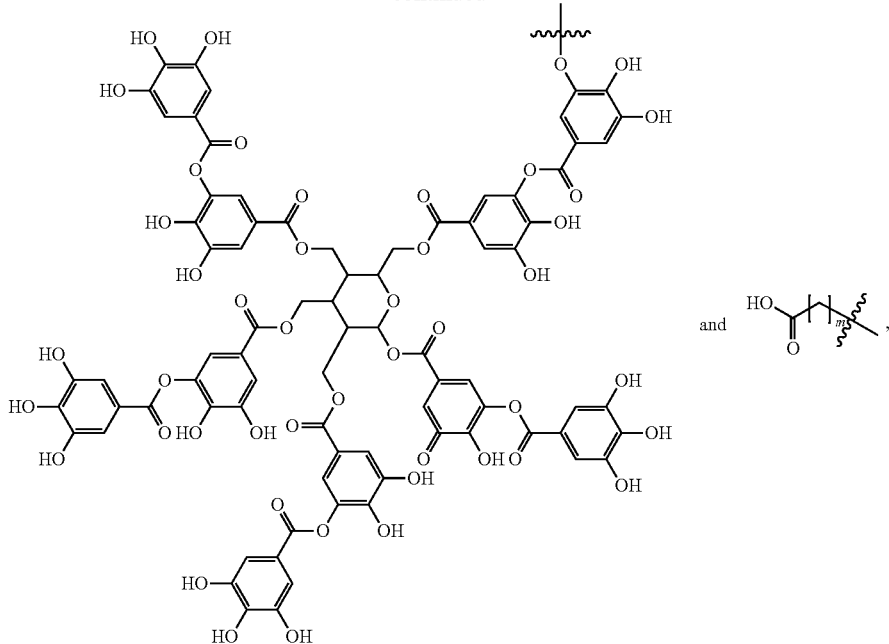

wherein m is an integer from 1 to 20.

In certain embodiments of formula (II), $L^1$ is a bond. In certain other embodiments, $L^1$ is a linker, e.g., as described herein. In certain embodiments, the linker $L^1$ is described by the linker $L^2$.

In certain embodiments of formula (II), $L^2$ is a linear or branched alkyl linker. In some embodiments, $L^2$ is a linear or branched alkenylene linker. In some embodiments, $L^2$ is a linear or branched alkynylene linker. In some embodiments, $L^2$ is a linear or branched arylene linker. In some embodiments, $L^2$ is a linear or branched alkarylene linker. In some embodiments, $L^2$ is a linear or branched aralkylene linker. In some embodiments, $L^2$ is a linear or branched alkoxy linker. In some embodiments, $L^2$ is a linear or branched alkamine linker. In some embodiments, $L^2$ is a linear or branched PEG linker. In some embodiments, $L^2$ is a linear or branched oligoethyleneglycol linker. In some embodiments, $L^2$ is a linear or branched glycerol linker. In some embodiments, $L^2$ is a linear or branched sugar linker. In some embodiments, $L^2$ is a linear or branched amino acid linker.

In some embodiments of formula (II), the linker $L^2$ is described by the structure:

wherein p and q are each independently an integer from 1 to 20. In certain instances, p is greater than 1, such as 2, 3, 4, 5, 6, 7, 8, 9, 10, 11, 12, 13, 14, 15, 16, 17, 18, 19 or 20. In certain instances, p is less than 10, such as 9, 8, 7, 6, 5, 4, 3, 2 or 1. In certain cases, p is 3. In certain instances, q is greater than 1, such as 2, 3, 4, 5, 6, 7, 8, 9, 10, 11, 12, 13, 14, 15, 16, 17, 18, 19 or 20. In certain instances, q is less than 10, such as 9, 8, 7, 6, 5, 4, 3, 2 or 1. In certain cases, q is 3.

In certain embodiments of formulae (I) or (II) the metal ion (M) is selected from a copper ion, an iron ion, a zinc ion, a cobalt ion and a manganese ion. In some cases, M is $Cu^{2+}$ and the ionophore has decreased affinity for $Cu^+$, such that the ionophore is capable of complexing $Cu^{2+}$. In certain other cases, M is $Fe^{3+}$ and the ionophore has decreased affinity for $Fe^{2+}$, such that the ionophore is capable of complexing $Fe^{3+}$.

In certain embodiments of formulae (I) or (II), the ionophore compound is described by the structure (Gal-Cu(gtsm):

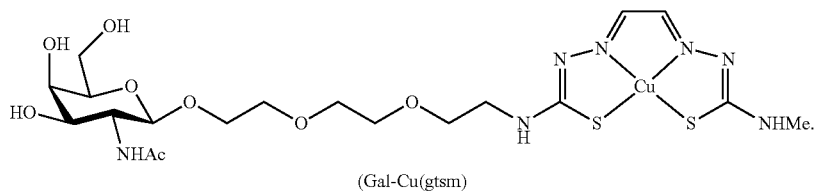

(Gal-Cu(gtsm))

Compositions

Also provided are pharmaceutical compositions comprising: a subject ionophore compound. Pharmaceutical compositions comprising: a subject ionophore together with one or more additional therapeutic agents are also provided. Also included is a pharmaceutically compatible excipient. The pharmaceutical composition may be a solution or suspensions of the ionophore compounds.

The herein-discussed ionophore compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

In some embodiments, the subject compound and an additional therapeutic agent, e.g. a small molecule, a chemotherapeutic, an antibody, an antibody fragment, an antibody-drug conjugate, an aptamer, or a protein, etc. are administered to individuals in a formulation (e.g., in the same or in separate formulations) with a pharmaceutically acceptable excipient(s). In some embodiments, the additional therapeutic agent is an agent to treat a disease or condition associated with the adipose tissue, heart, brain or liver.

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional active agents of interest. Any convenient active agents can be utilized in the subject methods in conjunction with the subject compounds. In some instances, the additional agent is a therapeutic agent to treat a disease associated with the adipose tissue, heart, brain or liver. The subject compound and therapeutic agent, as well as additional therapeutic agents for combination therapies, can be administered orally, subcutaneously, intramuscularly, intranasally, parenterally, or other route. The subject compound and second therapeutic agent (if present) may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ. In certain cases, the therapeutic agents can be administered intranasally. In some cases, the therapeutic agents can be administered intratumorally.

In some embodiments, the subject compound and a chemotherapeutic agent are administered to individuals in a formulation (e.g., in the same or in separate formulations) with a pharmaceutically acceptable excipient(s). The chemotherapeutic agents include, but are not limited to alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

The subject compound and second chemotherapeutic agent, as well as additional therapeutic agents as described herein for combination therapies, can be administered orally, subcutaneously, intramuscularly, parenterally, or other route. The subject compound and second chemotherapeutic agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Methods of Delivery

As summarized above, aspects of the present disclosure include methods of delivering a metal ion intracellularly to a target cell. The inventors discovered that the subject ionophore compounds (e.g., which pair metal-delivering ionophores with targeting moieties that recognize specific cell surface receptors localized to cells and tissues of interest) can be used to facilitate selective delivery of a metal ion to the cell or tissue of interest in a non-toxic manner. The targeting moiety of the ionophore compound recognizes a specific cell surface receptor localized to a cell or tissue of interest and this recognition triggers endocytosis and internalization of the receptor-ionophore complex. The complex releases the metal in the endolysosomal pathway through either intracellular reduction or degradation, and the released metal ion binds to metal storage or trafficking proteins, which can then utilize the metal as needed.

In some cases, the method includes: contacting a sample comprising a target cell with a composition comprising a subject ionophore compound that includes a targeting moiety (e.g., as described herein) to deliver intracellularly the metal ion of interest to the target cell. When the method is performed in vivo, the method can be a method of treatment, e.g., as described herein. In some cases, the method can be performed in vitro.

According, in one embodiment there is provided a method of delivering a metal ($M^2$) intracellularly to a target cell, the method comprising: contacting the target cell with a subject ionophore compound (e.g., as described herein); wherein: M is a first ionic from of the metal ion ($M^1$), wherein the ionophore has a higher affinity for $M^1$ over a second ionic from $M^2$; and T is a targeting moiety for the target cell; to internalize the ionophore within the target cell and reduce $M^1$ to $M^2$ thereby intracellularly releasing the metal ion ($M^2$) from the ionophore.

Any convenient cells can be targeted for intracellular delivery of a metal ion via the subject compounds (e.g., as described herein). Cells of interest include, but are not limited to, myeloid cells (such as dendritic cells, monocytes, macrophages and microglia).

The subject methods can provide for an increase in free metal ion in a target cell as compared to a control, i.e., a comparable cell (such as a clone, cell from the same tissue, etc.) not contacted with the composition. As such, the method can further include assessing a level of metal ion in the target cell via any convenient methods, e.g., using an intracellular metal ion indicator. Assessing can include quantitating the levels of free metal ion in the cell.

In certain embodiments, the target cells for use in the subject methods may include cells obtained from an in vitro source (e.g., a suspension of cells from laboratory cells grown in culture) or from an in vivo source (e.g., a vertebrate, an invertebrate, a mammalian subject, a human subject, etc.). In some embodiments, a target cell is obtained from an in vitro source. In vitro sources include, but are not limited to, environmental samples that contain eukaryotic (e.g., mammalian, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the target cell is obtained from an in vivo source which can include samples obtained from tissues (e.g., cell suspension from a tissue biopsy, cell suspension from a tissue sample, bone marrow etc.) and/or body fluids (e.g., whole blood, fractionated blood, plasma, serum, saliva, lymphatic fluid, interstitial fluid, etc.). In vivo sources include living multi-cellular organisms. In some instances, the target cell is obtained from a patient diagnosed as having a disease or condition. In some instances, the target cell may be obtained from a subject suspected of having a disease or condition. In some instances, the target cell is obtained from a normal subject. In some cases, the target cell is present in an organ (e.g., an ex vivo organ).

In some cases, the target cell(s) is in vivo, e.g., present in an individual. Suitable individuals include, but are not limited to, humans; non-human mammals; mammals (e.g., felines such as cats; canines such as dogs; equines such as horses; ungulates; bovines such as cows; ovines such as sheep; caprines such as goats; and the like); insects; arthropods; arachnids; birds; amphibians; reptiles; invertebrates; vertebrates; fungi; plants; and the like.

Where the target cell(s) is in vivo in an individual, a method of the present disclosure can comprise administering to the individual a composition of the present disclosure. Any of a variety of routes of administration can be used, including, e.g., intravenous, intramuscular, subcutaneous, intratumoral, peritumoral, intracranial, etc. A composition of the present disclosure can be administered locally or systemically.

In certain embodiments, the target cell has a reducing intracellular environment which triggers reduction of $M^1$ to release $M^2$. In certain cases, the reduction of $M^1$ to $M^2$ is achieved by glutathione reduction.

In certain other embodiments, the acidic environment of the target cell triggers release of the metal ion. For example, where the pH of the target cell is less than 7.0, e.g., where the pH of the cell is from about 5.0 to about 6.9, from about 4.0 to about 5.0, from about 3.0 to about 4.0, from about 2.0 to about 3.0, or less than 2.0.

In certain embodiments, the metal ion is released by degradation of the ionophore compound after internalization of the receptor-ionophore complex.

In certain embodiments, the metal ion (e.g., $M^2$) is delivered to the endolysosomal pathway of the target cell by active transport via the site-specific targeting moiety. In some cases, the targeting moiety is significantly hydrophilic, such that the passive diffusion of the ionophore compound is hindered and receptor-mediated uptake ensues. In some cases, the targeting moiety is significantly large, such that passive diffusion of the ionophore compound is hindered and receptor-mediated uptake ensues. In certain cases, the linker that links the ionophore and targeting moiety is a hydrophilic group which provides enhanced hydrophilicity to the ionophore compound, and thus facilitates receptor-mediated uptake.

In some embodiments, delivery of the metal ion ($M^2$) results in greater than 2-fold increase in the amount of metal ion in the target cell relative to the basal levels of the metal ion in the cell before treatment, such as 3-fold, 4-fold, 5-fold, 6-fold, 7-fold, 8-fold, 9-fold, 10-fold, or an even greater increase in the amount of metal ion. In some cases, the amount of metal ion in the target cell is increased by at least 4-fold relative to the basal levels of the metal ion in the target cell before treatment.

In certain embodiments, the subject method is a method of delivering a copper ion intracellularly to a target cell. In certain embodiments the method comprising: contacting the target cell with a subject ionophore compound (e.g., as described herein); wherein: M is a first ionic from of the copper ion ($Cu^{2+}$), wherein the ionophore has a higher affinity for $Cu^{2+}$ over a second ionic from $Cu^+$; and T is a targeting moiety for the target cell; to internalize the ionophore within the target cell and reduce $Cu^{2+}$ to $Cu^+$ thereby intracellularly releasing the metal ion ($Cu^+$) from the ionophore.

In some cases, the ionophore compound retains copper (e.g., $Cu^{2+}$) selectively in the presence of about 1000-fold excess of other ions, such as $Zn^{2+}$ and $Fe^{2+}$, which are two other abundant intracellular transition metal ions. See, e.g., Carter et al. *E. Chem. Rev.* 2014, 114, 4564.

In some embodiments, the amount of copper in the target cell is increased by 2-fold relative to the basal levels of the copper ion in the cell before treatment, such as 3-fold, 4-fold, 5-fold, 6-fold, 7-fold, 8-fold, 9-fold, 10-fold, or an even greater increase in the amount of copper ion in the target cell. In some cases, the amount of copper ion in the target cell is increased by at least 4-fold relative to the basal levels of the copper ion in the target cell before treatment.

Selective delivery can be assessed using any convenient methods relative to a control cell or tissue. In some cases, selective delivery is assessed via cellular uptake of the compound or intracellular levels of the metal ion that is released. Assays that assess binding of compound to the target cell versus a control cell can also be utilized.

Methods of Treatment

As summarized above, aspects of the present disclosure include methods of treating a metal deficiency in an individual in need thereof, the method comprising administering to the individual a pharmaceutical composition comprising a subject ionophore compound and releasing the metal from the ionophore at a targeted site in the individual. In certain cases, the pharmaceutical composition comprises one or more additional therapeutic agents. In certain cases, the targeted site is selected from, liver, adipose, heart and brain. In certain cases, the metal deficiency is selected from copper deficiency, iron deficiency, zinc deficiency, cobalt deficiency and magnesium deficiency. In some instants, the metal deficiency is a copper deficiency. In certain cases, the copper ion at the targeted site is increased by at least 4-fold, such as at least 4.5-fold, at least 5-fold, at least 5.5-fold, at least 6-fold or even more, relative to the basal levels of the copper ion before treatment.

In some embodiments, methods of treating a metal deficiency alleviate at least one symptom associated with a disease state, disorder or condition associated with the metal deficiency in the individual. In some embodiments, the subject methods are methods of preventing or treating the disease state, disorder or condition associated with a metal deficiency. Diseases and conditions of interest include those correlated with a metal deficiency. In some cases, the disease or condition of interest is associated with a copper deficiency. In some cases, the disease or condition of interest is associated with an iron deficiency. In some cases, the disease or condition of interest is associated with a zinc deficiency. In some cases, the disease or condition of interest is asso-ciated with a cobalt deficiency. In some cases, the disease or condition of interest is associated with a manganese deficiency.

Target diseases and conditions of interest that may be modulated or treated according to the subject methods include any convenient disease or condition associated with a metal deficiency, including but not limited to, Menkes disease, familial amyotrophic lateral sclerosis, inflammatory condition, osteoarthritis, hypertension, osteoporosis, would healing, immunomodulation, neurodegenerative disorders, cardiovascular disease metabolic dysfunction and metabolic disorders.

In some instances of the subject methods, the target disease or condition associated with a metal deficiency is a metabolic disorder, e.g., non-alcoholic fatty liver disease (NAFLD). In some cases, administration of the subject compounds and compositions can target the liver and provide a significant increase of the metal ion (e.g., $Cu^+$) in the liver with no significant differences in metal levels in the other organs of the individual. In some cases, the metal ion in the liver is increased by 100% or more, 150% or more, 200% or more, 250% or more, 300% or more, or even more, following administration of a subject ionophore composition relative to basal levels of the metal ion in the liver. It is known that the liver expresses high levels of asialoglycoprotein receptor (ASPGR), e.g., approximately 500,000 ASGPR copies per primary hepatocyte. As such, in some cases, the subject ionophore compound is designed to bind ASPGR to facilitate the targeting delivery of the metal ion to the liver.

In some instances of the subject methods, the target disease or condition associated with a metal deficiency is an inflammatory condition. Inflammation is linked to the metabolic syndrome at the cellular level by way of damage to the antioxidant-defense enzyme system and mitochondria. This damage, in turn, can propagate further production of pro-inflammatory mediators. Inflammatory conditions of interest include, but are not limited to, chronic inflammatory diseases (e.g., cardiovascular disease), cancer, multiple sclerosis (MS), experimental autoimmune encephalomyelitis (EAE), oxidation stress related conditions.

In some instances of the subject methods, the disease or condition associated with metal deficiency is osteoarthritis. In some instances of the subject methods, the target disease or condition is osteoporosis. Symptoms of interest that can be ameliorated according to the subject methods include, but are not limited to, pain, joint inflammation, loss of joint fluid, immobility of joints, legs or fingers, decreased bone density and calcification.

In some cases of the subject methods, the disease or condition associated with metal deficiency is a neurodegenerative disorder. Neurodegenerative orders may include, Alzheimer's disease, mild cognitive impairment (MCI), or dementia, Huntington's disease, autism, schizophrenia, cognitive decline as secondary effect of disease or medical treatment, depression, dementia, sleep disorder, anxiety, attention deficit hyperactivity disorder (ADHD), migraine, headache, stroke, and neuropathy.

In some embodiments, the subject methods for treating a metal deficiency may inhibit the symptoms or conditions (disabilities, impairments) associated with an associated disease or condition as described in detail above. It is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition or disease, but rather, can encompass a result which includes reducing or preventing the symptoms that result from the condition or disease, reducing or preventing the occurrence of such symptoms (either quantitatively or qualitatively), reducing the severity of such symptoms or physiological effects thereof, and/or enhancing the recovery of the individual after experiencing symptoms.

As used herein, the phrase "alleviating at least one symptom associated with" a disorder, disease, or condition (e.g., as described herein) denotes reversing, inhibiting the progress of, or preventing the disorder or condition to which such term applies, or reversing, inhibiting the progress of, or preventing one or more symptoms of the disorder or condition to which such term applies. Specifically, a composition of the present disclosure (such as any of the ionophore compounds disclosed herein), when administered to an individual, can treat or prevent metal deficiency and thereby treat or prevent one or more of the symptoms or conditions of the associated disease or condition and/or reduce or alleviate symptoms of or conditions associated with these disorders. As such, protecting an individual from the effects or symptoms resulting from the target disease or condition includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present disclosure as compared to those that have not.

The methods provided herein can also be practiced in a "neoadjuvant setting," i.e., the method can be carried out before a primary/definitive therapy. In some embodiments, the individual has previously been treated. In some embodiments, the individual has not previously been treated. In some embodiments, the treatment is a first line therapy.

The amount of ionophore compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a biomarker of the target disease or condition. Assessment of the effectiveness of the methods of treatment on the subject can include assessment of the subject before, during and/or after treatment, using any convenient methods. Aspects of the subject methods further include a step of assessing the therapeutic response of the subject to the treatment. In some embodiments, to detect $Cu^+$ a Copper Caged Luciferin-1 (CCL-1) probe can be utilized. See, e.g., Heffern et al. (2016) *J. Proc. Natl. Acad. Sci.* 113, 14219. In some embodiments, the method includes assessing the condition associated with a metal deficiency in the subject, including diagnosing or assessing one or more symptoms of the subject which are associated with the disease or condition of interest being treated (e.g., as described herein).

Combination Therapies

The subject ionophore compounds can be administered to a subject alone or in combination with an additional therapeutic agent, i.e., second, active agent. As such, in some cases, the subject method further comprises administering to the subject at least one additional therapy or compound. Any convenient agents may be utilized, including compounds useful for treating metal-deficiency associated conditions or any disease or condition as described herein. In some cases, the subject compounds are administered to negate the effect of a drug the subject is taking which causes the metal deficiency. In some cases, administration of the subject agent can provide for continued treatment with a drug that causes the metal deficiency.

The terms "agent," "compound," and "drug" are used interchangeably herein. For example, selective ionophore compounds can be administered alone or in conjunction with one or more other drugs, such as drugs employed in the treatment of a disease or condition associated with a metal deficiency (e.g. as described herein). In some embodiments, the method further includes co-administering concomitantly or in sequence a second agent. In some embodiments, the method further includes performing a blood transfusion (e.g., exchange transfusion) on the subject.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and compounds of the present disclosure.

In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compounds and the second active agent. In pharmaceutical dosage forms, the compounds may be administered in the form of their pharmaceutically acceptable salts, or they may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific compound, the nature of the delivery vehicle, and the like. Preferred dosages for a given compound or agent are readily determinable by those of skill in the art by a variety of means.

Kits & Systems & Other Compositions

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. In some embodiments, the subject system or kit includes a dose of a subject compound (e.g., as described herein) and a dose of a second active agent (e.g., as described herein) in amounts effective to treat a subject for a metal deficiency or a disease or condition associated with a metal deficiency (e.g., as described herein).

Also provided are preservative preparations and kits that find use as a preservative for cellular samples, e.g., erythrocyte cells, by improves preservation of erythrocyte storage by decreasing the degree of hemolysis of the cells over time. In some cases, the preparations provide for storage stability of the cellular sample. Preservative preparations are compositions that include a ionophore compound (e.g., as described herein) (for example one or more of the subject compounds), either alone or in the presence of one or more additional components, e.g., any convenient components that find use in stabilizing or storing cells. In some cases, the preservative preparation finds use in conjunction with a blood collection tube or a cell preservative tube. In some cases, the tube is suitable for evacuation to facilitate sample collection or transfer.

Kits and systems for practicing the subject methods may include one or more pharmaceutical formulations. As such, in certain embodiments the kits may include a single pharmaceutical composition, present as one or more unit dosages, where the composition may include one or more ionophore compounds (e.g., as described herein). In some embodiments, the kit may include two or more separate pharmaceutical compositions, each containing a different active agent, at least one of which is an ionophore compound (e.g., as described herein).

Also of interest are kits and systems finding use in the subject methods, e.g., as described above. Such kits and systems may include one or more components of the subject methods, e.g., antioxidant, cells, enzyme substrates, dyes, buffers, etc. The various kit components may be present in the containers, e.g., sterile containers, where the components may be present in the same or different containers.

In addition to the above-mentioned components, a subject kit may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An ionophore compound of the formula (I):

(T-L)$_n$-(Z-M)   (I)

wherein:
T is a targeting moiety (e.g., a cell targeting moiety, a tissue targeting moiety or an organ targeting moiety);
L is a linker;
M is a metal ion;
Z is an ionophore capable of complexing M; and
n is an integer from 1 to 20 (e.g., 1 to 10, 1 to 6, 1 to 3 or 1 to 2).

Aspect 2. The ionophore compound of aspect 1, wherein T is selected from a liver-targeting moiety, a mitochondria-targeting moiety, a nucleus-targeting moiety, an adipose-targeting moiety, a heart-targeting moiety and a brain targeting moiety.

Aspect 3. The ionophore compound of aspect 1 or 2, wherein T is selected from a saccharide, a polysaccharide, a multivalent saccharide, an amino sugar, a peptide, a small molecule drug, a small molecule drug fragment and a phosphonium cation.

Aspect 4. The ionophore compound of aspect 3, wherein T is selected from galactose, a galactose derivative, a multivalent galactose conjugate, an amino sugar derivative of galactose and a multivalent amino sugar derivative of galactose.

Aspect 5. The ionophore compound of any one of aspects 1 to 4, wherein Z is selected from:

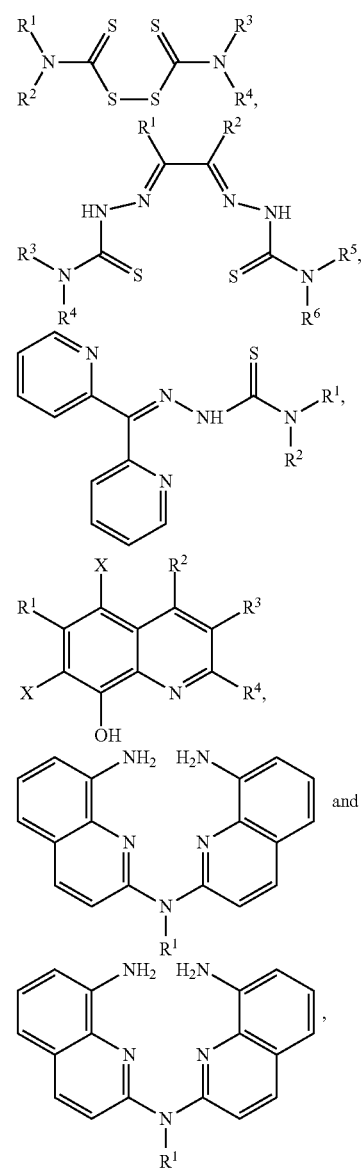

wherein:

X is a halogen; and $R^1$, $R^2$, $R^3$, $R^4$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl and substituted acyl.

Aspect 6. The ionophore compound of aspect 5, wherein the ionophore is:

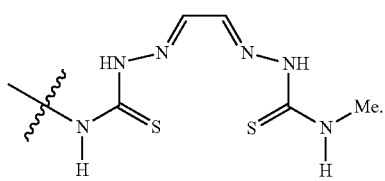 [SMILES: *NC(=S)N/N=C/C=N/NC(=S)NC]

Aspect 7. The ionophore compound of any one of aspects 1 to 6, wherein L is selected from a linear or branched alkyl, alkenylene, alkynylene, arylene, alkarylene, aralkylene, alkoxy, alkamine, polyethylene glycol (PEG), a modified PEG, an oligoethyleneglycol, a phosphate, a phosphonate, a boric acid, a carboxylate, a sulfate, a sulfonate, an amine, a glycerol, a sugar, an amino acid and a substituted amino acid.

Aspect 8. The ionophore compound of aspect 7, wherein L is a hydrophilic group selected from polyethylene glycol (PEG), modified PEG and a oligoethyleneglycol.

Aspect 9. The ionophore compound of any one of aspects 1 to 8, of the formula (II)

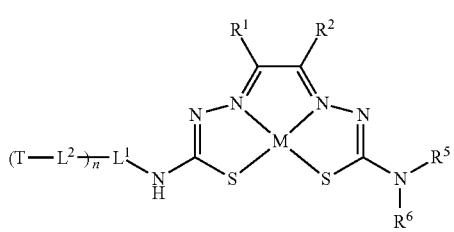

(II)

wherein:

$R^1$, $R^2$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl, substituted acyl and $-L^1(L^2-T)_n$;

T is a targeting moiety;

$L^1$ is a bond or a linker;

$L^2$ are each independently a linker selected from a linear or branched alkyl, alkenylene, alkynylene, arylene, alkarylene, aralkylene, alkoxy, alkamine polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid and a substituted amino acid;

M is a metal ion; and n is an integer from 1 to 20.

Aspect 10. The ionophore compound of aspect 9, wherein T is selected from, a peptide comprising the sequence CKGGRAKDC, a peptide comprising the sequence APWHLSSQYSRT, a peptide comprising the sequence TFFYGGSRGKRNNFKTEEY,

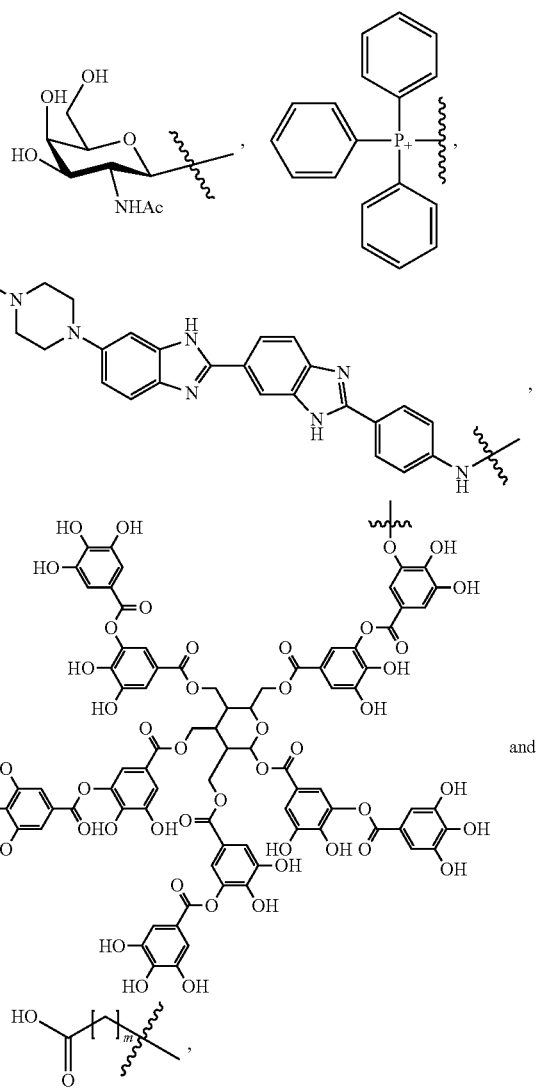

and

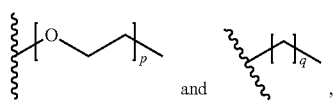

wherein m is an integer from 1 to 20.

Aspect 11. The ionophore compound of aspect 9 or 10, wherein each $L^2$ are independently selected from:

wherein p and q are each independently an integer from 1 to 20.

Aspect 12. The ionophore compound of any one of aspects 1 to 11, wherein M is selected from a copper ion, an iron ion, a zinc ion, a cobalt ion and a manganese ion.

Aspect 13. The ionophore compound of aspect 12, wherein M is $Cu^{2+}$ and the ionophore has decreased affinity for $Cu^+$, such that the ionophore is capable of complexing $Cu^{2+}$.

Aspect 14. The ionophore compound of aspect 12, wherein M is $Fe^{3+}$ and the ionophore has decreased affinity for $Fe^{2+}$, such that the ionophore is capable of complexing $Fe^{3+}$.

Aspect 15. The ionophore compound of any one of aspects 1 to 14, having one of the following structure:

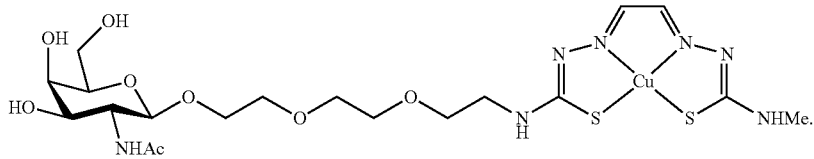

Aspect 16. A pharmaceutical composition, comprising:
a) an ionophore compound of any one of aspects 1-15; and
c) a pharmaceutically acceptable excipient.

Aspect 17. A pharmaceutical composition, comprising:
a) an ionophore compound of any one of aspects 1-15;
b) one or more additional therapeutic agents; and
c) a pharmaceutically acceptable excipient.

Aspect 18. A method of delivering a metal ($M^2$) intracellularly to a target cell, the method comprising:
contacting the target cell with an ionophore compound of any one of aspects 1-15; wherein:
M is a first ionic from of the metal ion ($M^1$), wherein the ionophore has a higher affinity for $M^1$ over a second ionic from $M^2$; and
T is a targeting moiety for the target cell;
to internalize the ionophore within the target cell and reduce $M^1$ to $M^2$ thereby intracellularly releasing the metal ion ($M^2$) from the ionophore.

Aspect 19. The method of aspect 18, wherein the cell is in vitro.

Aspect 20. The method of aspect 18, wherein the cell is in vivo in a human or non-human organism.

Aspect 21. The method of aspect 20, comprising administering the composition to the organism.

Aspect 22. The method of any one of aspects 18 to 21, wherein the target cell has a reducing intracellular environment which triggers reduction of $M^1$ to release $M^2$.

Aspect 23. The method of any one of aspects 18 to 22, wherein $M^2$ is delivered to the endolysosomal pathway of the target cell by active transport via the site-specific targeting moiety.

Aspect 24. A method of treating a condition associated with a metal deficiency in an individual in need thereof, the method comprising:
administering to the individual a pharmaceutical composition of aspect 16 or 17; and
releasing the metal from the ionophore at a targeted site in the individual.

Aspect 25. The method of aspect 24, wherein the targeted site is selected from, liver, adipose, heart and brain.

Aspect 26. The method of aspect 24 or 25, wherein the metal ion is copper.

Aspect 27. The method of aspect 26, wherein the amount of copper ion at the targeted site is increased by at least 4-fold relative to the basal levels of the copper ion before treatment.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1: Introduction

To address matters described above, an approach for site-specific metal deliver, termed Targeted Ionophore-based Metal Supplementation (TIMS), was developed. The TIMS approach relies on pairing metal delivering ionophores with targeting ligands that recognize specific cell surface receptors localized to cells and tissues of interest.

Figure 1B:
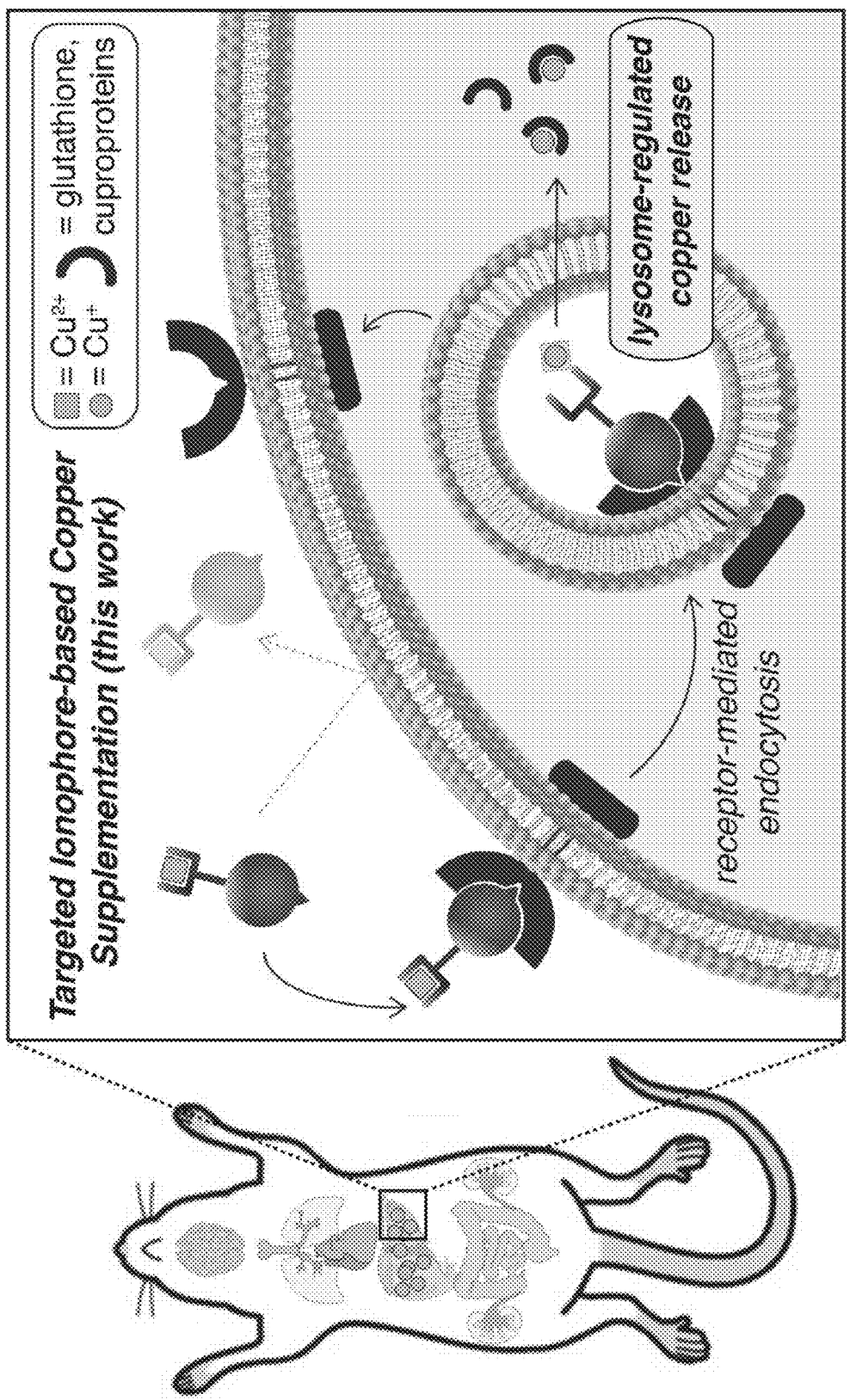
FIG. 1B shows receptor-mediated metal accumulation with minimal off-target delivery caused by ionophores described herein.

The TIMS strategy is shown in FIG. 1B, wherein (i) ligand-receptor recognition triggers endocytosis and internalization of the receptor-ionophore complex, (ii) the complex releases the metal in the endolysosomal pathway through either intracellular reduction or degradation, and (iii) the metal ion binds to metal storage or trafficking proteins, which can then utilize the metal as needed. In support of this approach, recent studies have shown that the lysosome is a key organelle in dynamic metal regulation, (see e.g., Blaby-Haas et al., J. Biol. Chem. 2014, 289, 28129; Polishchuk et al., Metallomics 2016, 8, 853; Polishchuk et al., Dev. Cell 2014, 29, 686) and mediating metal delivery through this organelle's homeostatic cues may offer a safer alternative for increasing bioavailable metal ion pools compared to unregulated cytosolic metal release.

Compounds Cu(gtsm) and Gal-Cu(gtsm) have the chemical structure shown below.

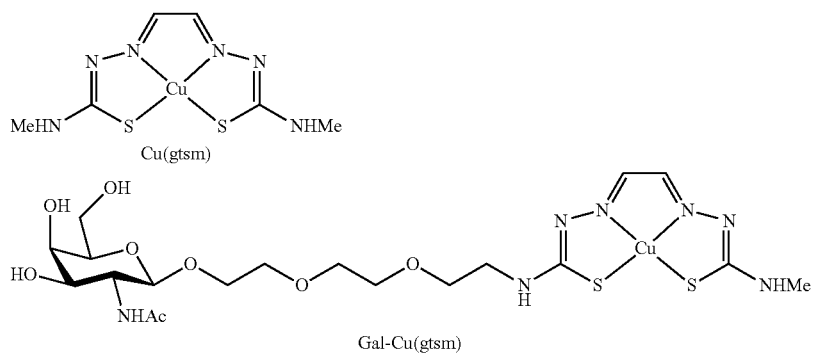

Figure 1C:
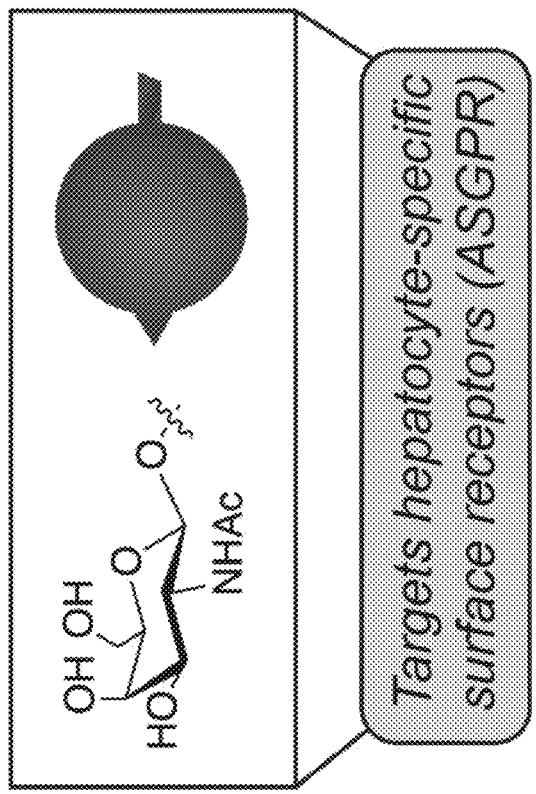
FIG. 1C shows bifunctional ionophore design for Gal-Cu (gtsm) that uses a triethyleneglycol linker.
Figure 1C:
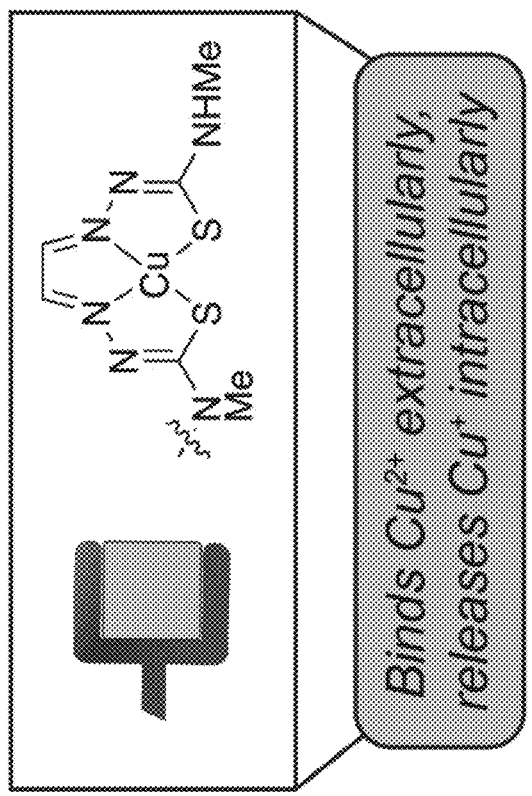

With these design principles in mind, a bifunctional ionophore that targets the asialoglycoprotein receptor (AS-PGR), a C-type lectin membrane receptor that is specifically expressed in the liver at high levels (e.g., ca. 500,000 ASGPR copies per primary hepatocyte; D'Souza et al., J. Control. Release 2015, 203, 126.) was synthesized, as shown in FIG. 1C. An N-acetylgalactosamine (GalNAc) ligand was used as the targeting group, which binds ASGPR with a $K_d$ value of ca. $10^{-5}$ $M^{-1}$.

Liver targeting via ASGPR/galactose recognition is a strategy that has been used to deliver drugs, proteins, siRNA and CRISPR-Cas9; related work has employed metal chelators to address copper excess-based disorders such as Wilson's disease. Monovalent targeting group were used for their atom economy and scalable synthesis for longitudinal animal studies.

The design for the TIMS agent includes a targeting group attached to a metal ionophore rather than a metal chelator. A GalNAc targeting moiety was paired with the bisthiosemicarbazone complex Cu(gtsm) (FIG. 1C), which is a copper ionophore that has been explored as a potential therapeutic for neurodegenerative disorders and cancer.

The metal binding and Cu release properties of Cu(gtsm) complex provide for release of the copper ion in a target cell. The gtsm ligand binds $Cu^{2+}$ ($K_d \sim 10^{-18}$ $M^{-1}$) more tightly than $Cu^+$ ($K_d \sim 10^{-13}$ $M^{-1}$),[64] and releases $Cu^+$ upon reduction in the intracellular medium where it can metalate copper-binding small molecules and proteins (Crouch et al., Proc. Natl. Acad. Sci. 2009, 106, 381; Cater et al., ACS Chem. Biol. 2013, 8, 162; Price et al., Inorg. Chem. 2011, 50, 9594). The ionophore and targeting GalNAc ligand were linked with a triethylene glycol chain to provide enhanced hydrophilicity.

Synthesis and Testing of Cu(gtsm) and Gal-Cu(gtsm)

Cu(gtsm) was synthesized using literature methods (Dearling et al., J. Biol. Inorg. Chem. 2002, 7, 24). Gal-Cu(gtsm) was synthesized using a convergent synthetic approach where the ionophore and targeting group fragments were synthesized independently and then linked together through a transamination reaction in the penultimate step (Klayman, D. L.; Lin, A. J. Org. Prep. Proced. Int. 1984, 16, 79; Brett, M. P.; John, A. K.; Denis, B. S.; Jonathan, M. W.; Donnelly, P. S. Inorg. Chem. 2010, 49, 1884).

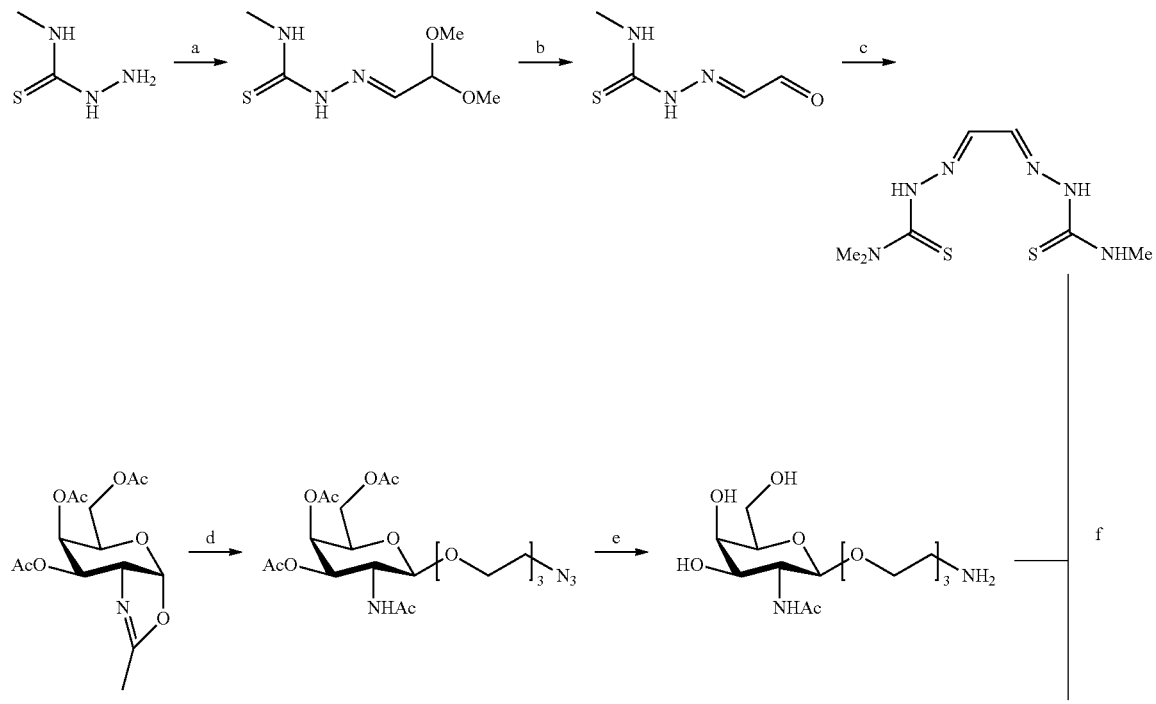

-continued

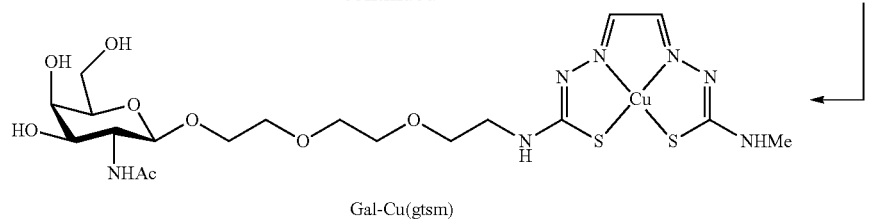

Gal-Cu(gtsm)

The glyoxal unit with an acetal protecting group was installed onto thiosemicarbazide 1, then unmasked acetal 2 with lithium tetrafluoroborate to give iminoacetaldehyde 3 (see e.g., PCT/AU2007/001792). Condensation with 4,4-dimethyl-3-thiosemicarbazide gave the asymmetrically substituted gtsm analogue 4. Oxazoline 5 (see e.g., Wang et al., Chem. Commun. 2011, 47, 11240) was reacted with azidotriethylene glycol in the presence of trimethylsilyl trifluoromethanesulfonate to access the azide-protected peracetylated GalNAc 6. The azide and O-acetyl groups were deprotected in a single palladium-catalyzed hydrogenation reaction to give GalNAc amine 7. Transamination between 4 and 7 gave apo-Gal-H$_2$gtsm, which was then metalated with copper diacetate to give Gal-Cu(gtsm).

Figure 2:
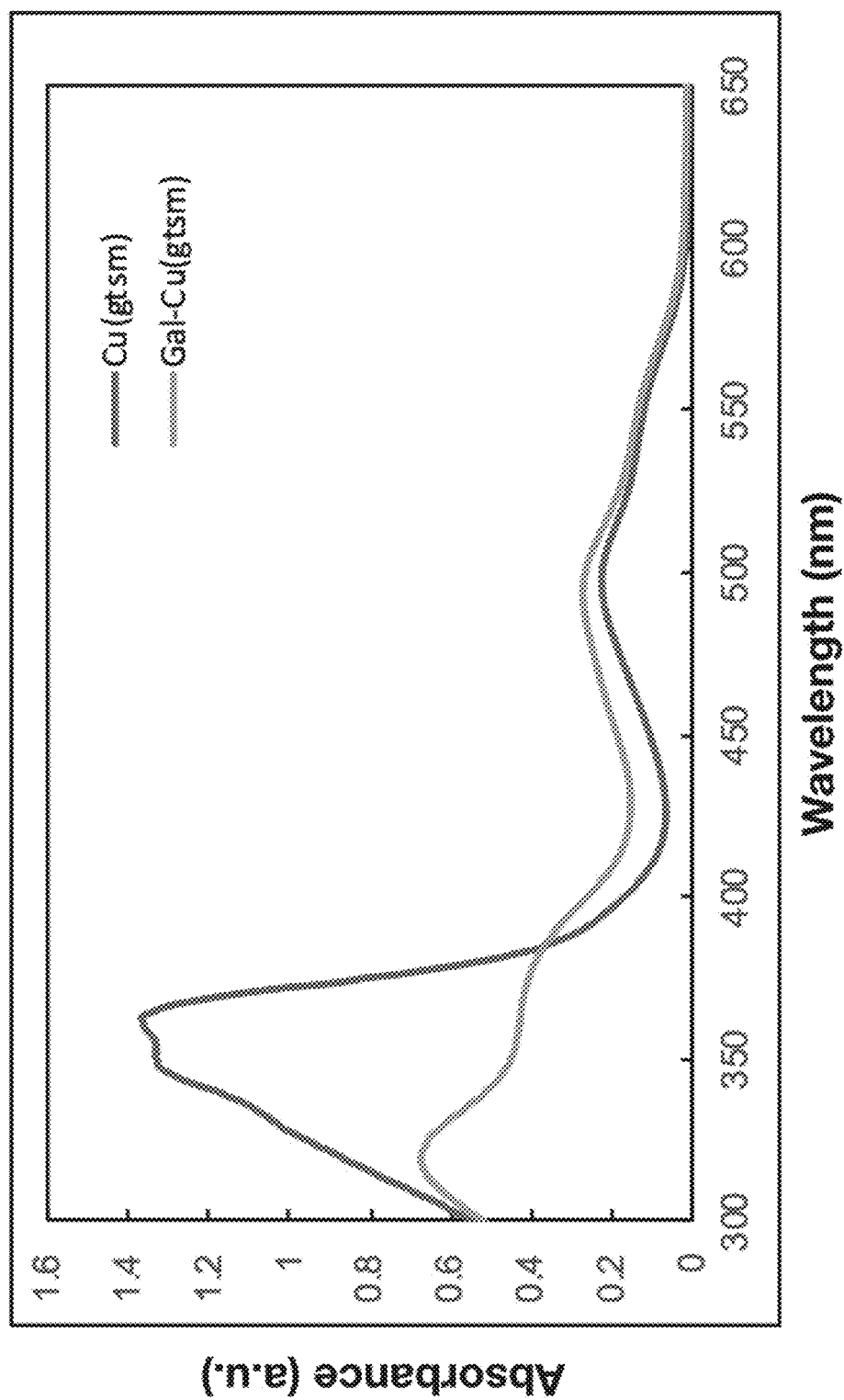
FIG. 2 shows UV-vis absorbance spectra of Cu(gtsm) and Gal-Cu(gtsm) at 50 µM in DMSO.
Figure 3:
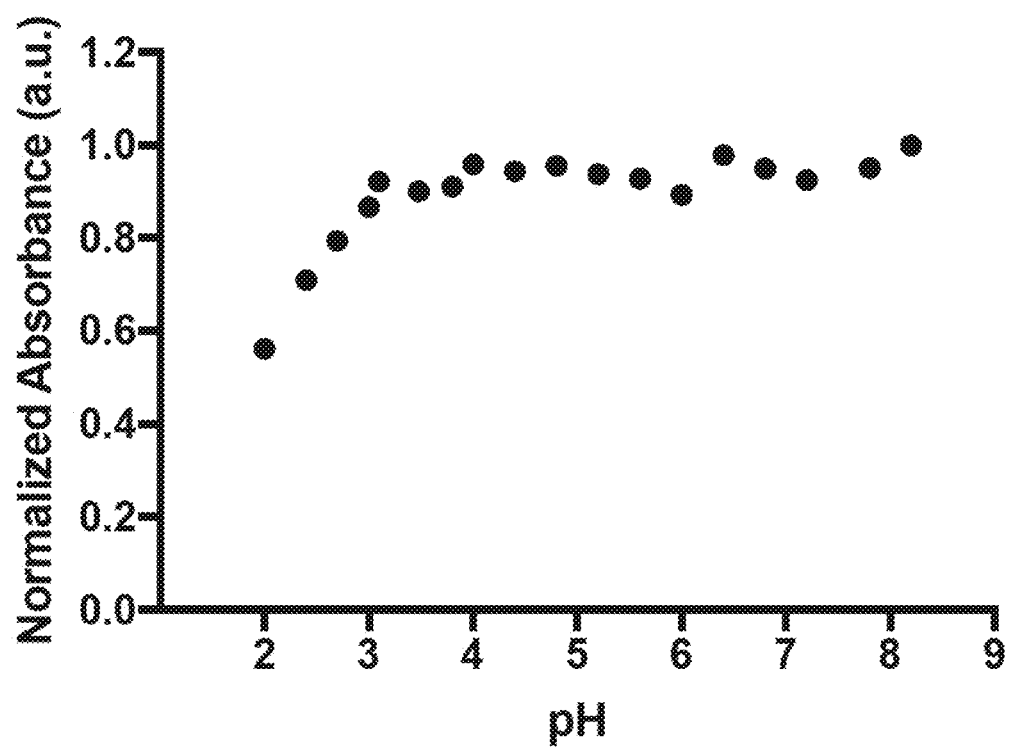
FIG. 3 shows the stability of Gal-Cu(gtsm) in aqueous solutions at different pH values.
Figure 4:
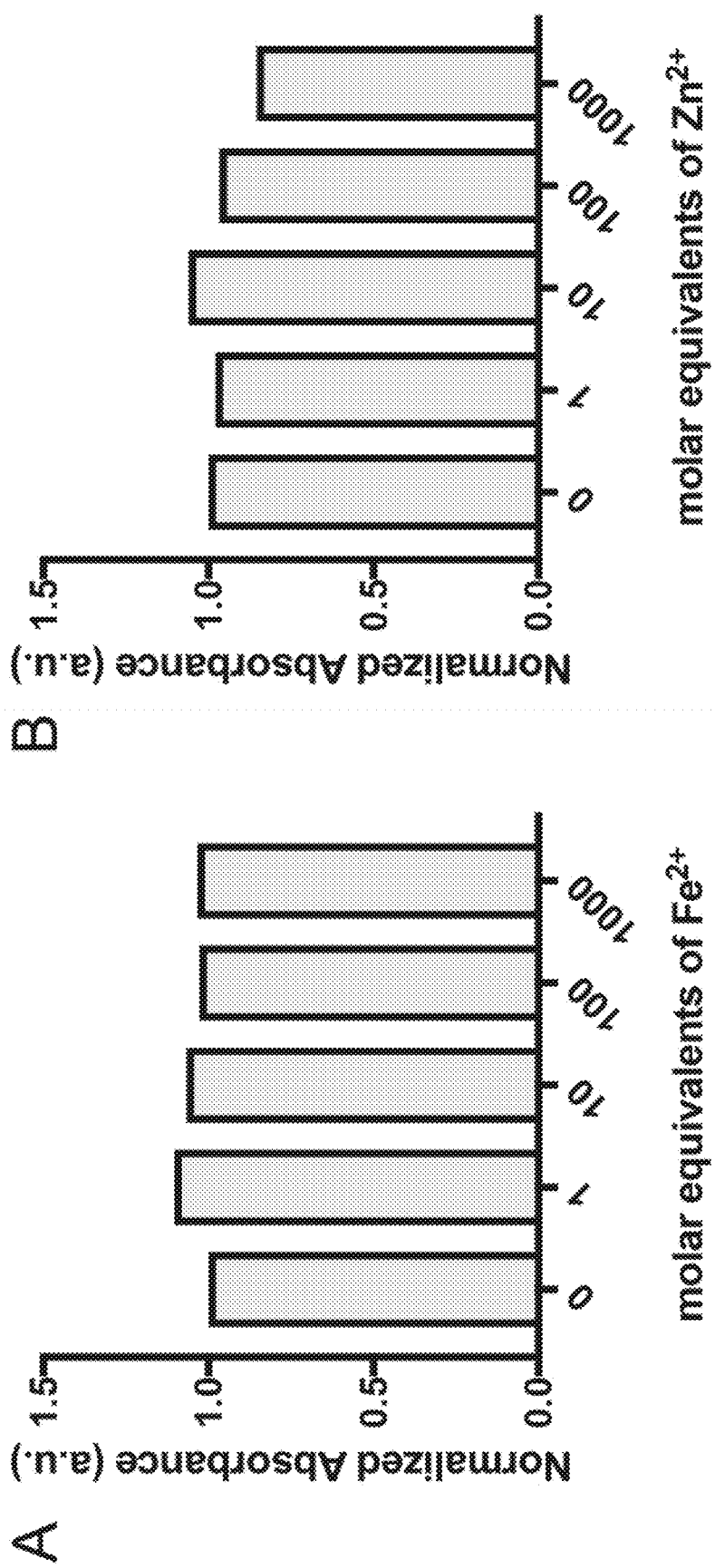
FIG. 4 shows the retention of copper selectivity of Gal-Cu(gtsm) in the presence of $Fe^{2+}$ and $Zn^{2+}$.

Log P measurements with a shake-flask octanol-water partition experiment confirmed that Gal-Cu(gtsm) (log P=−1.03±0.10) is more hydrophilic than Cu(gtsm) (log P=1.39±0.14).[66,71] It was found that Gal-Cu(gtsm) forms colloids in aqueous buffer with a number-weighted hydrodynamic diameter of 4.60±0.69 nm whereas Cu(gtsm) does not. Cu(gtsm) and Gal-Cu(gtsm) demonstrate similar Cu-ligand charge transfer absorption band characteristics (FIG. 2). Further in vitro spectroscopic studies were performed to evaluate the stability of Gal-Cu(gtsm) under physiologically relevant conditions. It was found that the Gal-Cu(gtsm) complex is stable in aqueous buffers ranging from pH=3 to 8 (FIG. 3). The complex also retains copper selectively in the presence of 1000-fold excess of $Zn^{2+}$ and $Fe^{2+}$ (FIG. 4), which are two other abundant intracellular transition metal ions.

Example 2: ASGPR-Dependent Copper Delivery in Cell Culture

Figure 5A:
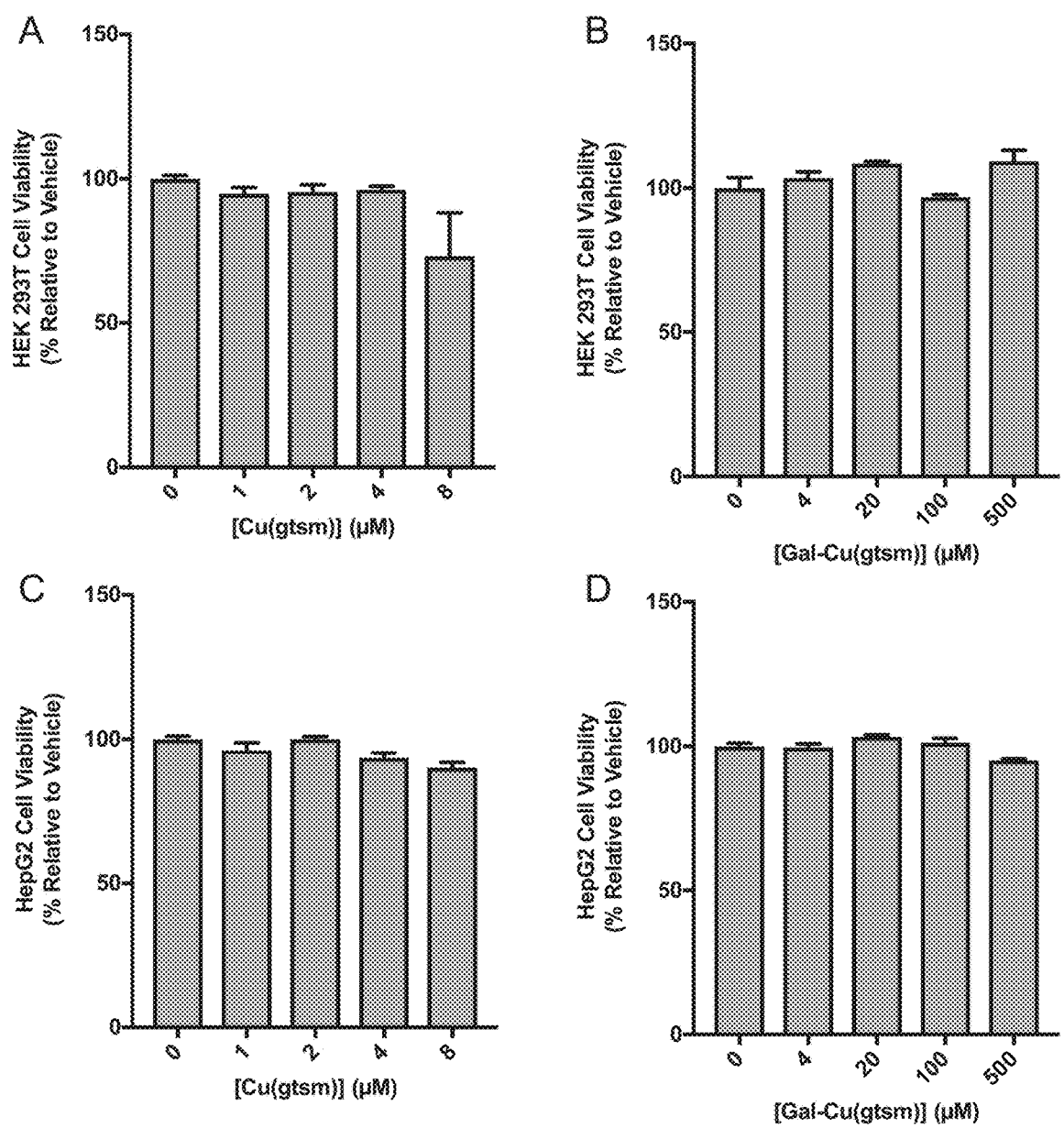
FIG. 5A shows the viability of HEK 293T cells or HepG2 cells treated with Cu(gtsm) or Gal-Cu(gtsm).
Figure 5B:
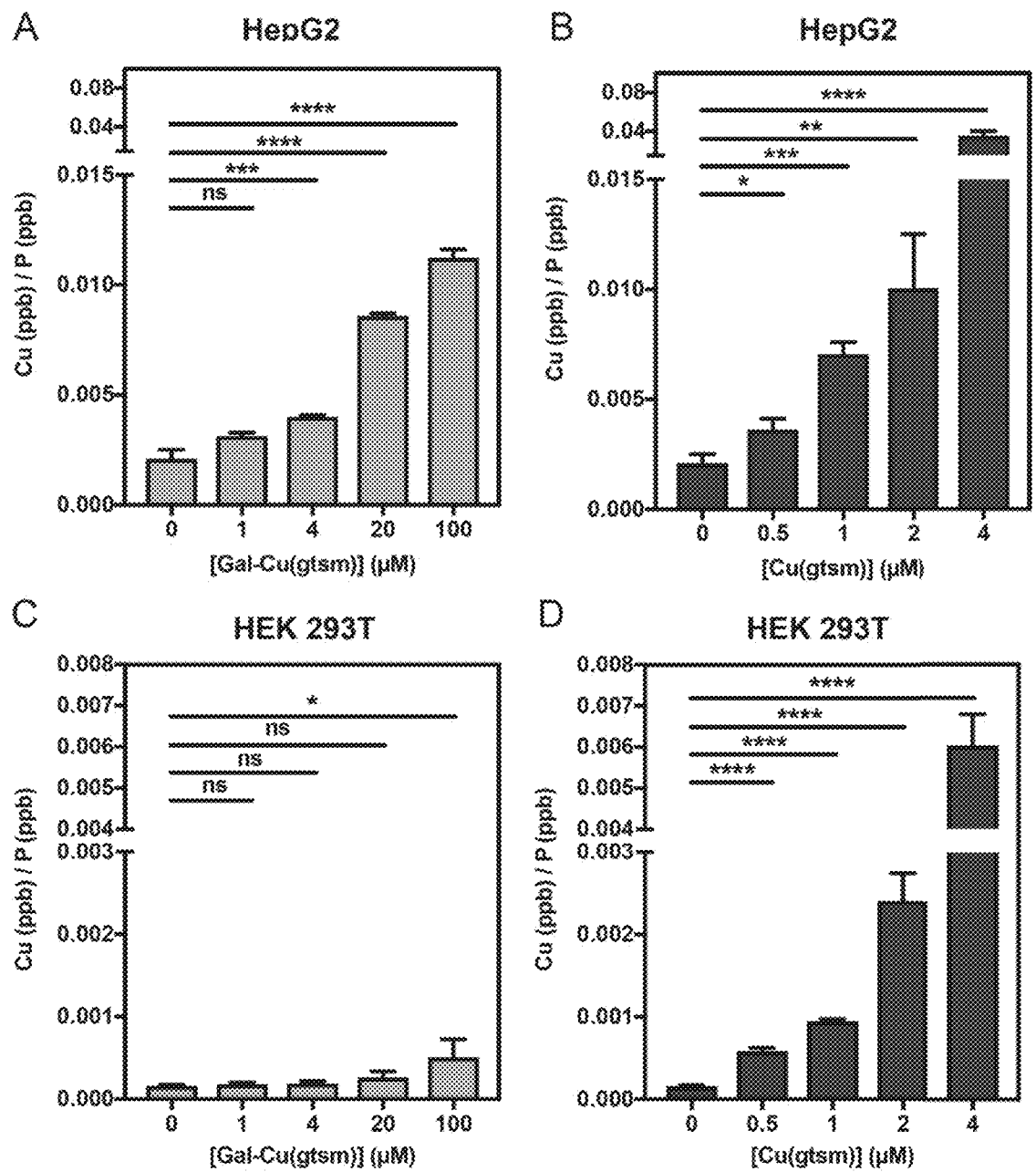
FIG. 5B shows the response of HEK 293T cells or HepG2 cells to treatment with Cu(gtsm) or Gal-Cu(gtsm).

The behaviors of Cu(gtsm) and Gal-Cu(gtsm) were characterized in cell lines with high ASGPR expression (HepG2) or no ASGPR expression (HEK 293T). Ionophore toxicity was evaluated in these cell lines using propidium iodide staining as a proxy for cell viability, finding that that Cu(gtsm) treatment is toxic at an 8 µM dose in HEK 293T cells, whereas Gal-Cu(gtsm) is non-toxic at a 500 µM dose in both cell lines (FIG. 5A). The intracellular Cu delivery abilities of the two ionophores was then evaluated using inductively coupled plasma-mass spectrometry (ICP-MS) to analyze total copper levels. It was found that Cu(gtsm) elicits dose-dependent increases in cellular copper content for both cell types, whereas Gal-Cu(gtsm) only demonstrates a robust dose-dependent copper delivery response in the ASGPR-expressing HepG2 cells (FIG. 5B).

Figure 6A:
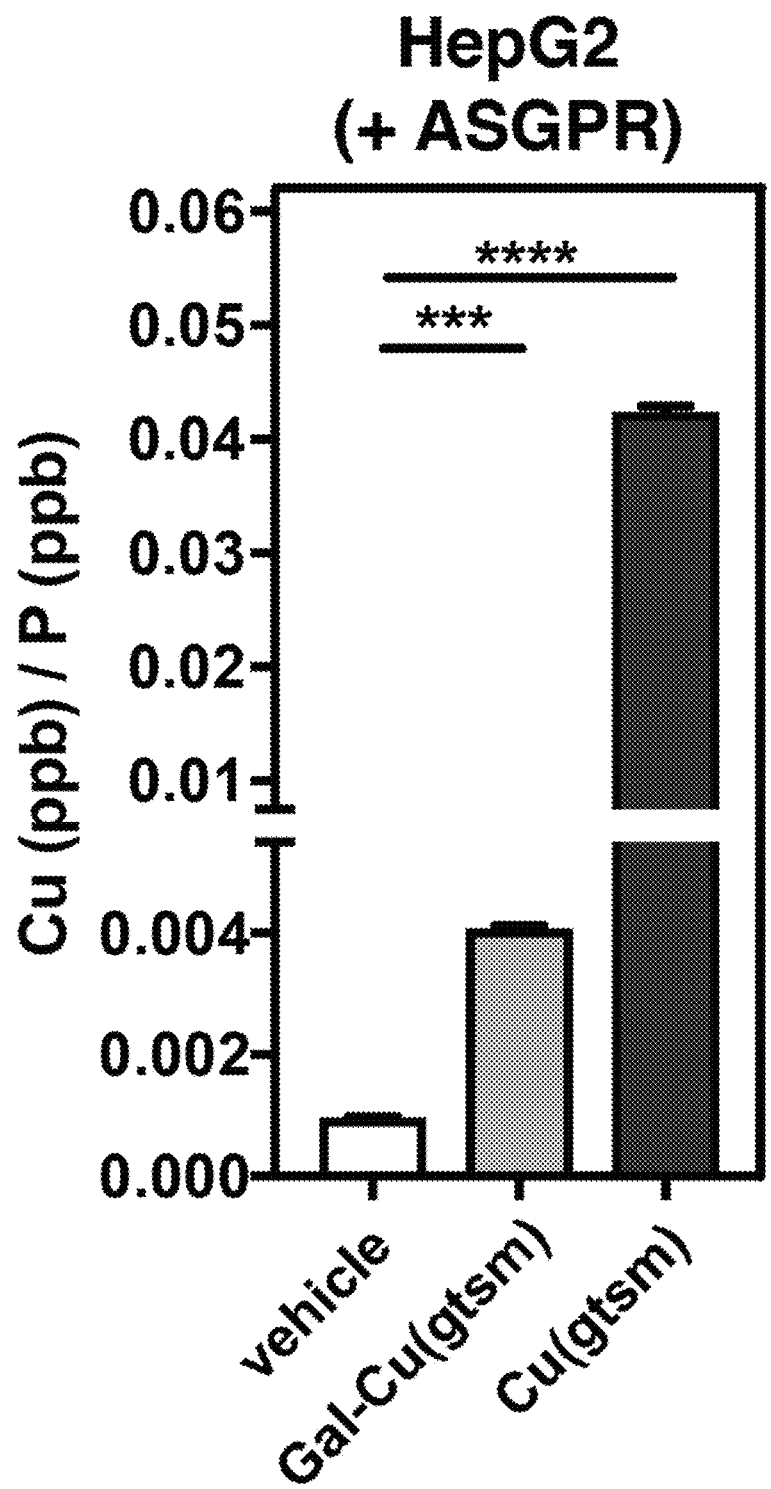
FIG. 6A shows ICP-MS studies comparing Cu levels upon 4 µM Cu-ionophore treatment (0.2% DMSO in serum-free DMEM) over a three-hour time course in HepG2 (ASGPR-expressing) cells.
Figure 6B:
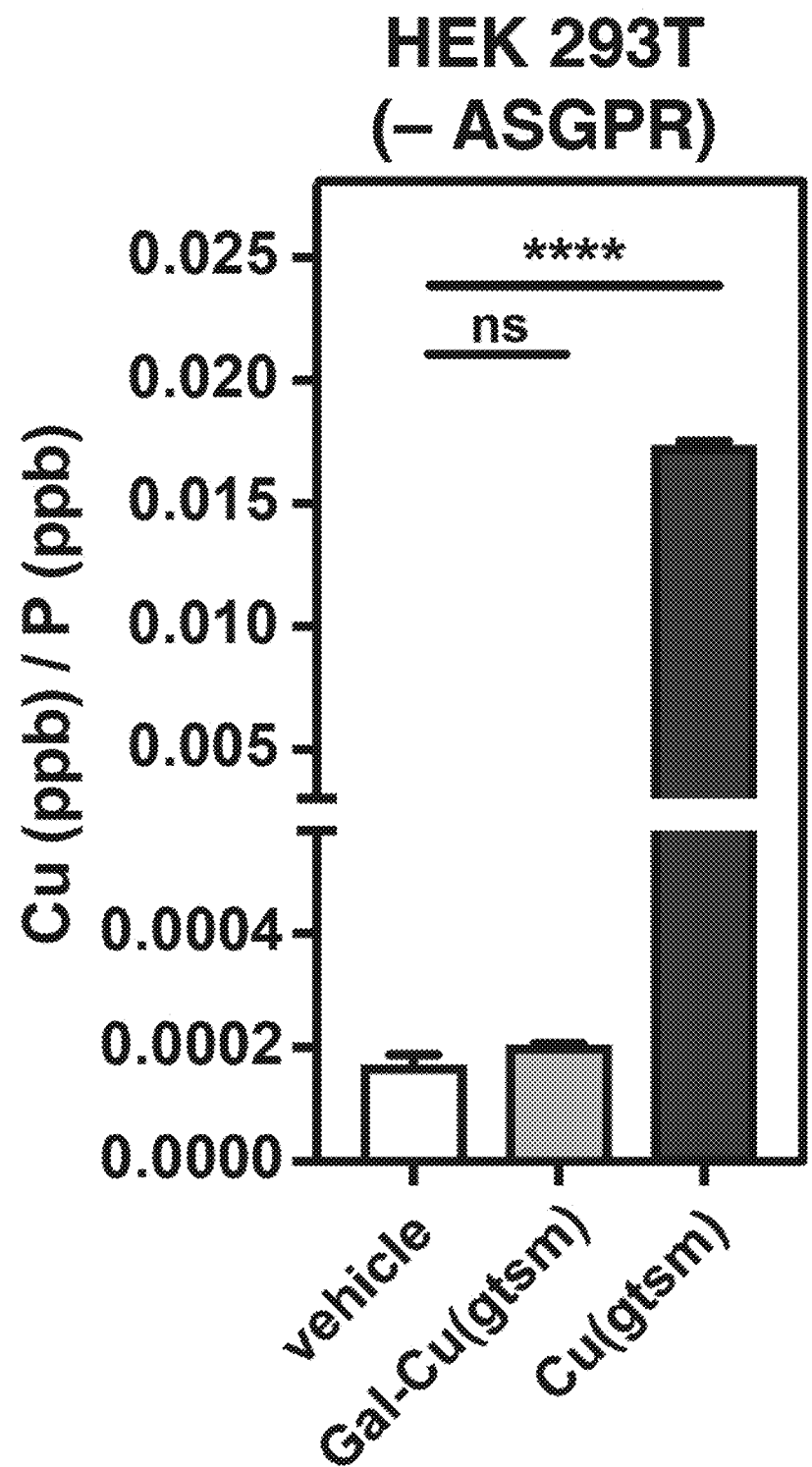
FIG. 6B shows ICP-MS studies upon 4 µM Cu-ionophore treatment (0.2% DMSO in serum-free DMEM) over a three-hour time course in HEK 293T (no ASGPR expression) cells.

FIGS. 6A-B highlights these differences at an equimolar 4 µM copper dose. HepG2 and HEK 293T cells were treated with either vehicle control, 4 µM Cu(gtsm), or 4 µM Gal-Cu(gtsm) for three hours. These figures display $^{63}$Cu/$^{31}$P ratios from ICP-MS data as a metric for characterizing copper delivery for each treatment condition, with the $^{31}$P signal normalizing for number of cells based on cellular phosphate content. FIG. 6A shows that Gal-Cu(gtsm) leads to a 4-fold Cu increase relative to the basal levels in HepG2 cells, while Cu(gtsm) treatment leads to a 45-fold increase in Cu content. In HEK 293T cells (FIG. 6B) that do not express ASGPR, Gal-Cu(gtsm) treatment does not increase cellular copper beyond basal levels, while Cu(gtsm) treatment leads to a 100-fold increase in Cu levels. The data show that Cu(gtsm) delivers copper unselectively to both cell types. Conversely, the hydrophilic Gal-Cu(gtsm) experiences limited passive diffusion and does not deliver copper to HEK 293T cells lacking ASGPRs, whereas copper delivery only occurs in the ASGPR-expressing HepG2 cells upon Gal-Cu(gtsm)/ASGPR recognition and internalization.

Figure 6C:
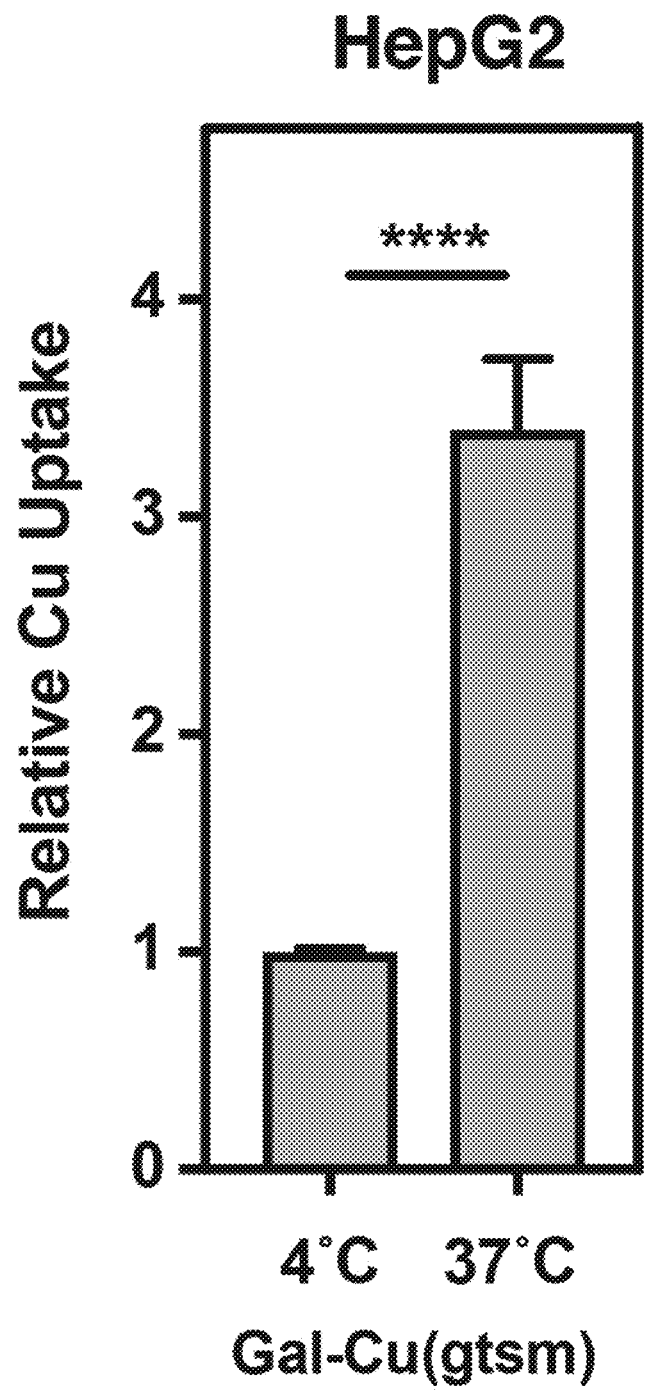
FIG. 6C shows copper supplementation by HepG2 cells at 4° C. or 37° C. that were treated with Gal-Cu(gtsm).
Figure 6D:
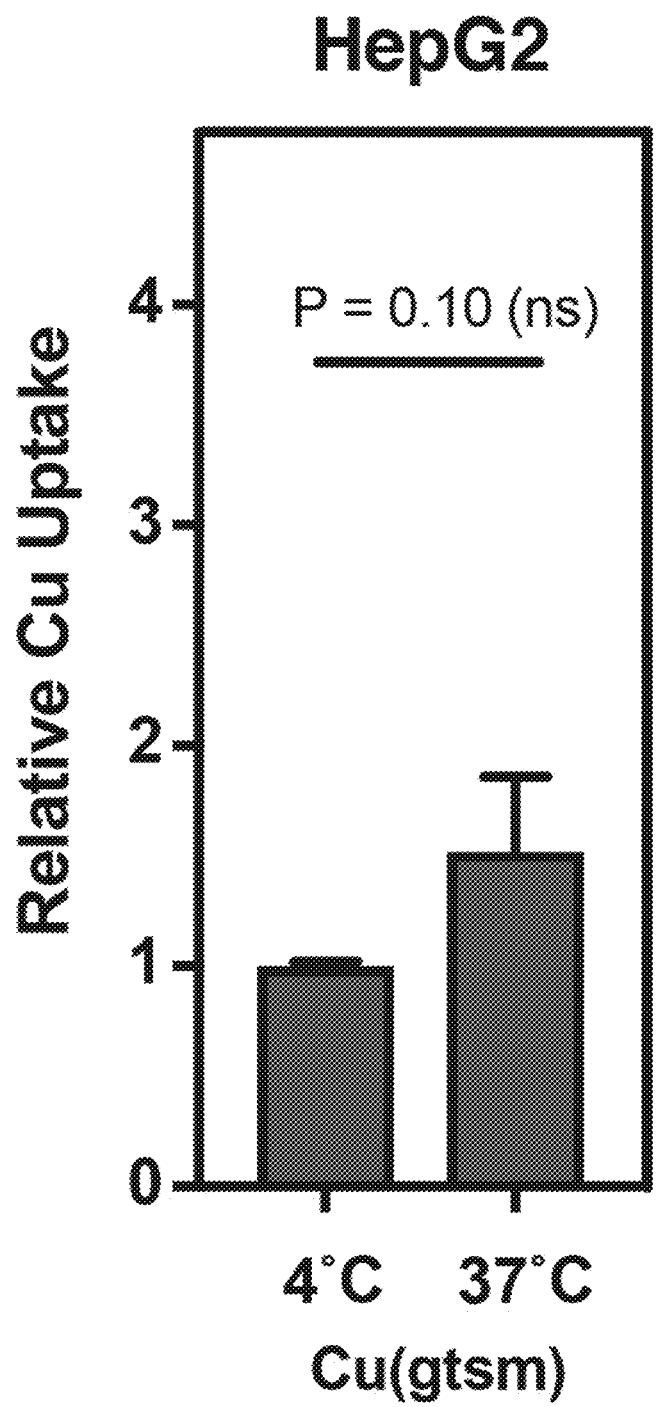
FIG. 6D shows copper supplementation by HepG2 cells at 4° C. or 37° C. that were treated with Cu(gtsm).
Figure 6E:
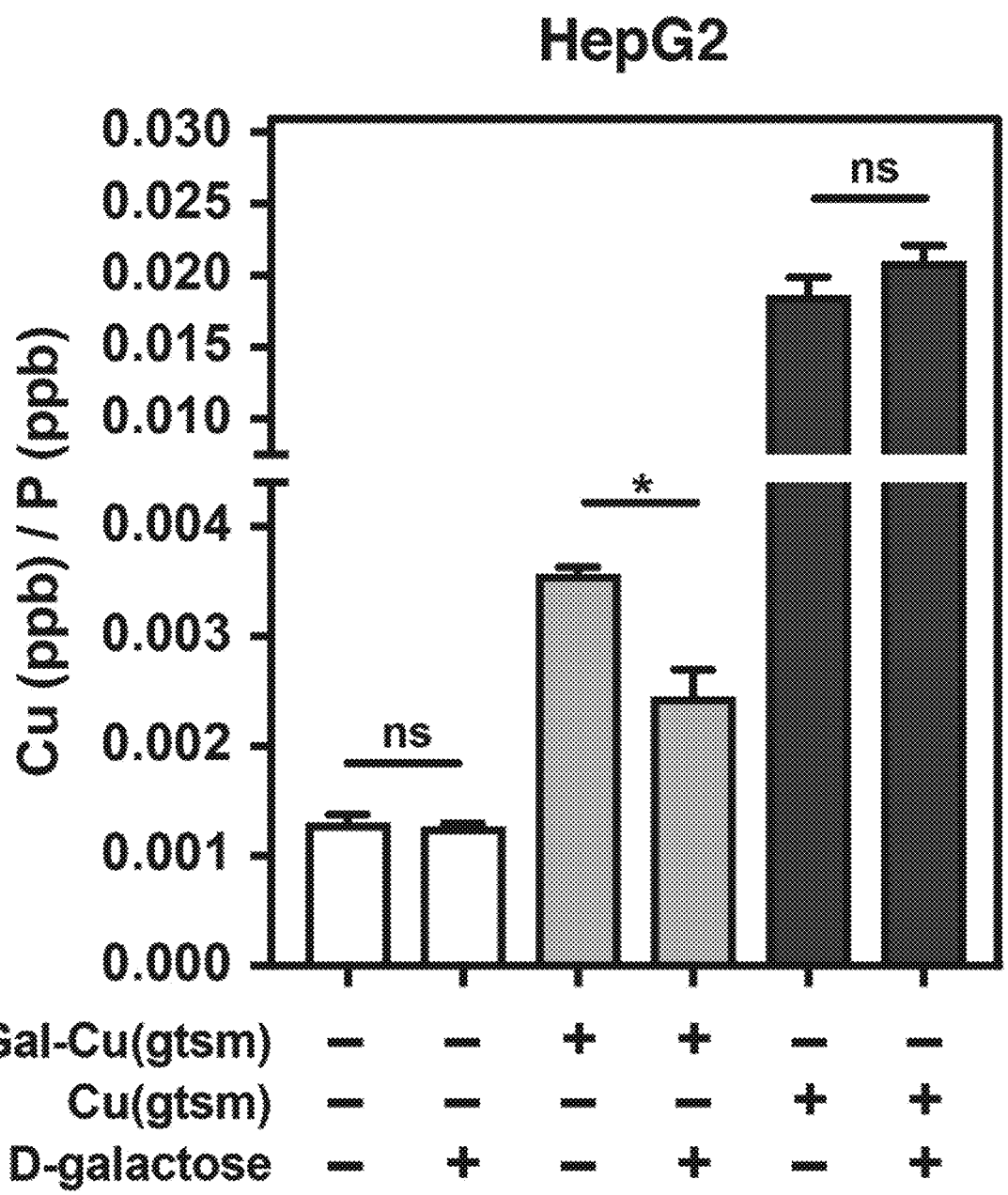
FIG. 6E shows copper supplementation by HepG2 cells treated with or without D-galactose (1 M in serum-free DMEM) as a competitive ASGPR ligand fifteen minutes prior to treatment with vehicle, Cu(gtsm) (4 µM), or Gal-Cu(gtsm) (20 µM) over a one-hour period.
Figure 7A:
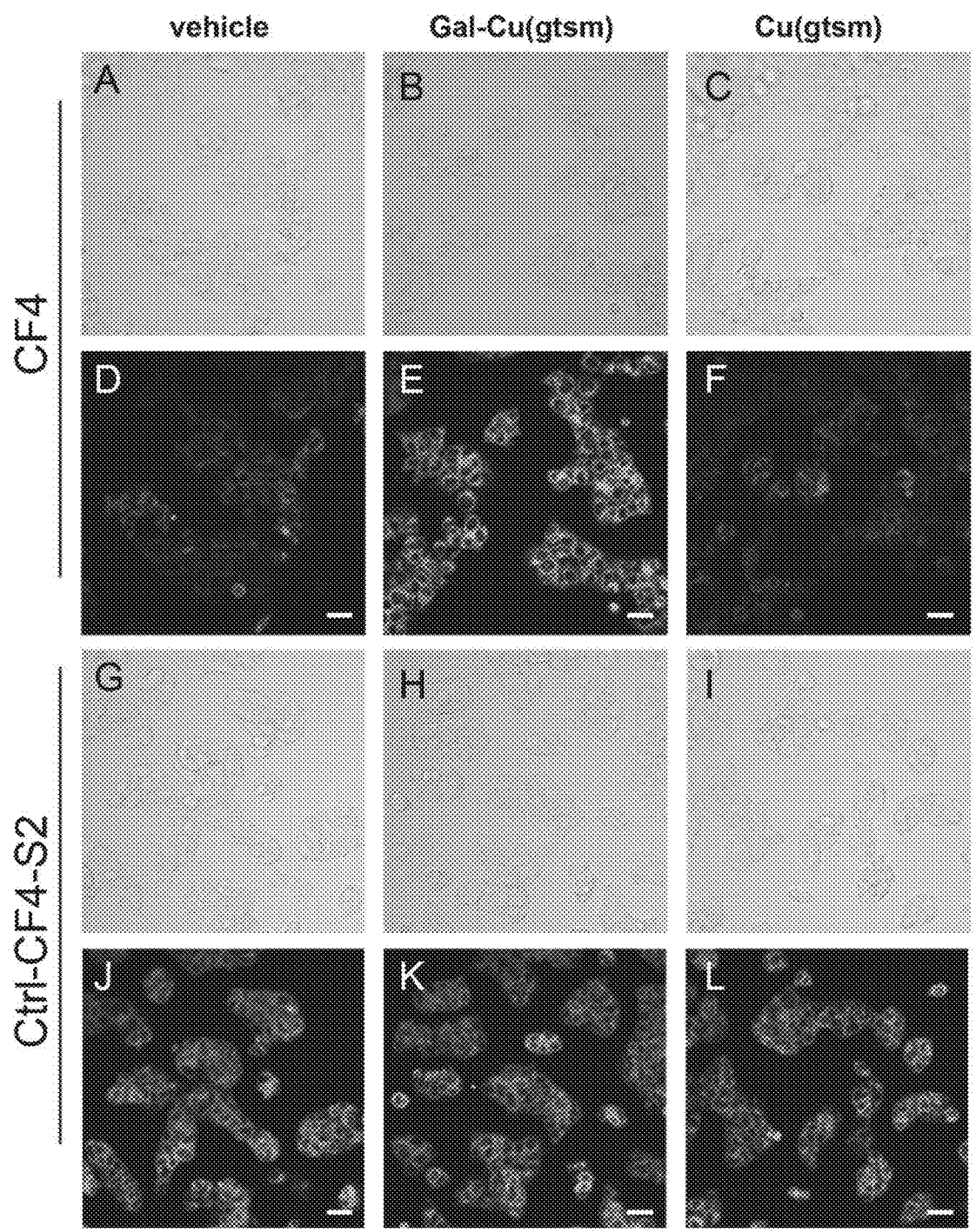
FIG. 7A shows confocal microscopy imaging with the copper sensing CF4 fluorophore and the copper insensitive Ctrl-CF4-S2 control fluorophore after the Hep2G cells were treated with vehicle, 100 µM Gal-Cu(gtsm), or 2 µM Cu(gtsm) in low glucose DMEM for 3 hours at 37° C., 5% $CO_2$. Panels A-C and G-I are bright-field images and panels D-F and J-L are fluorescent images.
Figure 7B:
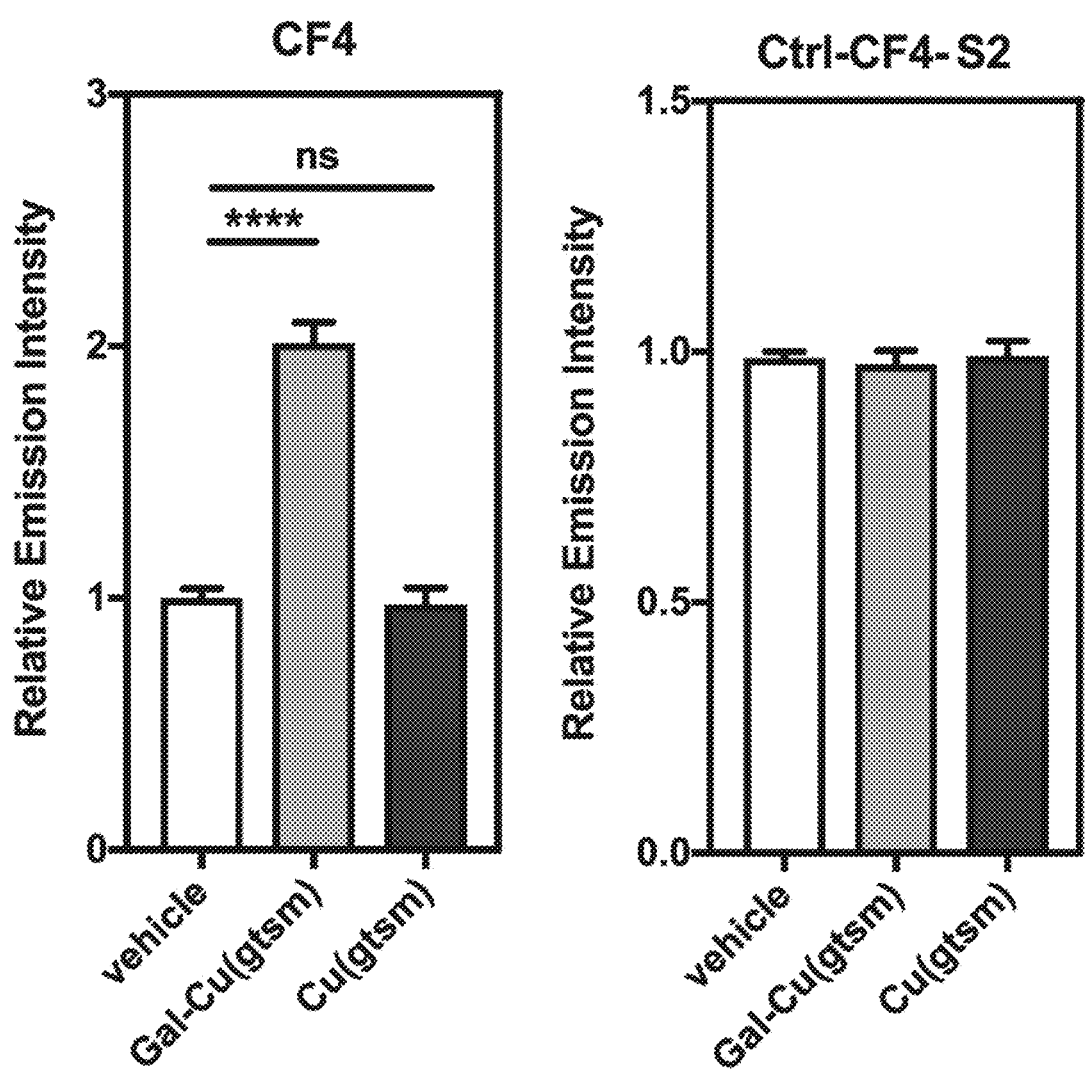
FIG. 7B shows emission intensity relative to vehicle control treatment for the CF4 (panel M) and Ctrl-CF4-S2 (panel N) treated cells described in FIG. 7A.
Figure 7C:
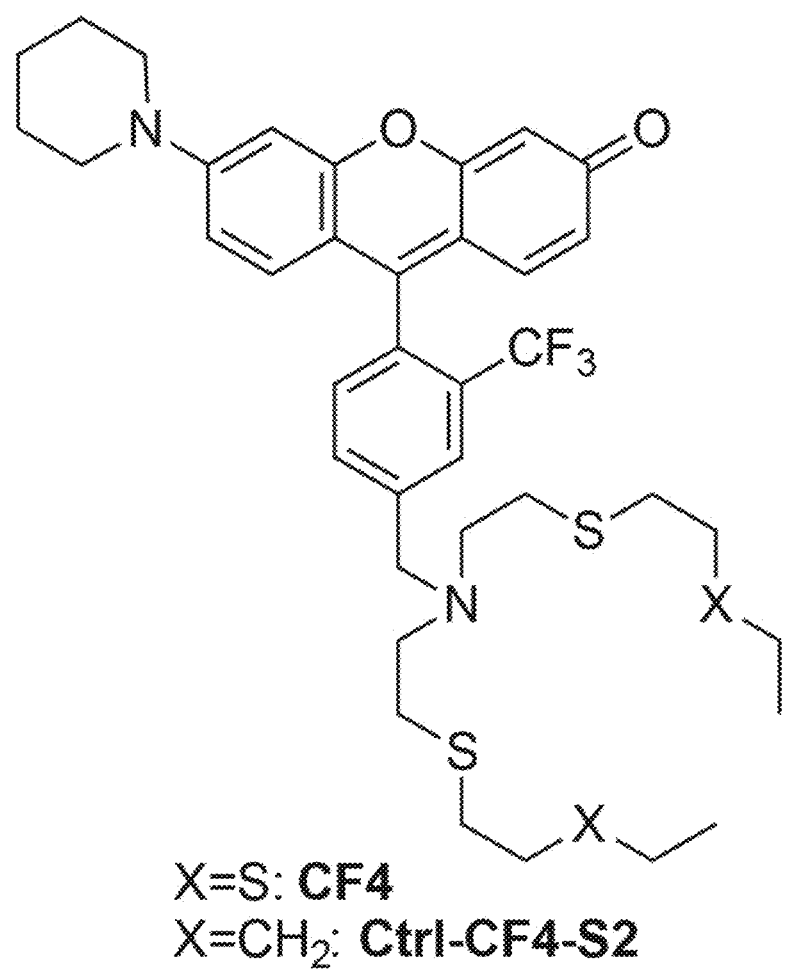
FIG. 7C shows the chemical structure of the CF4 and Ctrl-CF4-S2 fluorophores.

Temperature dependent uptake studies were performed at 4° C. and 37° C. Gal-Cu(gtsm) demonstrates much higher uptake at 37° C. than at 4° C. (FIG. 6C). In contrast, no significant differences in Cu delivery ability were observed for Cu(gtsm) between 4° C. and 37° C. (FIG. 6D). In addition, competition experiment were performed by treating HepG2 cells with vehicle control or ionophore in the presence of D-galactose (1 M) for one hour. The presence or absence of D-galactose did not alter Cu content upon vehicle or Cu(gtsm) treatment in HepG2 cells. It was found that Cu delivery via Gal-Cu(gtsm) is significantly attenuated in the presence of D-galactose (FIG. 6E). Confocal microscopy imaging was performed of HepG2 cells treated with Cu(gtsm) and Gal-Cu(gtsm) using the copper sensing CF4 fluorescent probe (Chang et al., J. Nat. Chem. Biol. 2018, 14, 655), increased fluorescence upon ionophore treatment (FIG. 7A-C).

Though the untargeted Cu(gtsm) ionophore delivered more total copper than Gal-Cu(gtsm) under equimolar doses to both HEK 293T and HepG2 cells, the salient finding for expanding the TIMS platform to animal studies was that copper delivery via Gal-Cu(gtsm) occurred exclusively in the ASGPR-expressing HepG2 cells.

Figure 8A:
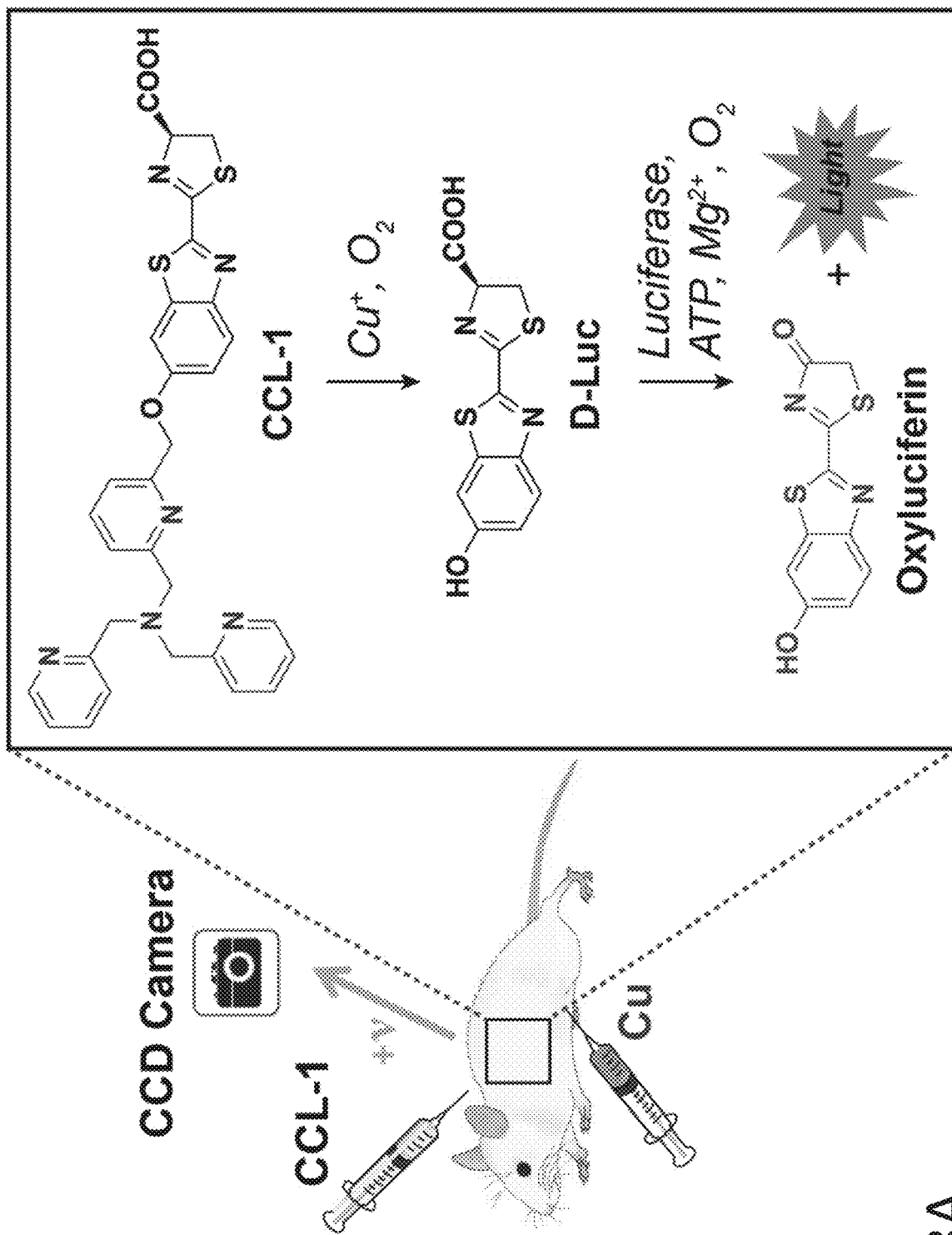
FIG. 8A is a schematic describing $Cu^+$-dependent cleavage of CCL-1 to give bioluminescent signal.
Figure 8B:
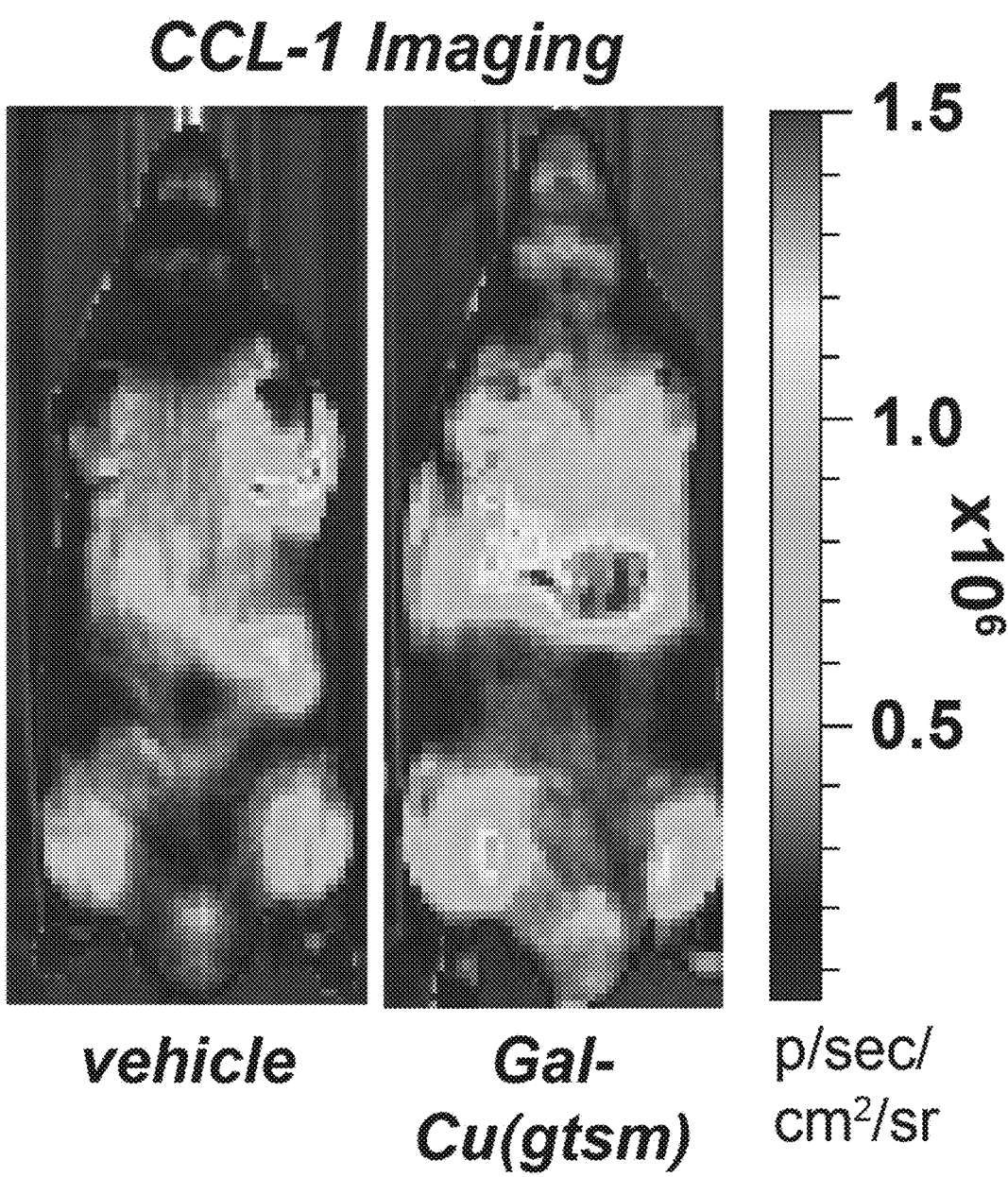
FIG. 8B shows representative images of mice injected s.c. with CCL-1 6 hours after vehicle or Gal-Cu(gtsm) i.p. administration.
Figure 9A:
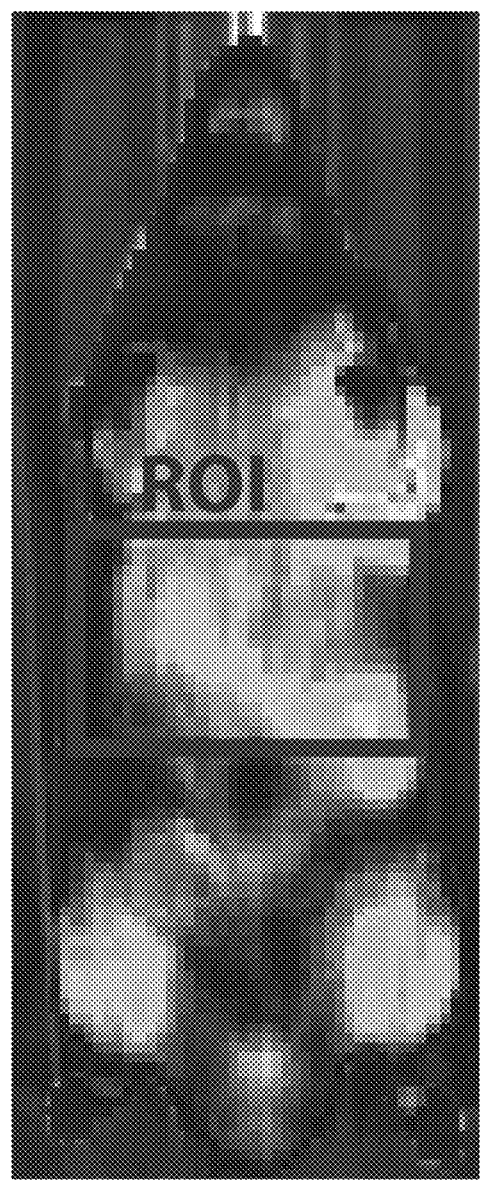
FIG. 9A shows bioluminescent imaging of a FVB-luc$^+$ mice 6 hours after ionophore treatment with vehicle via i.p. injection. After 6 hours, the mouse received s.c. injections of 0.1 µmol of CCL-1. A rectangular ROI was drawn around the liver, and the same-sized ROI was applied to each mouse image in the study.
Figure 9B:
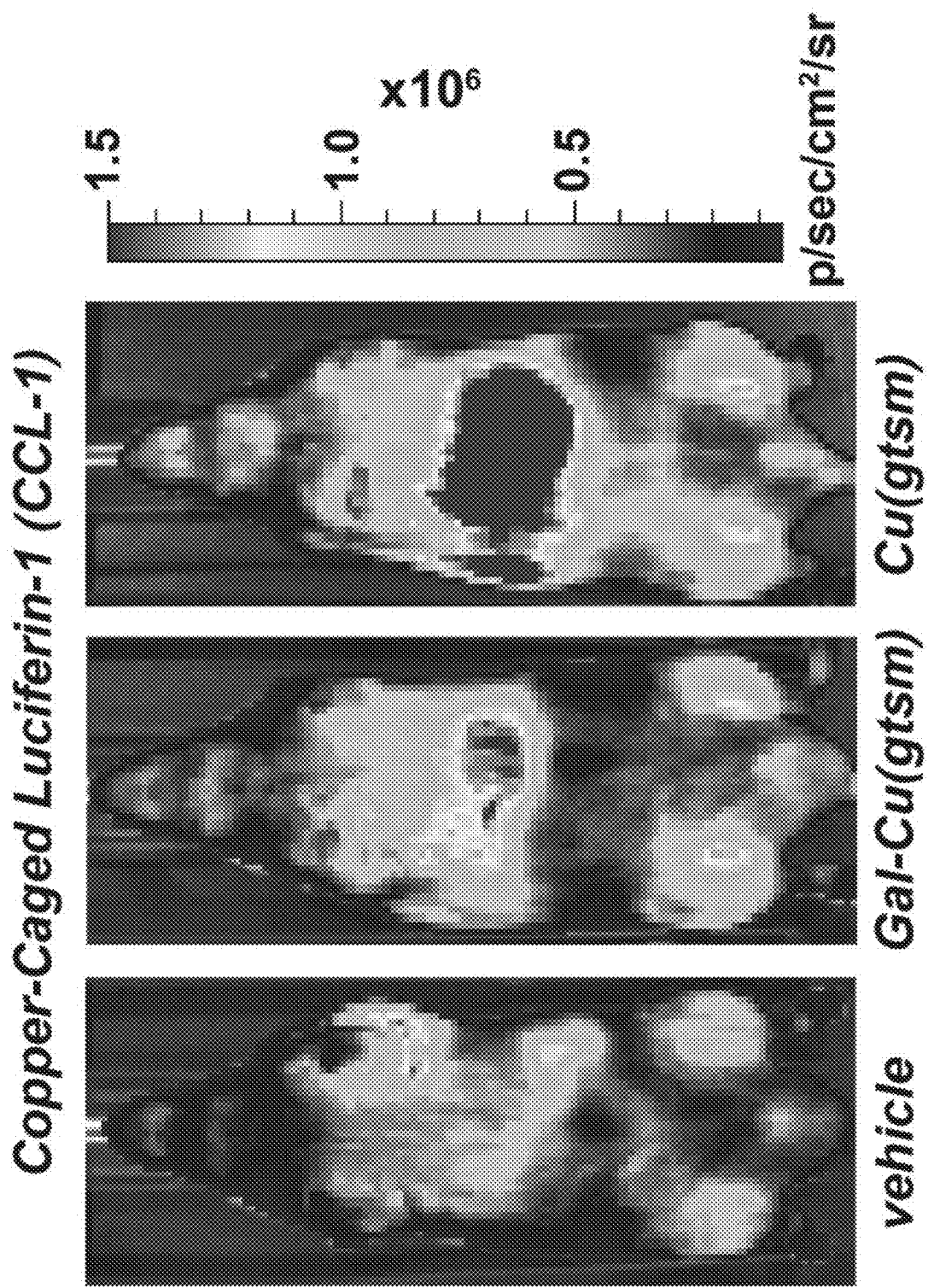
FIG. 9B shows representative bioluminescent images of FVB-luc$^+$ mice 6 hours after ionophore treatment with vehicle, Cu(gtsm), or Gal-Cu(gtsm) at 0.75 mg Cu/kg mouse via i.p. injection. After 6 hours, mice received s.c. injections of 0.1 µmol of CCL-1.
Figure 9C:
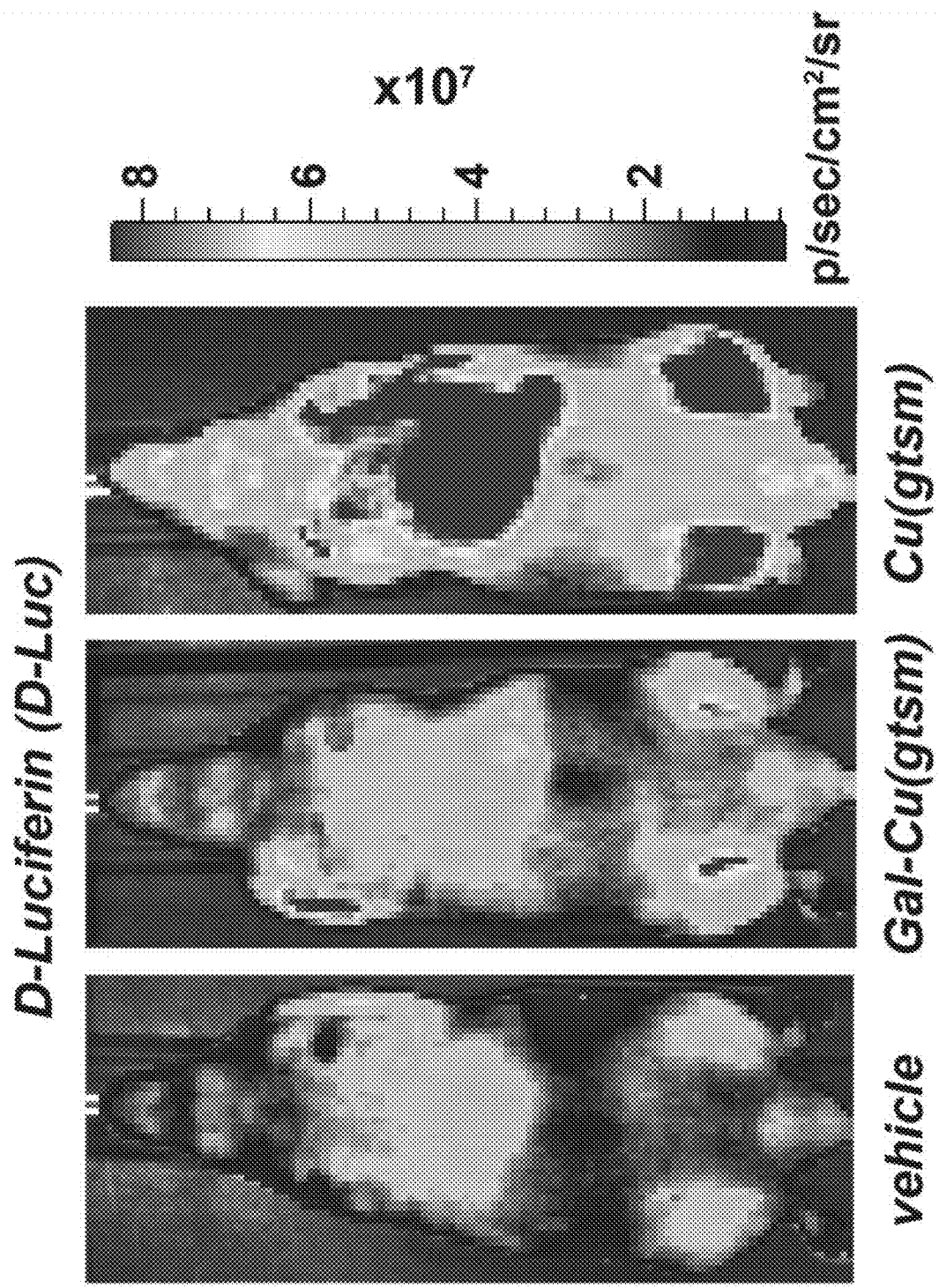
FIG. 9C shows representative bioluminescent images of FVB-luc$^+$ mice 6 hours after ionophore treatment with vehicle, Cu(gtsm), or Gal-Cu(gtsm) at 0.75 mg Cu/kg mouse via i.p. injection. After 6 hours, mice received s.c. injections of 0.1 µmol of D-Luc.

Example 3: Evaluating Liver Target Specificity of Copper Supplementation by Gal-Cu(gtsm) in Living Mice Experiments were performed to identify whether Gal-Cu(gtsm) could selectively provide Cu supplementation to the liver with minimal off-target delivery in the complex biological milieu of live mice. Liver-targeted copper supplementation in mice was chosen because they are known model organisms for elucidating the pathology of metabolic disorders such as NAFLD. A Copper Caged Luciferin-1 (CCL-1) probe that reports on dynamic changes to the loosely bound, labile $Cu^+$ pool in transgenic bioluminescent mice has been reported (FIG. 8A). See Heffern et al., Proc. Natl. Acad. Sci. 2016, 113, 14219. CCL-1 was used to characterize liver-directed copper supplementation in the firefly luciferase-expressing FVB-luc$^+$ mouse strain, where luciferase expression provides detection of changes in copper pools throughout the entire mouse. Ionophore-treated mice with D-luciferin (D-Luc) were imaged to normalize the CCL-1 signal and account for CCL-1 cleavage-independent bioluminescent effects. Male FVB-luc$^+$ mice (11-14 weeks old) received intraperitoneal (i.p.) injections of vehicle control, Gal-Cu(gtsm), or Cu(gtsm) at equivalent copper concentrations (0.75 mg Cu/kg mouse). This copper dose has been used to study the therapeutic effects of Cu(gtsm) and its derivatives (see Palanimuthu et al., J. Med. Chem. 2013, 56, 722; Bremer et al., J. Am. Chem. Soc. 2017, 139, 7264). After six hours, the same mice were anesthetized with isoflurane and given scapular subcutaneous (s.c.) injections of either CCL-1 or D-Luc (0.1 μmol) and imaged with an In Vivo Imaging System (IVIS) every 5 minutes over a 40-minute period. Representative images of CCL-1 injected mice six hours following vehicle or Gal-Cu(gtsm) treatment are provided in FIG. 8B. A full panel of images for CCL-1 and D-Luc injected mice both 6 and 24 hours after ionophore treatment is provided in FIGS. 9A, 9B, 9C, 10A, 10B.

Figure 11:
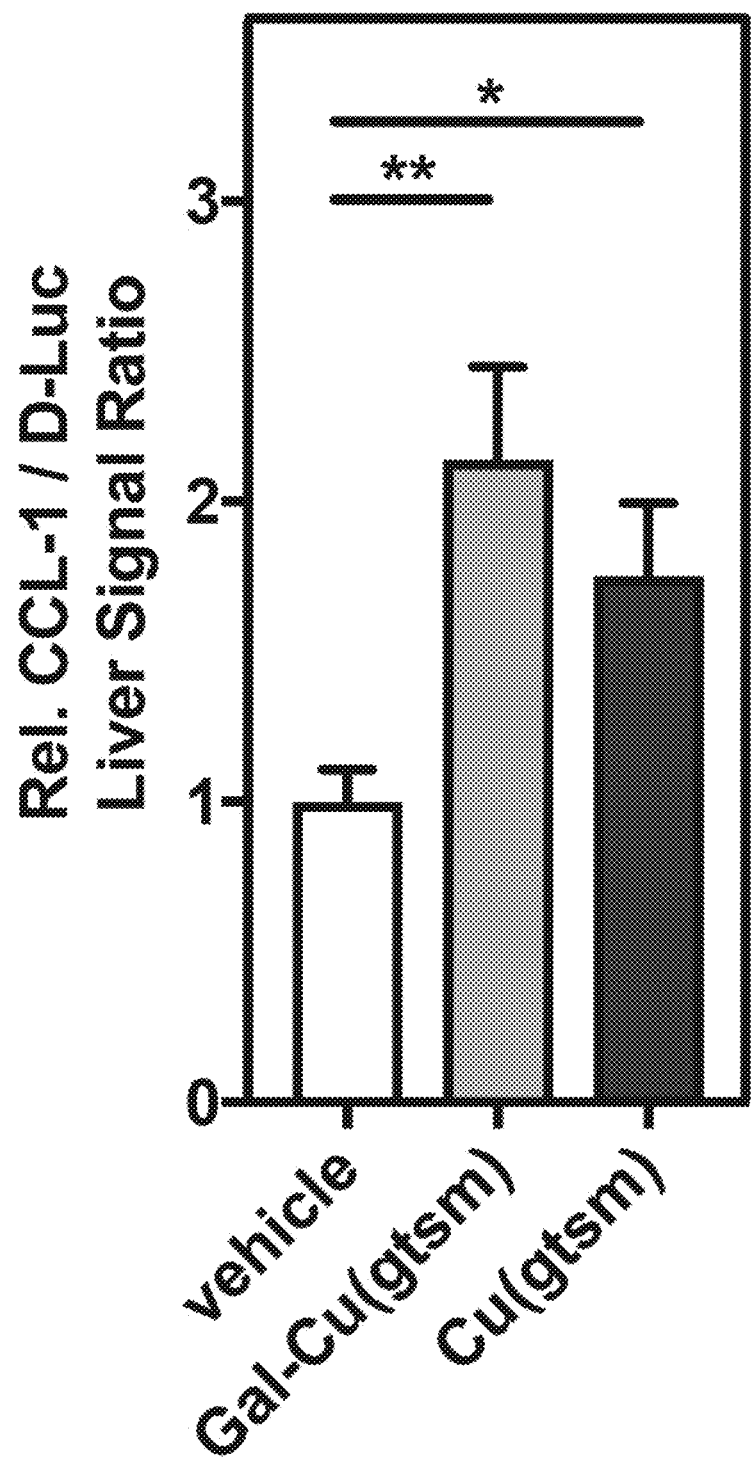
FIG. 11 shows CCL-1 total integrated photon flux as a ratio over D-Luc total integrated photon flux
Figure 12:
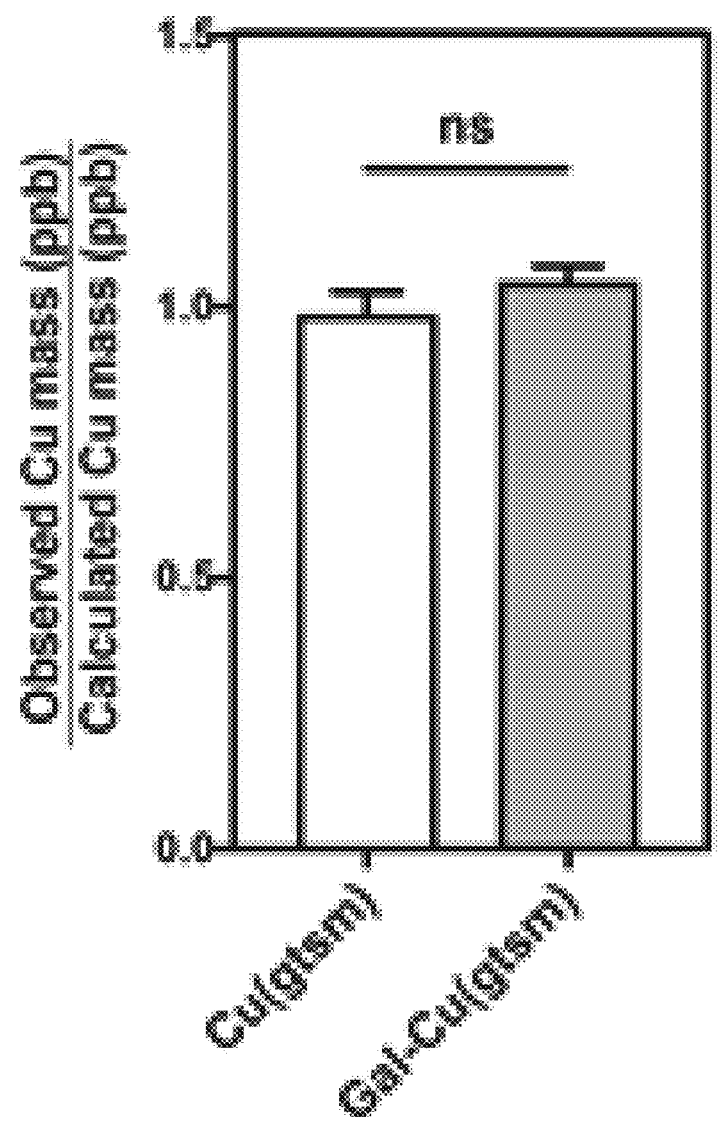
FIG. 12 shows ICP-MS analysis of DMSO stock solutions of Cu(gtsm) and Gal-Cu(gtsm). Ionophore solutions in 1:1 DMSO:DPBS were digested at a calculated Cu concentration of 20 ppb. Data plotted as observed Cu mass divided by calculated Cu mass.
Figure 13:
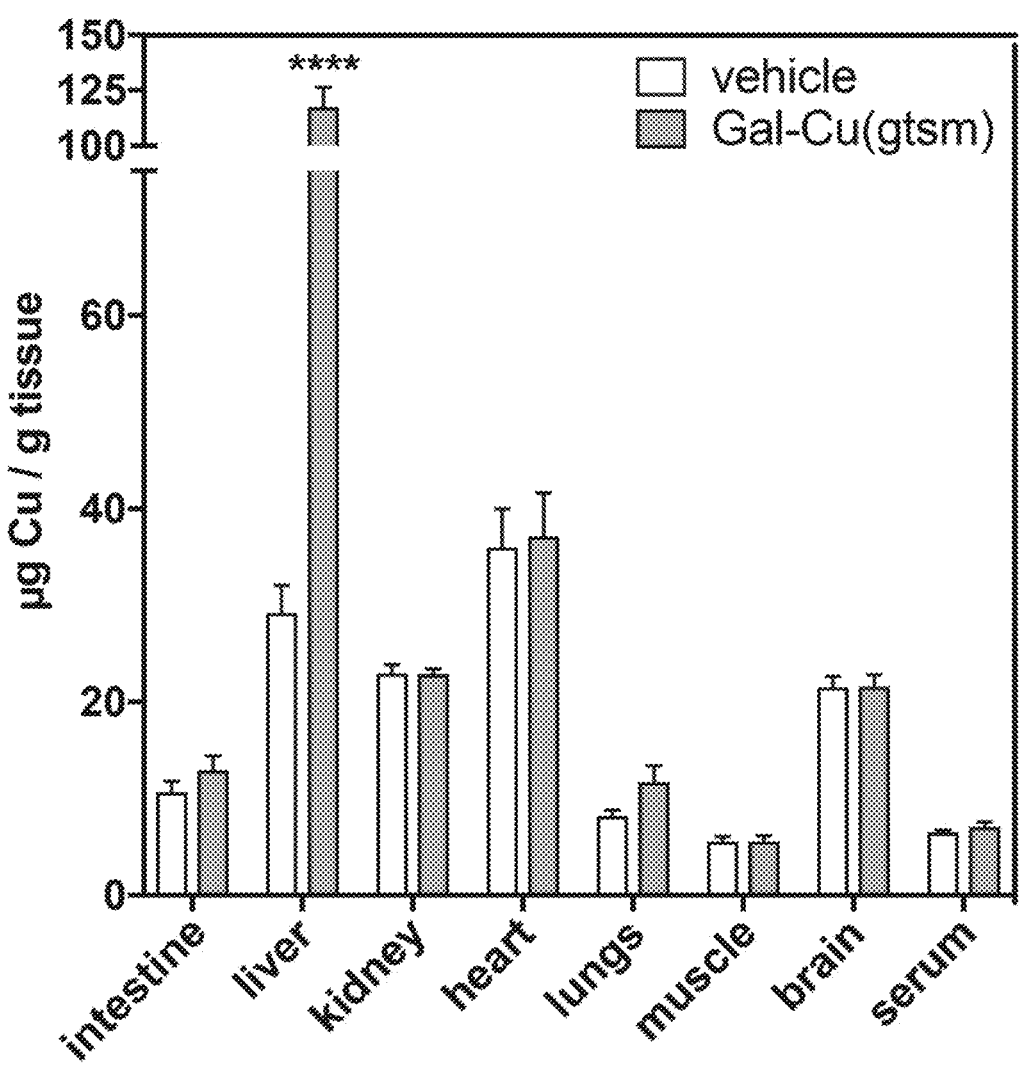
FIG. 13 shows copper supplementation in mice that were injected i.p. with 0.75 mg equivalent Cu/kg mouse of Gal-Cu(gtsm).
Figure 14:
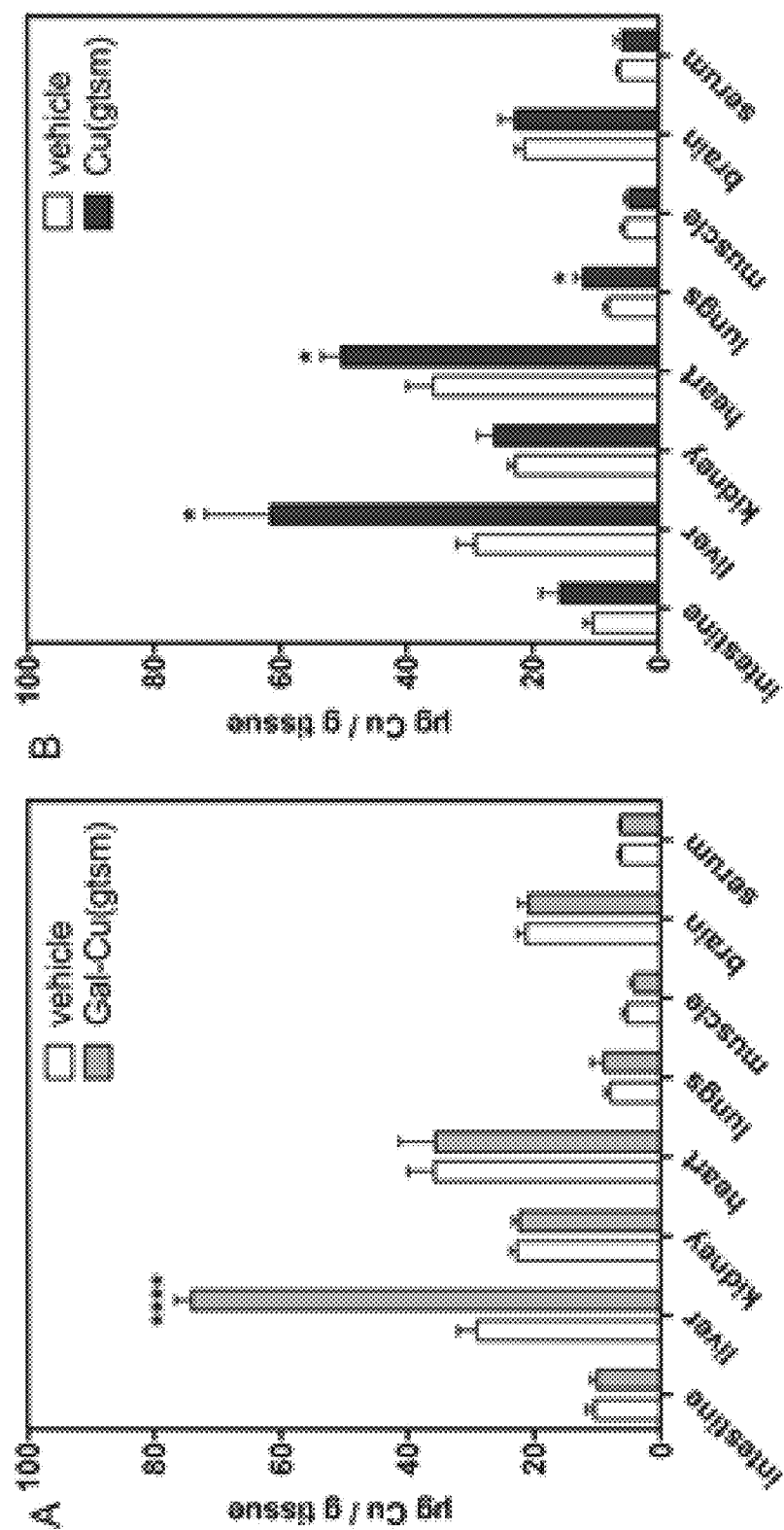
FIG. 14 shows ICP-MS analysis of tissue copper content in FVB-luc⁺ mice 24 hours following ionophore treatment. Mice were injected i.p. with 0.75 mg equivalent Cu/kg mouse of Gal-Cu(gtsm) or Cu(gtsm) 24 hours prior to blood and tissue collection.
Figure 15:
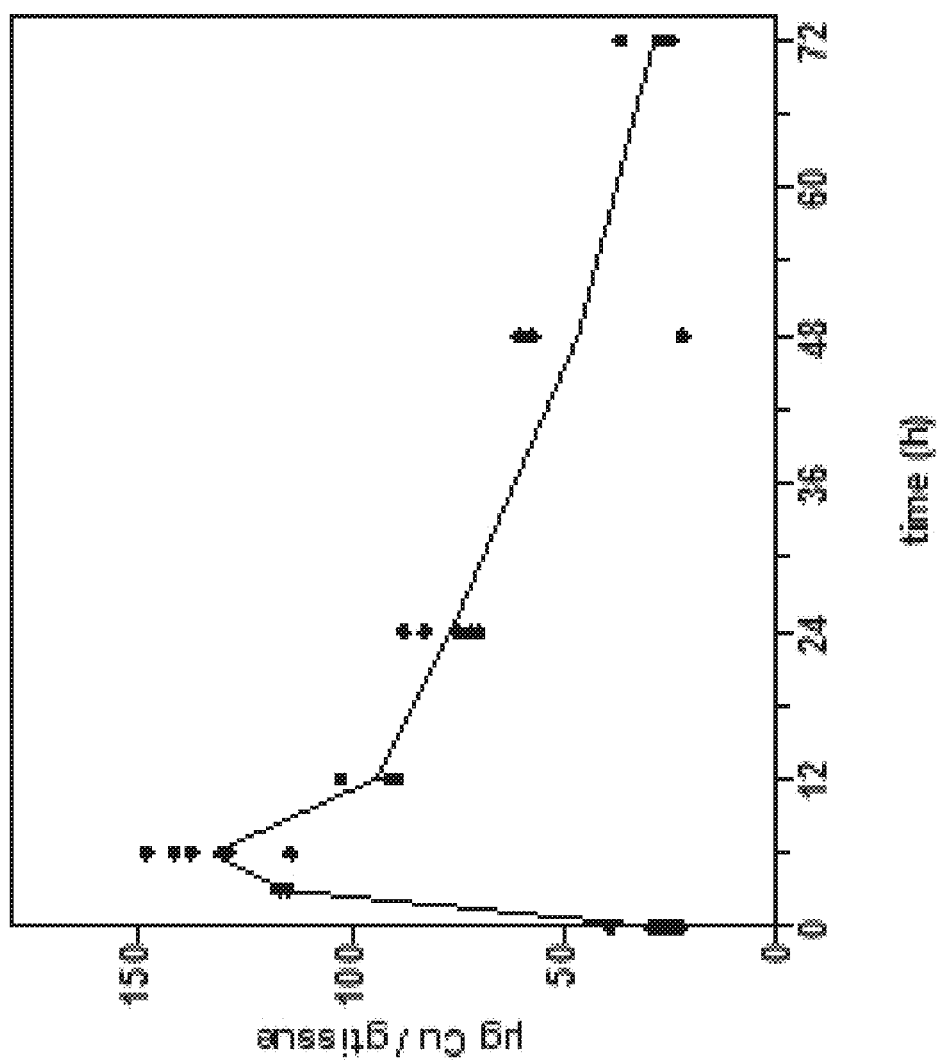
FIG. 15 shows ICP-MS clearance studies of hepatic copper stores supplemented via Gal-Cu(gtsm). Mice were injected i.p. at 0.75 mg Cu/kg mouse in 1:1 DMSO:DPBS (9.4 mM solution). Livers were harvested at indicated timepoint.

FIG. 11 plots the ratio of CCL-1/D-Luc integrated photon fluxes in the liver region, six hours after ionophore supplementation. High increases in liver CCL-1/D-Luc signal ratio responses were observed The greater propensity for off-target copper accumulation with Cu(gtsm) is supported by ex vivo tissue metal analysis via ICP-MS to evaluate total copper levels across organs after Cu(gtsm) and Gal-Cu(gtsm) supplementation at a 0.75 mg Cu/kg dose. First, ICP-MS analysis was performed on the stock solutions of Cu(gtsm) and Gal-Cu(gtsm) to confirm that equivalent copper doses between the ionophores were administered (FIG. 12). Blood and harvested organs were collected at two different timepoints (6 hours, 24 hours) to study the time-dependence of copper content and distribution across organs, then processed tissues for ICP-MS analysis. Gal-Cu(gtsm) supplementation results in a 300% increase in liver copper levels after 6 hours, with no significant differences in Cu levels in the other extracted organs compared to basal conditions (FIG. 13). Half of this copper is excreted 24 hours following Gal-Cu(gtsm) supplementation, with a 150% increase in liver copper relative to basal levels. Copper levels in serum and other organs remains at basal levels at 24 hours (FIG. 14), implying that the supplemented hepatic copper pool is not re-distributed from the liver to other organs over time. It was found that hepatic copper stores are cleared to basal levels after 72 hours (FIG. 15).

Figure 10A:
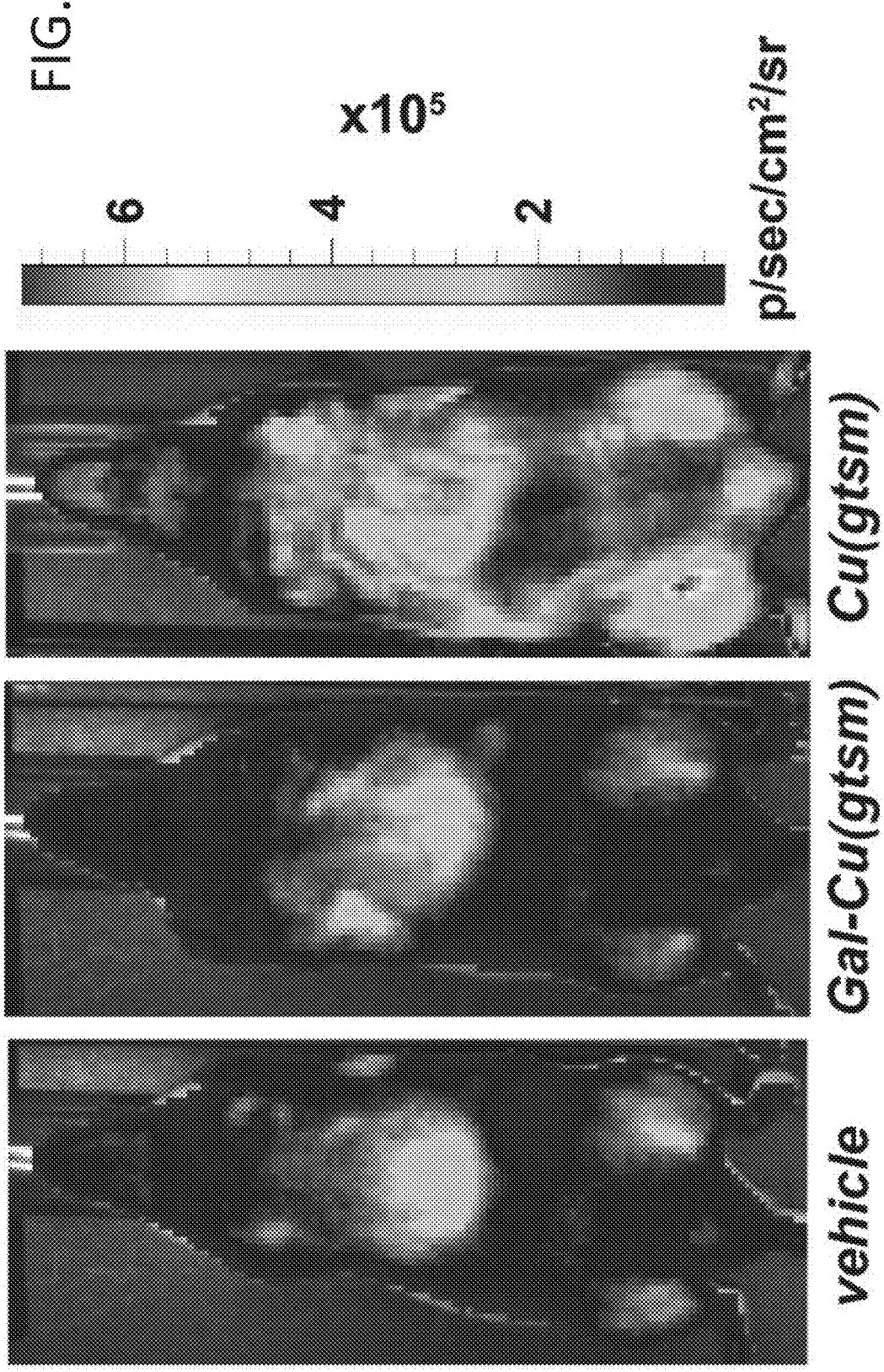
FIG. 10A shows representative bioluminescent images of FVB-luc$^+$ mice 24 hours after ionophore treatment with vehicle, Cu(gtsm), or Gal-Cu(gtsm) at 0.75 mg Cu/kg mouse via i.p. injection. After 24 hours, mice received s.c. injections of 0.1 µmol of CCL-1.
Figure 10B:
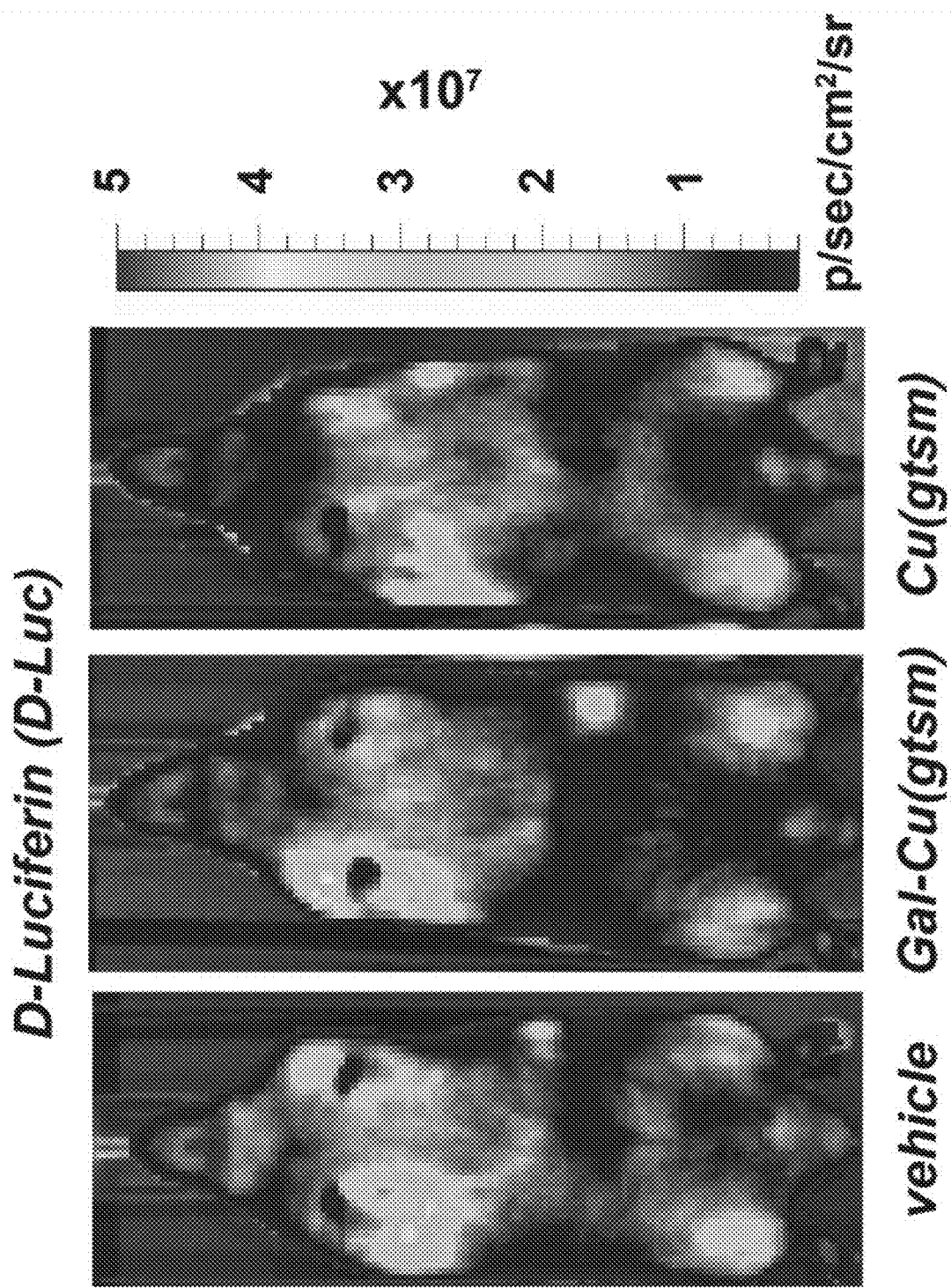
FIG. 10B shows representative bioluminescent images of FVB-luc⁺ mice 24 hours after ionophore treatment with vehicle, Cu(gtsm), or Gal-Cu(gtsm) at 0.75 mg Cu/kg mouse via i.p. injection. After 24 hours, mice received s.c. injections of 0.1 μmol of D-Luc.
Figure 10C:
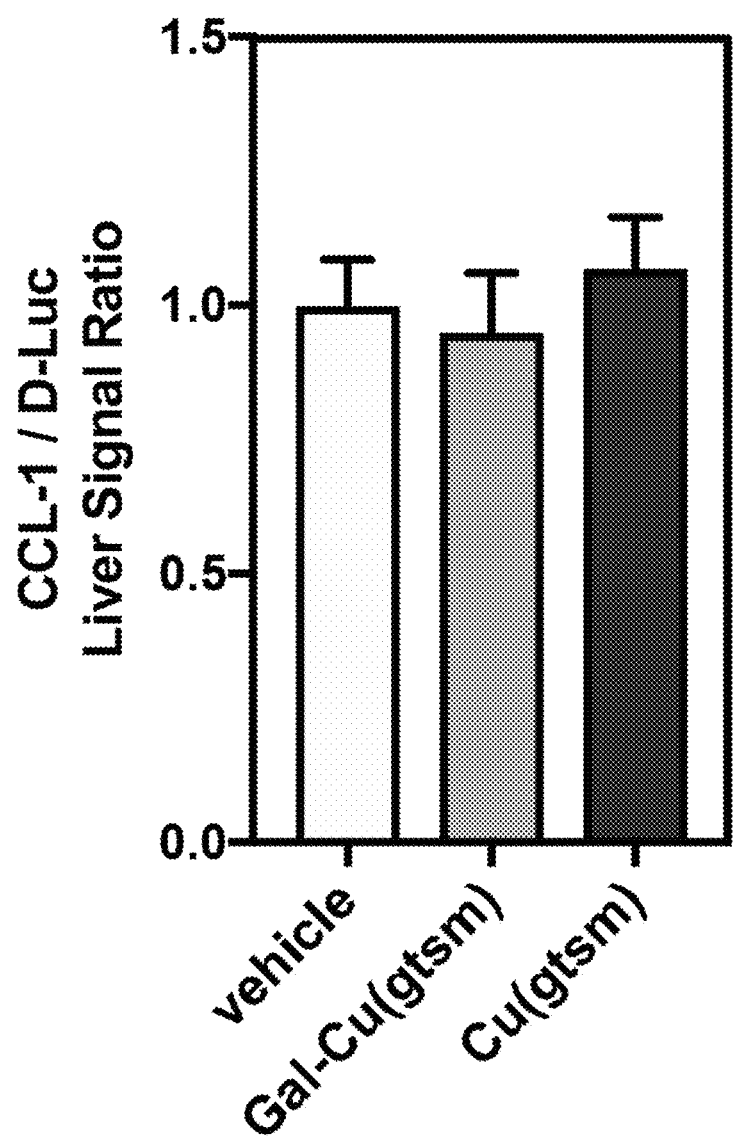
FIG. 10C shows plots of the data collected in the experiments shown in FIGS. 9A, 9B, 9C, 10A, and 10B, represents CCL-1 total integrated photon flux as a ratio over D-Luc total integrated photon flux. Total integrated photon flux was collected 5-45 minutes post injection in a region of interest drawn over the liver. Liver signal ratio is normalized to vehicle control. Error bars=SEM (n=3-4).
Figure 16:
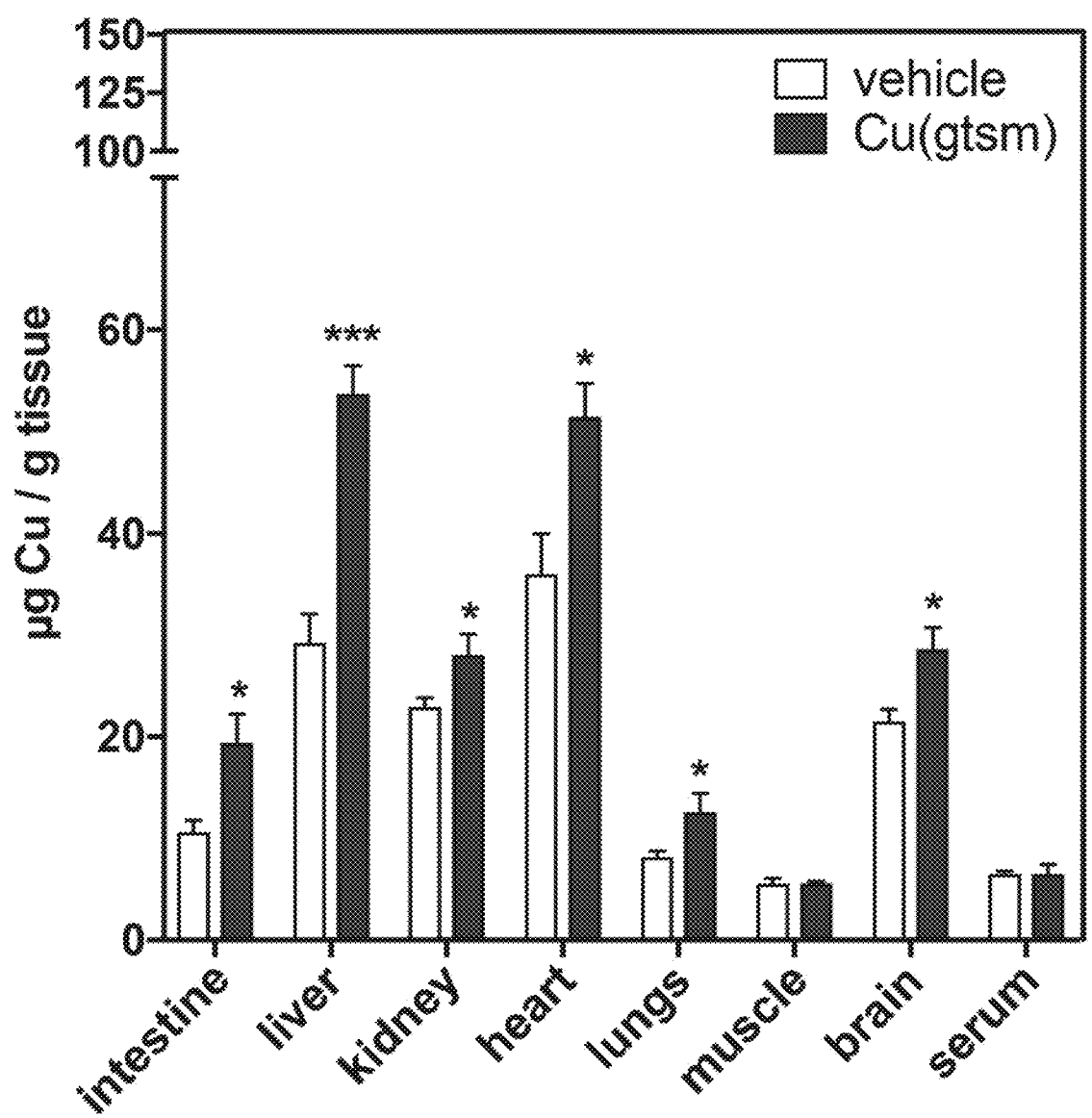
FIG. 16 shows copper supplementation in mice that were injected i.p. with 0.75 mg equivalent Cu/kg mouse of Cu(gtsm).
Figure 17A:
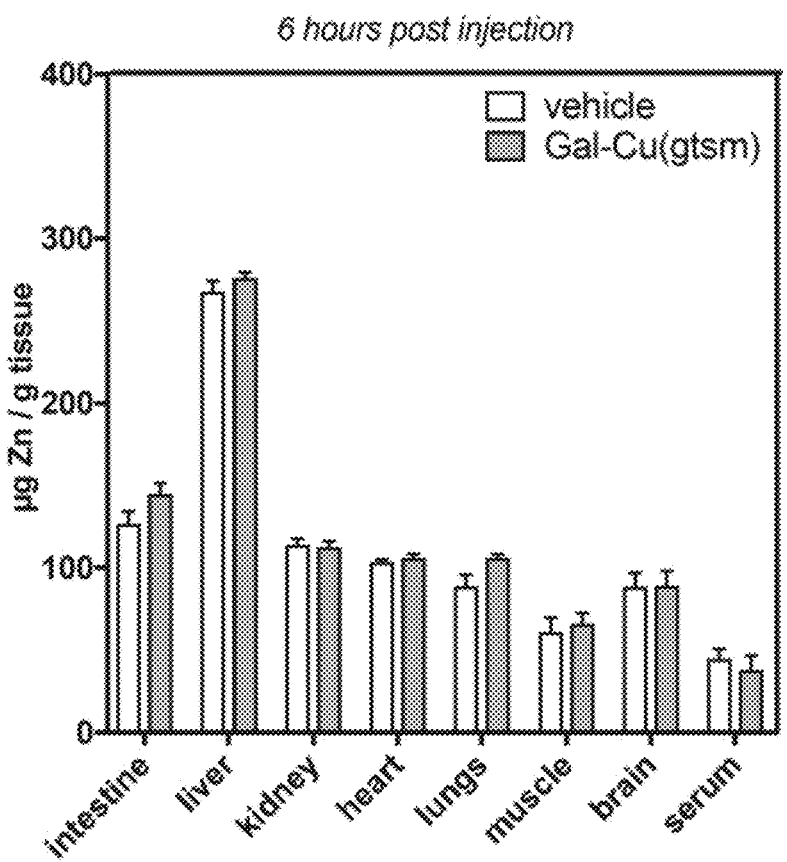
FIG. 17A shows ICP-MS analysis of tissue zinc content in FVB-luc⁺ mice 6 hours and 24 hours following Cu(gtsm) treatment. Error bars=SEM (n=5).
Figure 17A:
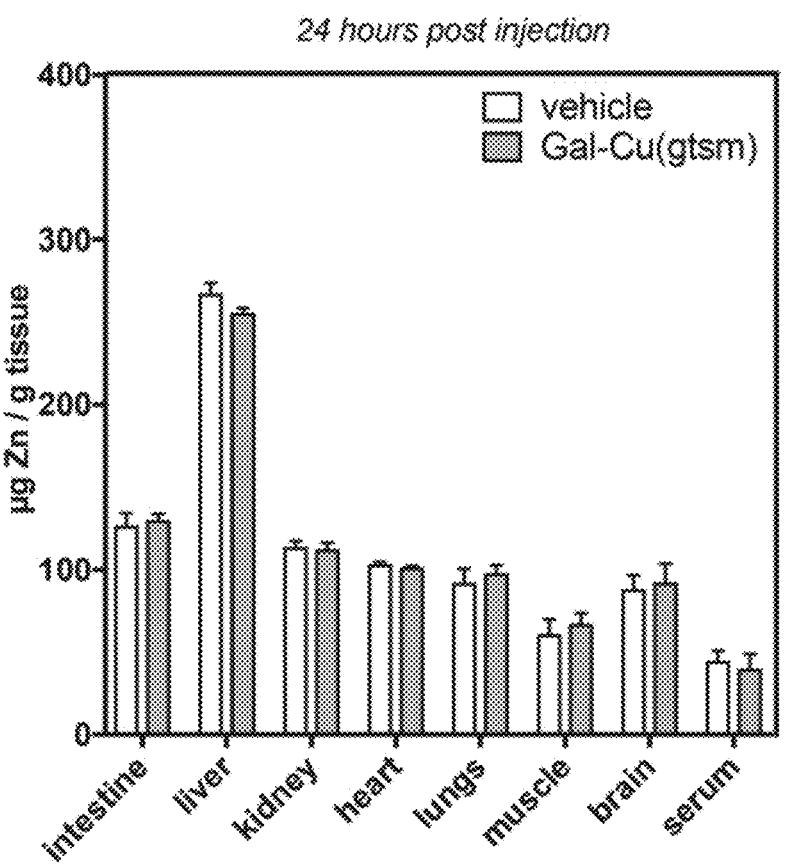
Figure 17B:
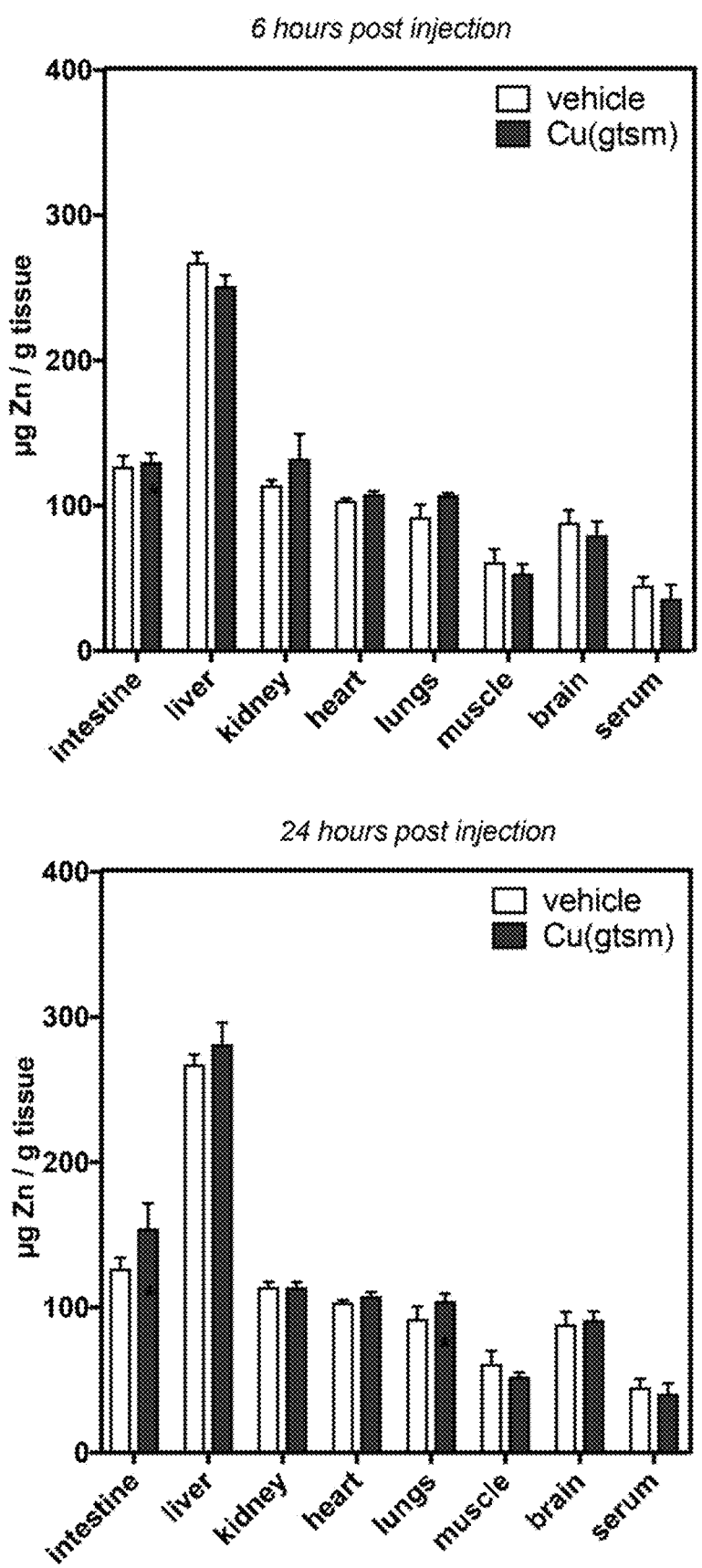
FIG. 17B shows ICP-MS analysis of tissue zinc content in FVB-luc⁺ mice 6 hours and 24 hours following Gal-Cu (gtsm) treatment. Error bars=SEM (n=5).
Figure 18A:
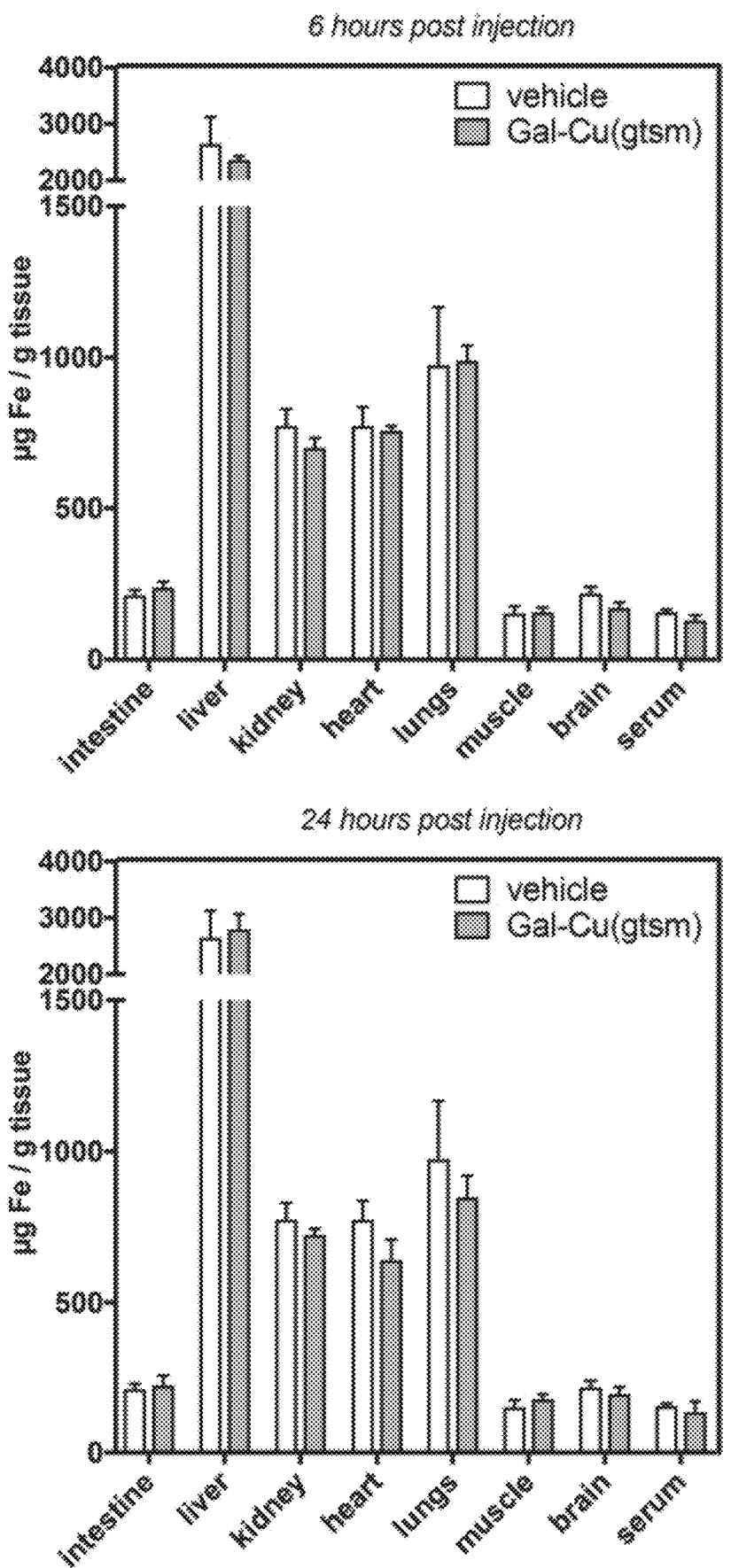
FIG. 18A shows ICP-MS analysis of tissue iron content from FVB-luc⁺ mice 6 hours and 24 hours following treatment with Cu(gtsm). Error bars=SEM (n=5).
Figure 18B:
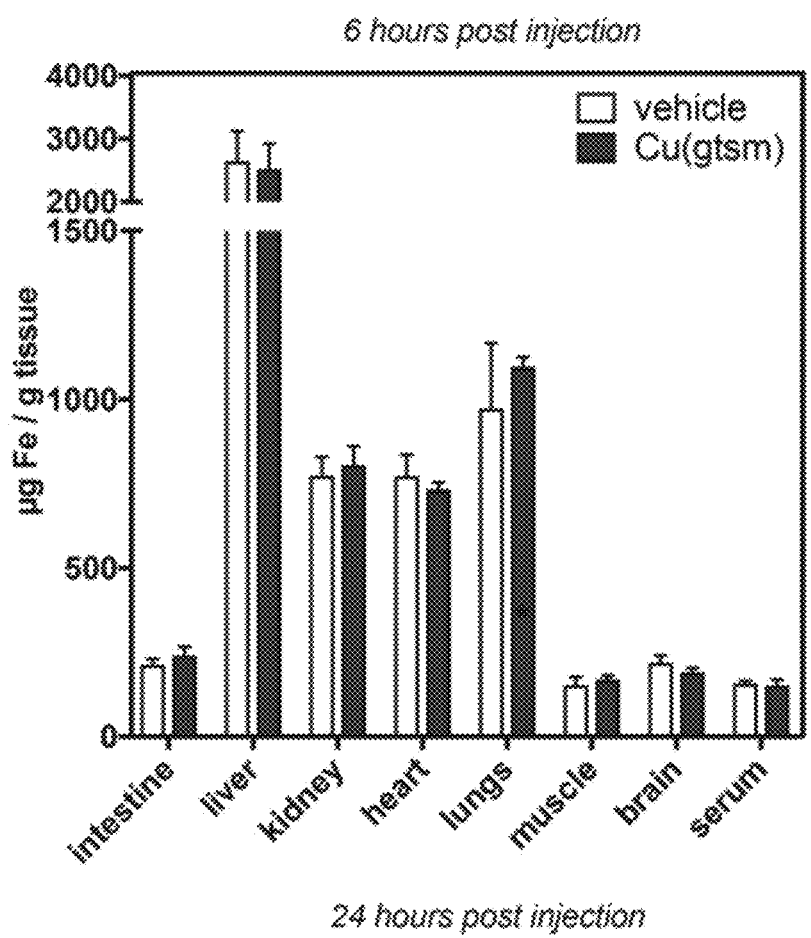
FIG. 18B shows ICP-MS analysis of tissue iron content from FVB-luc⁺ mice 6 hours and 24 hours following treatment with Gal-Cu(gtsm). Error bars=SEM (n=5).
Figure 18B:
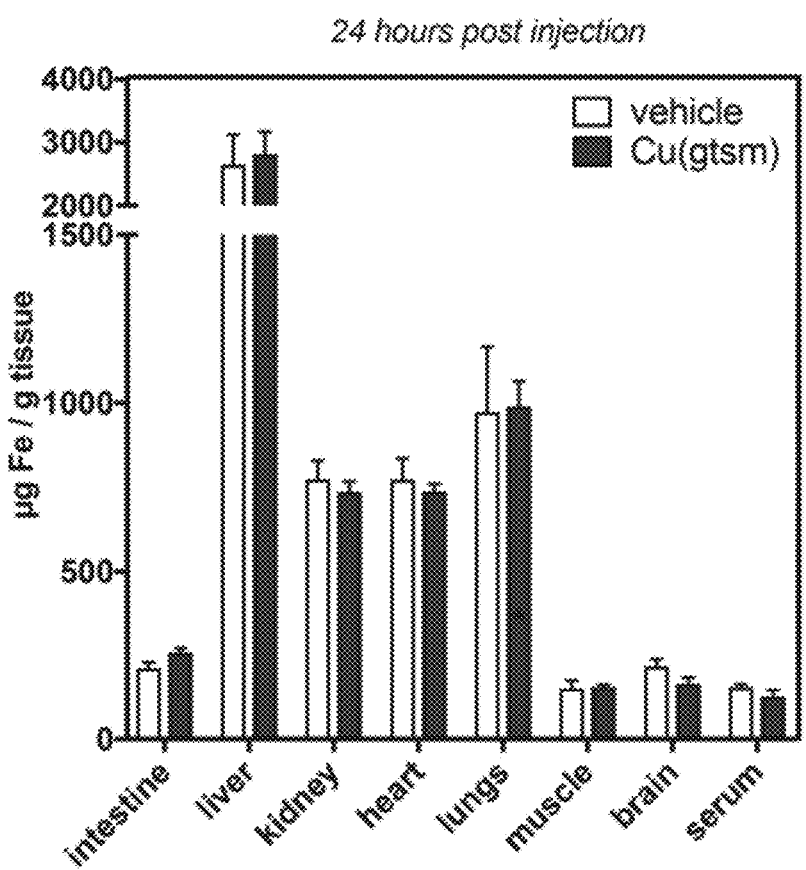

In contrast, untargeted Cu(gtsm) ionophore treatment leads to a 90% increase in liver copper content at the 6-hour timepoint (FIG. 16), with substantial off-target copper delivery to organs including the intestines, kidney, heart, lungs, and brain. At 24 hours, there remains a statistically significant increase in liver, heart, and lung copper relative to basal levels (FIG. 14). Although total hepatic copper levels remain substantially elevated at 24 hours for both Gal-Cu(gtsm) and Cu(gtsm), it was found that the bioluminescent CCL-1/D-luc liver signal returns to basal levels after 24 hours (FIGS. 10A-B). Furthermore, it was found that the administration of Gal-Cu(gtsm) or Cu(gtsm) offers minimal perturbation to iron and zinc levels across tissues relative to basal conditions (FIGS. 17A-B, 18A-B). These data indicate that appending a N-acetylgalactosamine moiety to the Cu(gtsm) framework can provide copper supplementation selectively to the liver in whole animal settings, likely through an ASGPR-mediated pathway.

Figure 19:
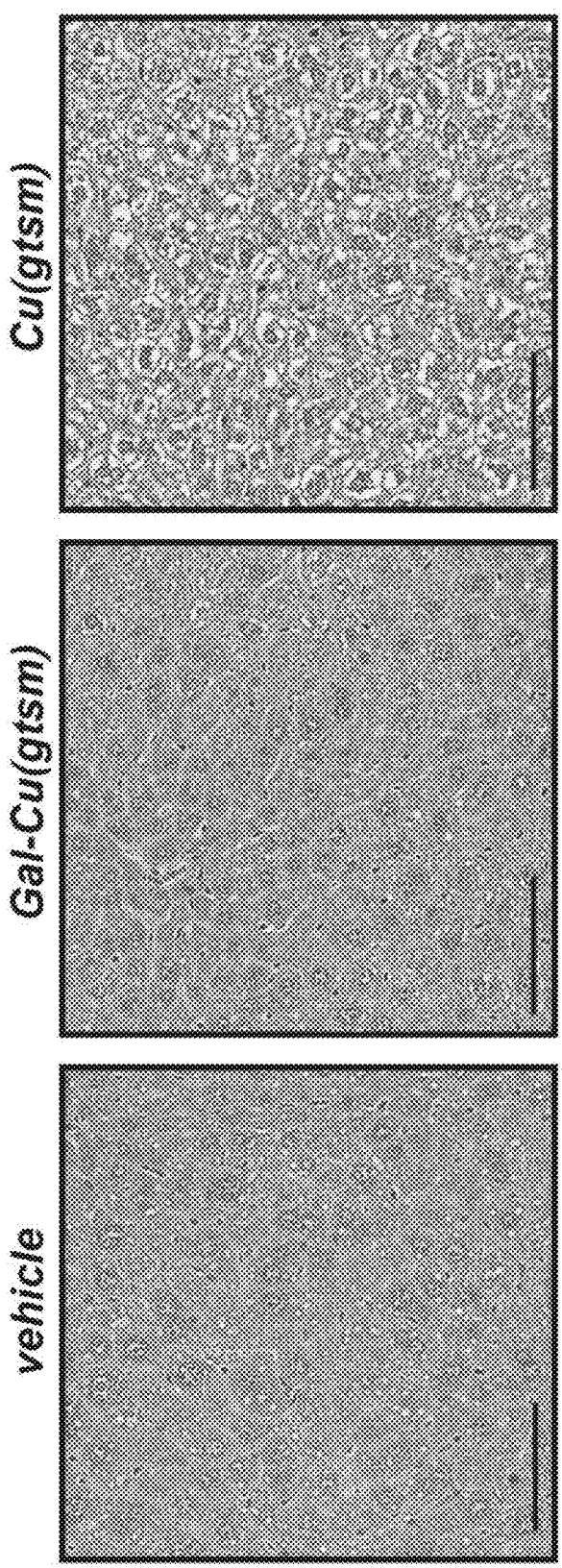
FIG. 19 shows Representative liver tissue slices from H&E staining show significant hydropic degeneration (wispy/white cytosolic areas surrounding nuclei) upon Cu(gtsm) treatment.

Example 4: Evaluating Toxicity Differences Between Targeted Gal-Cu(gtsm) and Untargeted Cu(gtsm) Supplements Although Gal-Cu(gtsm) delivers ca. 4 times more hepatic copper than Cu(gtsm) at an equivalent dose, it was found that Gal-Cu(gtsm) treatment is non-toxic while Cu(gtsm) treatment incurs significant hepatocellular injury as indicated by liver histology and toxicity assays. Indeed, hematoxylin & eosin (H&E) staining on liver tissue slices harvested from mice 6 hours after ionophore treatment at 0.75 mg Cu/kg mouse (FIG. 19) show that Gal-Cu(gtsm)-treated liver slices largely resemble those of the vehicle-treated control mice, whereas H&E histology reveals significant hepatocellular damage upon Cu(gtsm) supplementation, with features characteristic of hydropic degeneration that occurs upon acute liver injury (FIG. 19). See e.g., Zachary, J. F. Pathologic Basis of Veterinary Disease; 6th ed.; Elsevier: St Louis, Mo., 2017.

Figure 20:
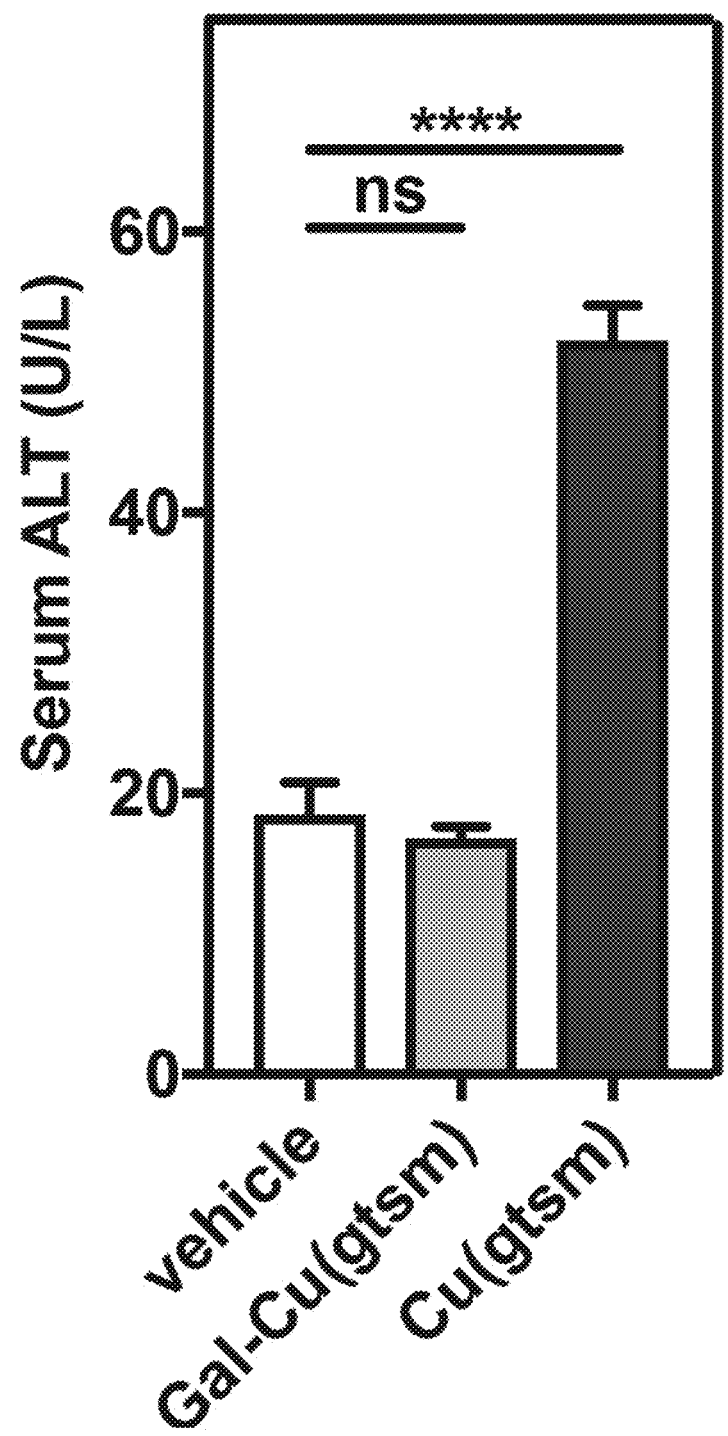
FIG. 20 shows results of an alanine transaminase (ALT) assay performed on serum after treatment with Cu(gtsm) or Gal-Cu(gtsm).
Figure 21:
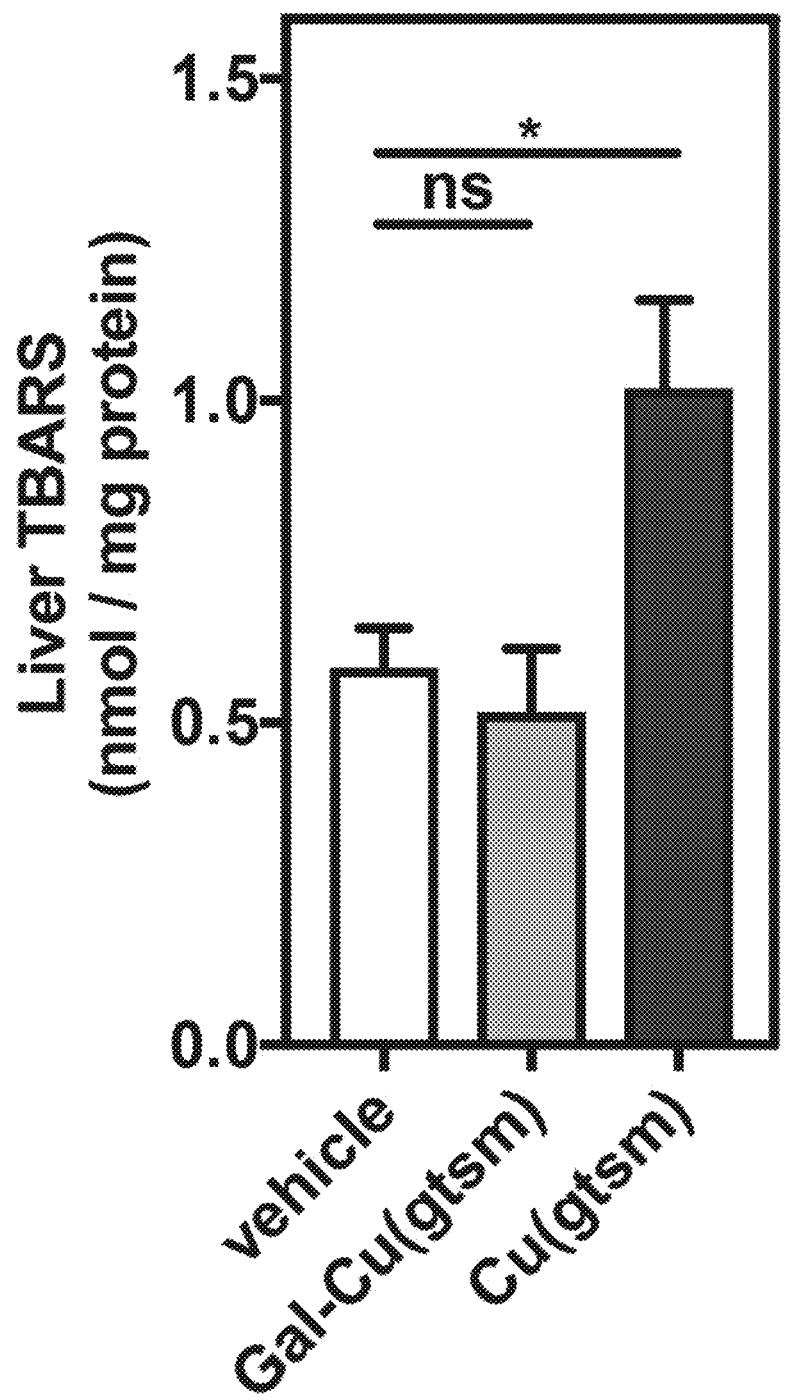
FIG. 21 shows results of a thiobarbituric acid reactive substances (TBARS) assays on liver lysate after treatment with Cu(gtsm) or Gal-Cu(gtsm).
Figure 22:
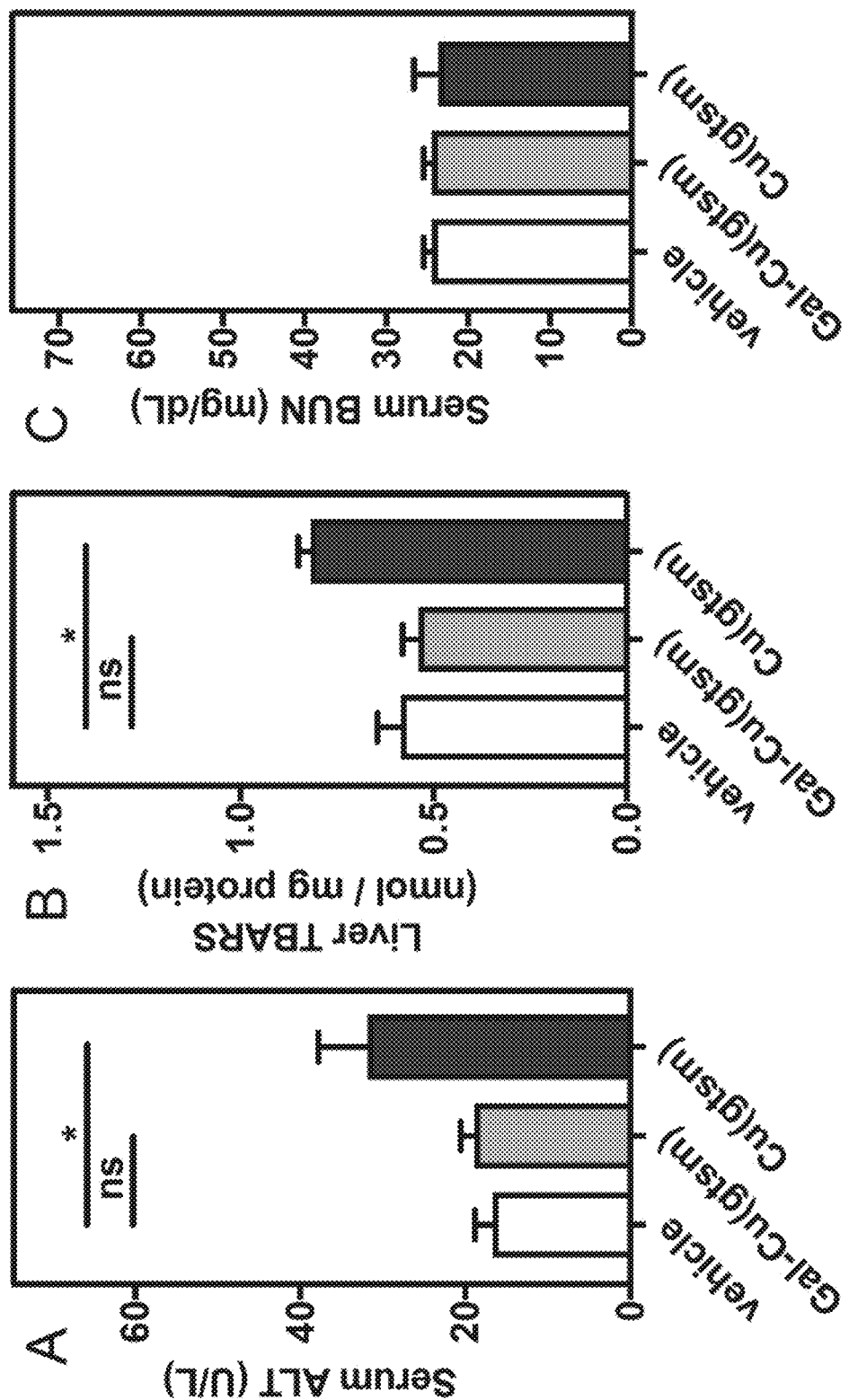
FIG. 22 shows ALT, TBARS, BUN toxicity assays from mouse liver lysate or serum isolated 24 hours after ionophore injection at 0.75 mg Cu/kg mouse. Error bars=SEM (n=5).

To further assess potential ionophore toxicity, assays were performed that assessed alanine transaminase (ALT) activity and liver thiobarbituric acid reactive substances (TBARS) on serum and liver lysate collected from mice treated with Cu(gtsm) or Gal-Cu(gtsm) at the same Cu dose after 6 hours (FIG. 20-21). It was found that virtually the same serum ALT levels for Gal-Cu(gtsm) compared to the vehicle control, but much higher serum ALT levels after Cu(gtsm) treatment (FIG. 20). Likewise, the TBARS assay, which quantifies byproducts such as malondialdehyde generated from lipid peroxidation during oxidative tissue damage, indicates there is significant oxidative stress-induced liver damage in Cu(gtsm)-treated mice compared to Gal-Cu (gtsm) or vehicle-treated mice (FIG. 21). In both assays, liver health recovers to some extent after 24 hours, but there are still significant elevations in ALT activity and TBARS levels relative to basal conditions (FIG. 22).

Figure 23:
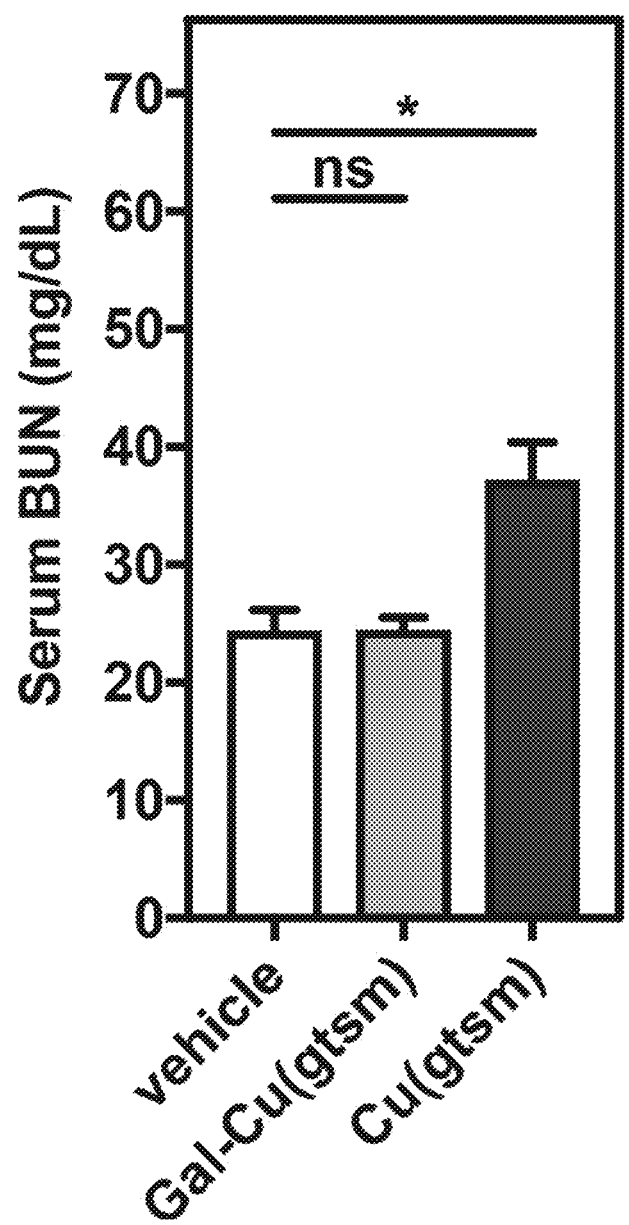
FIG. 23 shows results of a blood urea nitrogen (BUN) assay on serum after treatment with Cu(gtsm) or Gal-Cu (gtsm).

Finally, off-target toxicity was investigated using blood urea nitrogen (BUN) assays, which can be elevated under conditions of kidney damage FIG. 23 shows elevated BUN levels for Cu(gtsm), but not for Gal-Cu(gtsm), treatment, which further supports the proposal that targeted copper delivery via Gal-Cu(gtsm) does not promote damage due to off-target copper accumulation.

Figure 24:
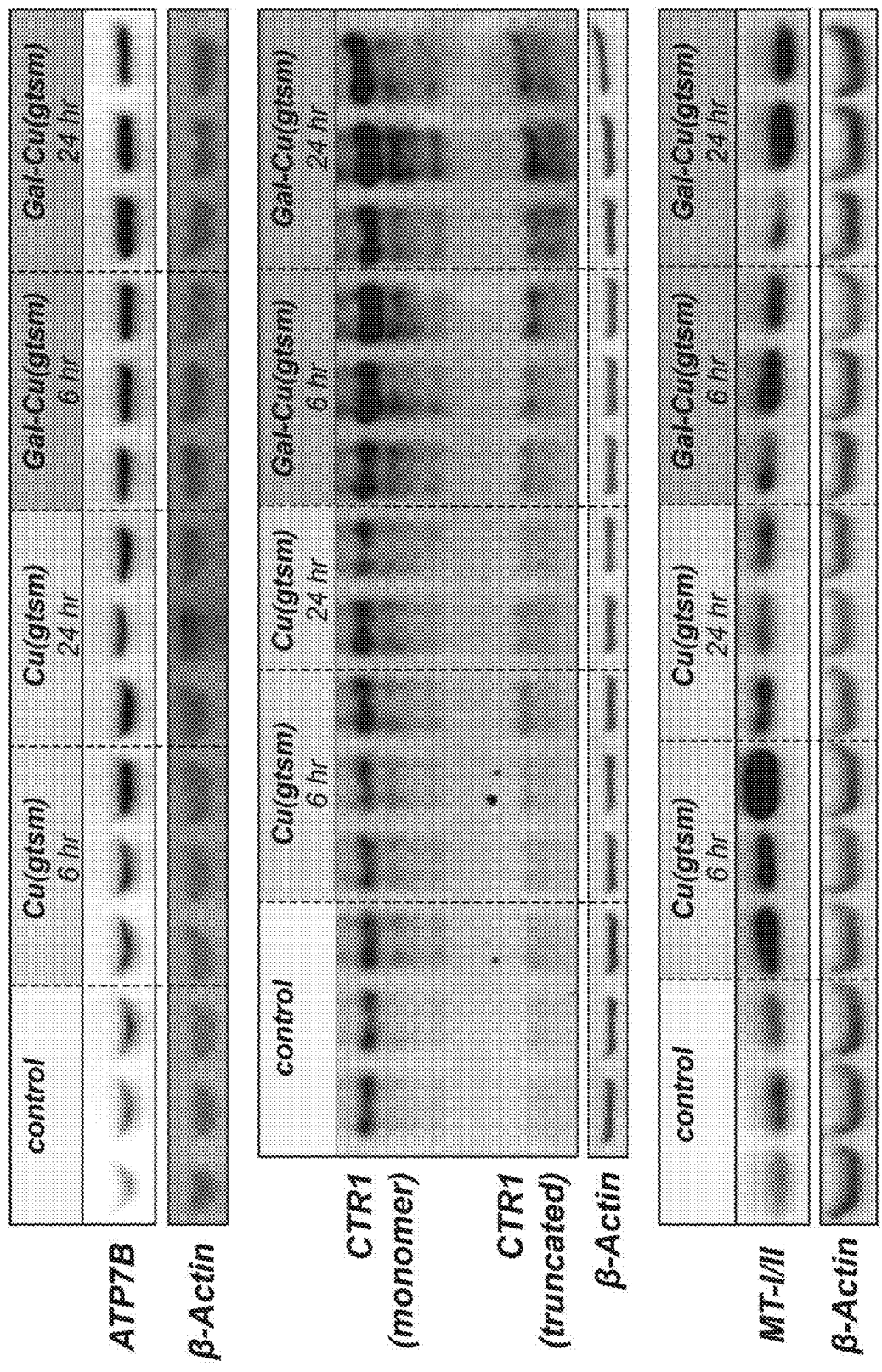
FIG. 24 shows Western Blots demonstrating how differences in copper delivery route affect copper storage and trafficking protein expression. SDS/PAGE analysis of liver extracts from mice (n=2-3). Tissues were probed for ATP7B, CTR1, and MT-I/II.

Example 5: Selective Upregulation of Copper Trafficking and Storage Proteins as a Mechanism for Minimizing Cop-per-Induced Toxicity We hypothesized that the lack of toxicity resulting from copper supplementation using Gal-Cu(gtsm) compared to its generic non-targeted Cu(gtsm) counterpart originates from their disparate mechanisms for delivery, as shown in FIGS. 1A-B. To test this prediction, Western blot analysis were performed on mouse liver lysates to investigate how these different routes of copper supplementation may affect key players in copper storage and trafficking. FIG. 24 shows SDS/PAGE analysis of liver lysates from mice treated with vehicle, Cu(gtsm), and Gal-Cu(gtsm) after 6 or 24 hours of treatment at equal protein loading. Expanded blots for all proteins are provided in FIG. 25. First, ATP7B, the major copper export protein in the liver, was blotted and it was found that ATP7B expression increased at both timepoints for Cu(gtsm) and Gal-Cu(gtsm). This observation is consistent with the known role of ATP7B to facilitate the removal of excess hepatic copper via biliary excretion (see e.g., Harada et al., Gastroenterology 2000, 118, 921; Polishchuk et al., Dev. Cell 2014, 29, 686).

Figure 25:
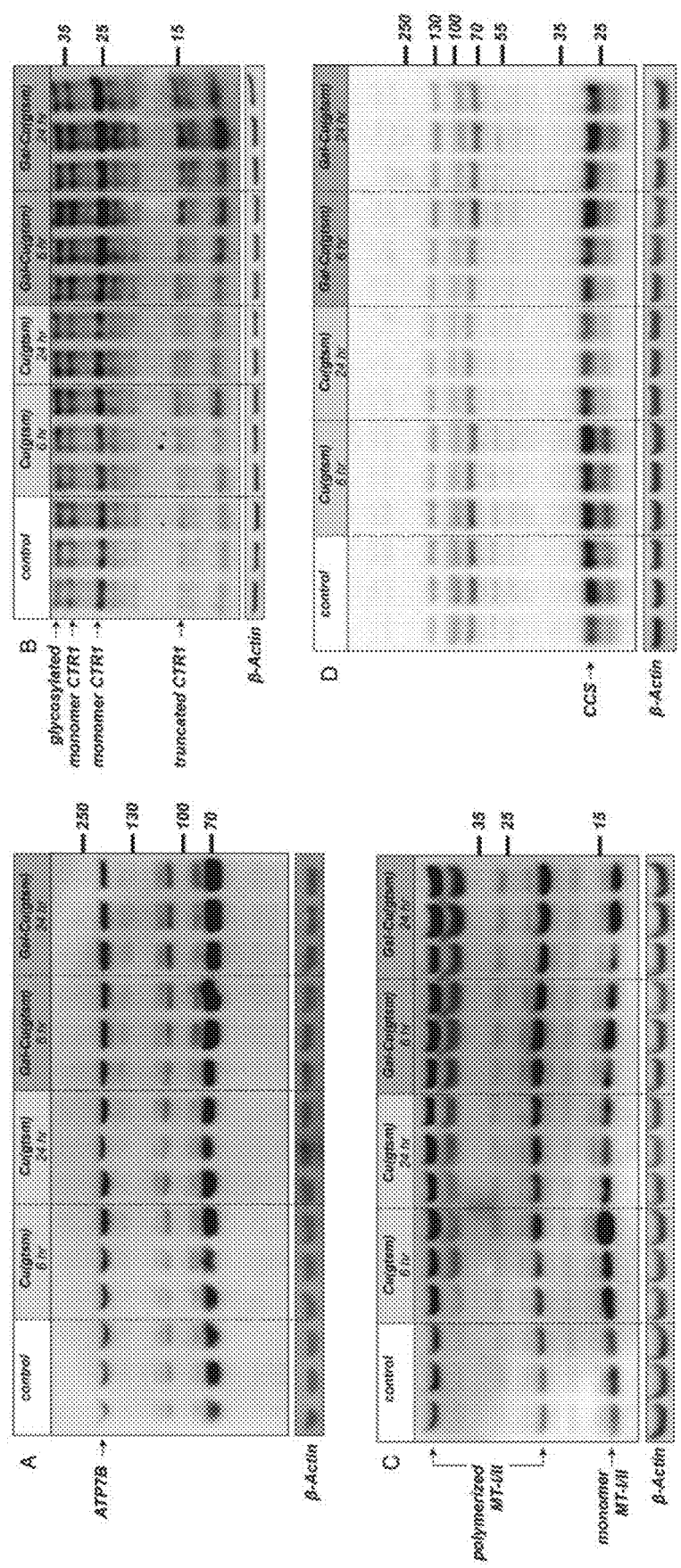
FIG. 25 shows Expanded Western blots for ATP7B (A), CTR1 (B), MT-I/II (C), and CCS (D). Arrows denote proteins of interest. Actin is used as protein loading control.

Next, the expression patterns of CTR1 were investigated. CTR1 is a copper trafficking protein that imports copper into the cell from the extracellular matrix, and transports copper from the lysosome to the cytosol in concert with CTR2. Increased expression of both the monomer and truncated forms of CTR1 was found at both 6 and 24 hour timepoints for Gal-Cu(gtsm) supplementation alone. The truncated CTR1 form may play an important role in copper transport from the lysosome to cytosol. Because increased CTR1 expression was observed only under conditions of endolysosomal Cu delivery, it was hypothesized that CTR1 plays a role in copper transport from the lysosome to cytosol. Finally, metallothioneins (MTs) are key metal storage proteins in the cytosol. MT-I/MT-II expression increases dramatically upon Cu(gtsm) and Gal-Cu(gtsm) treatment after 6 hours and 24 hours. Blots for the copper chaperone for superoxide dismutase (CCS) did not demonstrate any clear differences between treatment conditions (FIG. 25).

Example 6: Gal-Cu(gtsm) Ionophore is a Promising Candidate for Treating Non-Alcoholic Fatty Liver Disease (NAFLD)

The potential of Gal-Cu(gtsm) in the treatment of non-alcoholic fatty liver disease (NFALD) was assessed in a mouse model. Mice were subjected to a high fat diet. It was observed that mice subjected to a high fat diet and treated with Gal-Cu(gtsm) demonstrated significantly reduced liver steatosis and fattiness as compared to mice treated a high fat diet in the absence of treatment with Gal-Cu(gtsm).

Figure 27A:
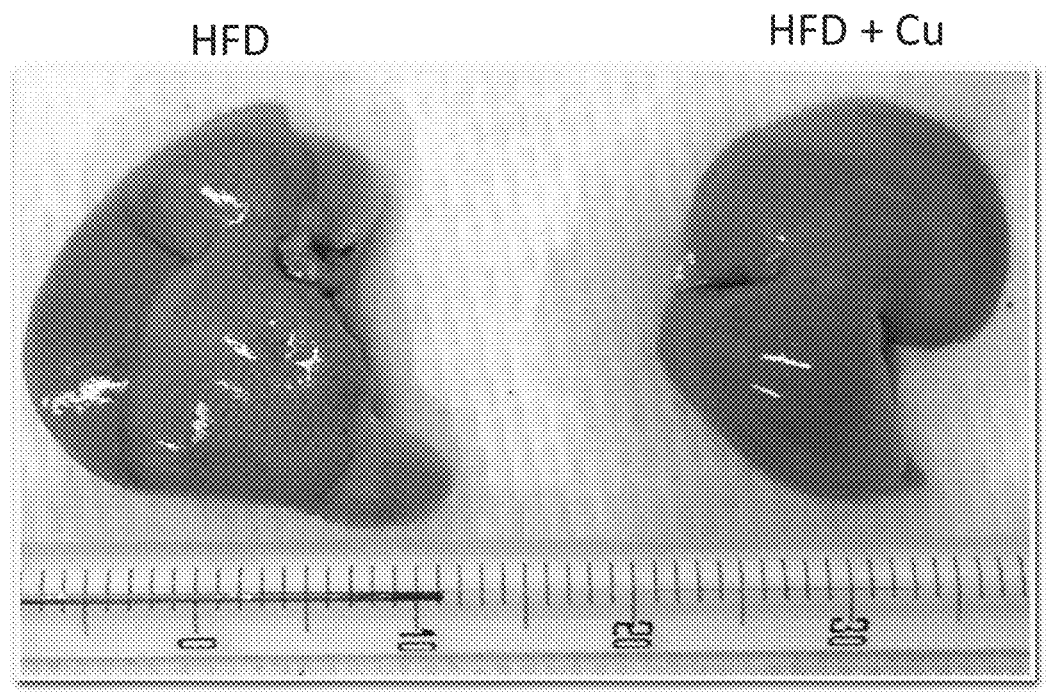
FIG. 27A shows the results of treating representative liver tissue in a mouse model for non-alcoholic fatty liver disease. Mice subjected to a high fat diet (HFD) and treated with Gal-Cu(gtsm) (HFD+Cu) exhibited reduced liver fattiness as compared to a control sample (HFD).

It was observed that targeted delivery of Gal-Cu(gtsm) reduced NAFLD symptoms. Reduced liver fattiness was observed in HFD+Cu mice, as shown in FIG. 27A and FIG. 27D. FIG. 27A shows the results of treating representative liver tissue in a mouse model for non-alcoholic fatty liver disease. Mice subjected to a high fat diet (HFD) and treated with Gal-Cu(gtsm) (also referred to herein as HFD+Cu mice) exhibited significant reduced liver fattiness as compared to a control sample (HFD). FIG. 27D shows representative liver tissue slices from H&E staining in a mouse model for non-alcoholic fatty liver disease. Fewer lipid droplets (dark droplets) were observed in mice subjected to a HFD upon Cu(gtsm) treatment (HFD+Cu).

Figure 27B:
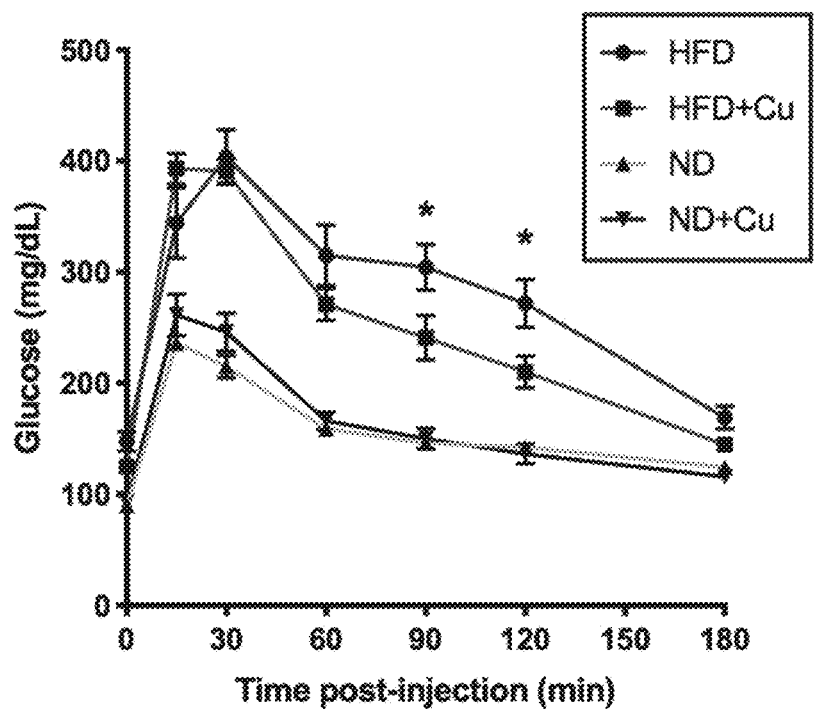
FIG. 27B shows the results of a glucose tolerance test in a mouse model for non-alcoholic fatty liver disease. Mice were subjected to a high fat diet (HFD) and treated with Gal-Cu(gtsm) (HFD+Cu). Mice subjected to a HFD and Gal-Cu(gtsm) treatment exhibited improved metabolism, as compared to mice subjected to a HFD in the absence of treatment.

It was observed that targeted delivery of Gal-Cu(gtsm) improved metabolism in HFD+Cu mice, as shown in FIG. 27B. FIG. 27B shows the results of a glucose tolerance test in a mouse model for non-alcoholic fatty liver disease. Mice were subjected to a high fat diet (HFD) and treated with Gal-Cu(gtsm) (HFD+Cu). Mice subjected to a HFD and Gal-Cu(gtsm) treatment exhibited improved metabolism, as compared to mice subjected to a HFD in the absence of treatment.

Figure 27C:
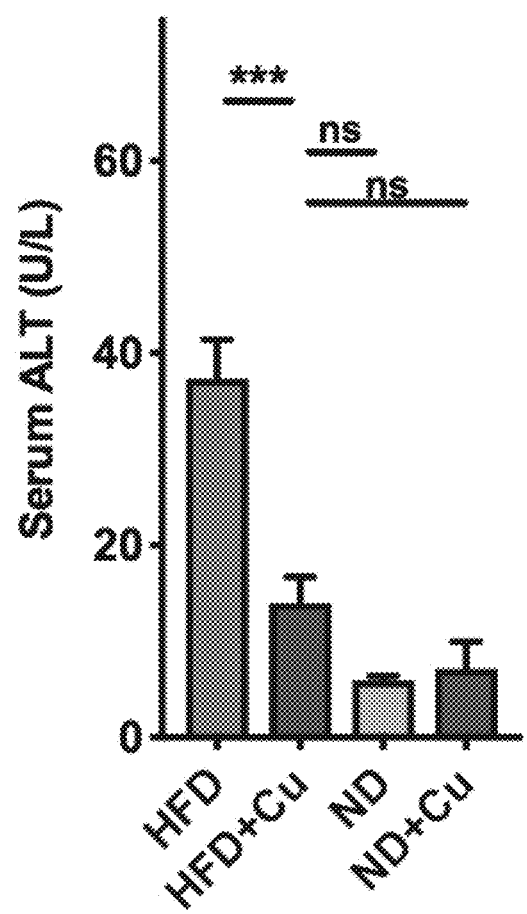
FIG. 27C shows the results of a serum ALT assay in a mouse model for non-alcoholic fatty liver disease. Mice were subjected to a high fat diet (HFD) and treated with Gal-Cu(gtsm). Mice subjected to a HFD and Gal-Cu(gtsm) treatment exhibited rescued liver health, as compared to mice feed a HFD in the absence of treatment.
Figure 27D:
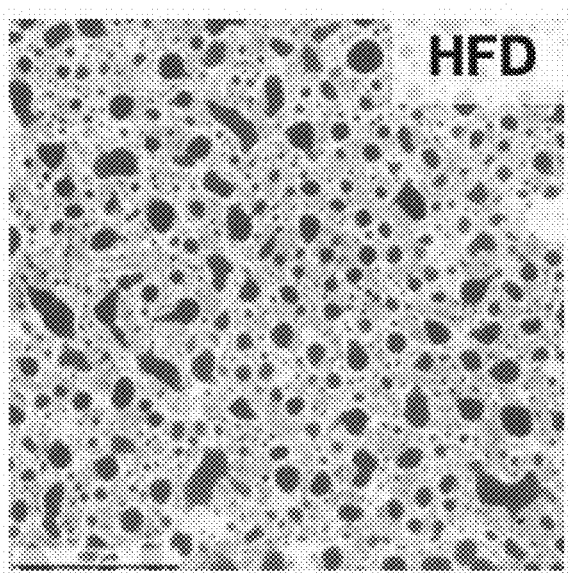
FIG. 27D shows representative liver tissue slices from H&E staining in a mouse model for non-alcoholic fatty liver disease. Fewer lipid droplets (dark droplets) were observed in mice subjected to a HFD upon Cu(gtsm) treatment (HFD+Cu).
Figure 27D:
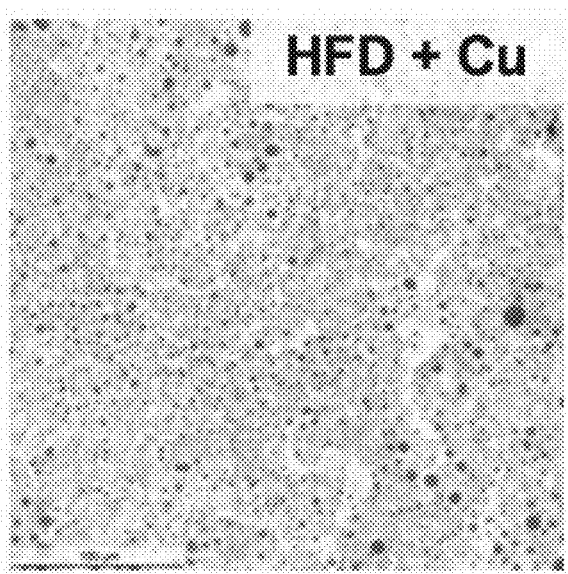
Figure 27D:
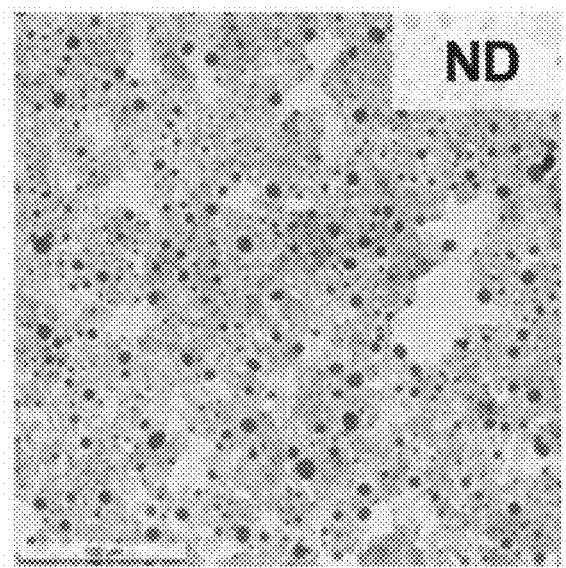
Figure 27D:
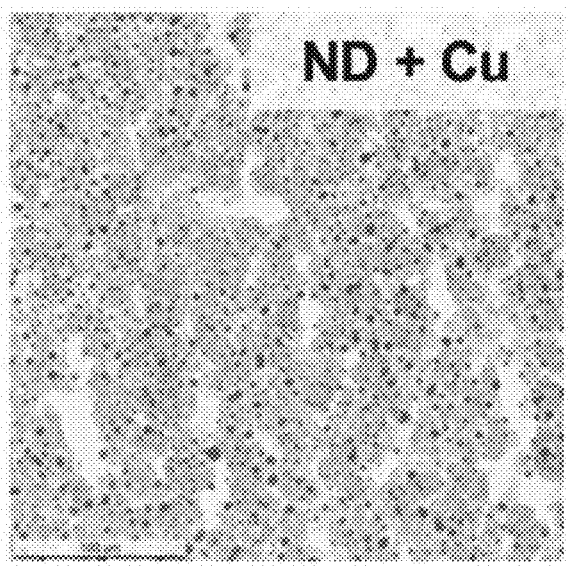

It was observed that targeted delivery of Gal-Cu(gtsm) rescued liver health in HFD+Cu mice, as shown in FIG. 27C. FIG. 27C shows the results of a serum ALT assay in a mouse model for non-alcoholic fatty liver disease. Mice were subjected to a high fat diet (HFD) and treated with Gal-Cu(gtsm). Mice subjected to a HFD and Gal-Cu(gtsm) treatment exhibited rescued liver health, as compared to mice feed a HFD in the absence of treatment.

Figure 28A:
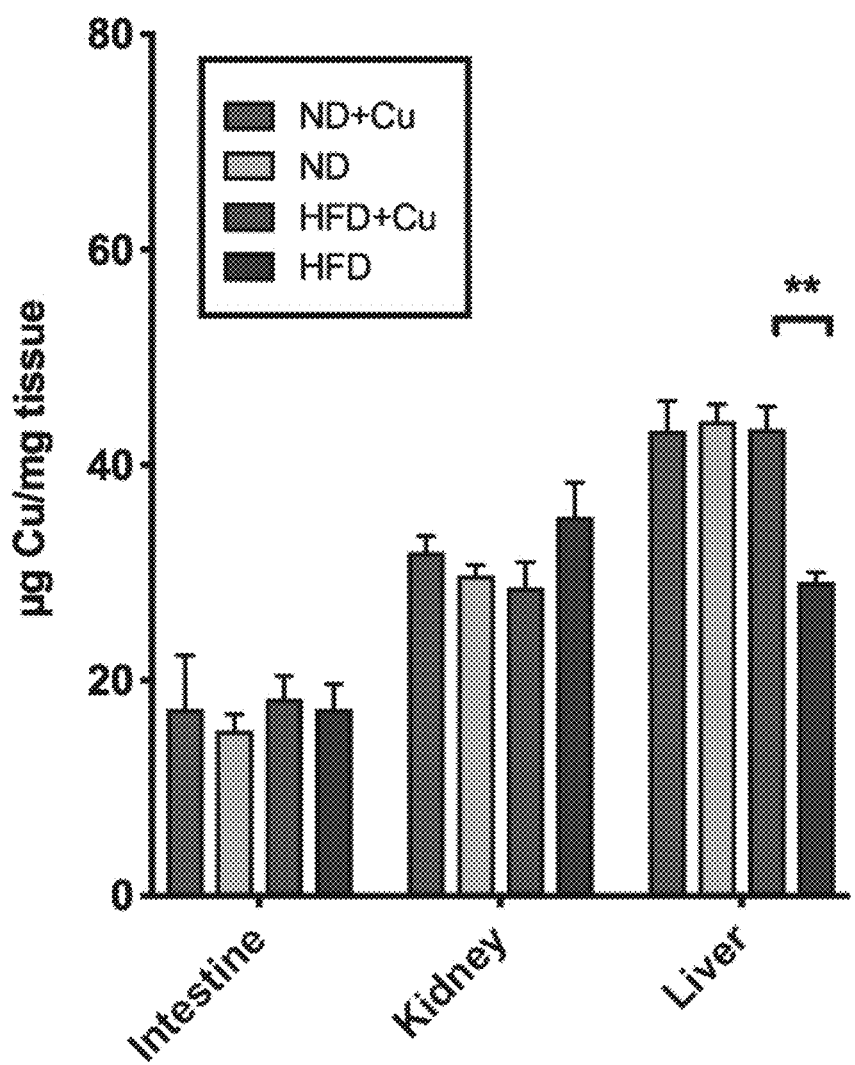
FIG. 28A shows ICP-MS analysis of tissue copper content in a mouse model for non-alcoholic fatty liver disease. Restored copper homeostasis was observed in mice feed a HFD following Gal-Cu(gtsm) treatment (HFD+Cu).
Figure 28B:
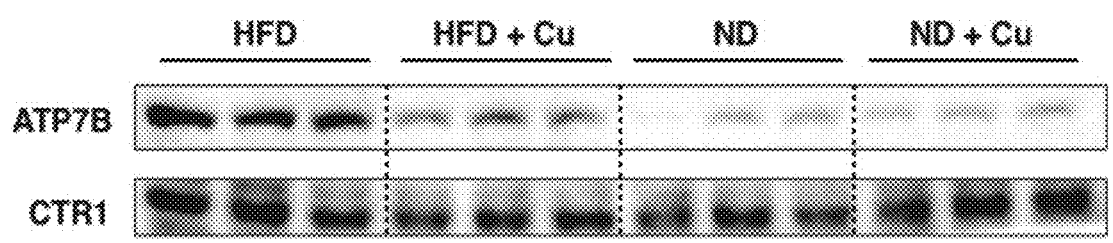
FIG. 28B shows Western Blots demonstrating reduced expression of ATP7B Cu export protein in mice subjected to a high fat diet (HFD) and treated with Gal-Cu(gtsm).
Figure 28C:
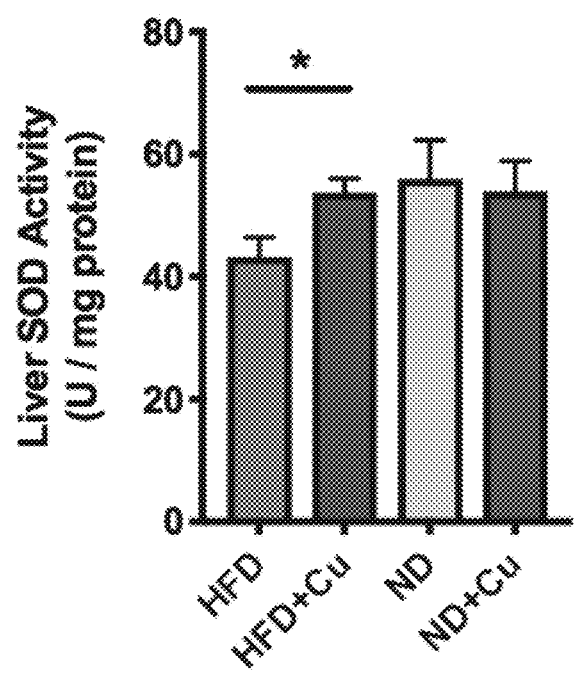
FIG. 28C shows the results of SOD assay in a mouse model for non-alcoholic fatty liver disease. Mice subjected to HFD and treated with Gal-Cu(gtsm) (HFD+Cu) exhibited improved anti-oxidant activity, as compared to mice subjected to a HFD in the absence of treatment (HFD).

It was also observed that targeted delivery of Gal-Cu(gtsm) restores copper homeostasis in NAFLD, as shown in FIGS. 28A-28C. FIG. 28A shows ICP-MS analysis of tissue copper content in a mouse model for non-alcoholic fatty liver disease. Restored copper homeostasis was observed in mice feed a HFD following Gal-Cu(gtsm) treatment (HFD+Cu). FIG. 28B shows Western Blots demonstrating reduced expression of ATP7B Cu export protein in mice subjected to a high fat diet (HFD) and treated with Gal-Cu(gtsm). FIG. 28C shows the results of SOD assay in a mouse model for non-alcoholic fatty liver disease. Mice subjected to HFD and treated with Gal-Cu(gtsm) (HFD+Cu) exhibited improved anti-oxidant activity, as compared to mice subjected to a HFD in the absence of treatment (HFD).

In summary, these results demonstrate that an exemplary subject ionophore is a promising candidate for the treatment of NAFLD.

Experimental Details

General Synthetic and Characterization Methods.

Reactions using air- or moisture-sensitive reagents were conducted in flame-dried glassware under an inert atmosphere of $N_2$. When dry solvent was required, solvent was passed over activated alumina prior to use. All commercially purchased chemicals were used as received without further purification. 4,4-dimethyl-3-thiosemicarbazide was purchased from TCI America. All other chemicals and solvents purchased from Sigma Aldrich. Cu(gtsm), CCL-1, HO-TEG-$N_3$, oxazoline 5,[70] were synthesized according to previously reported procedures (see e.g., Dearling et al., J. Biol. Inorg. Chem. 2002, 7, 249; Heffern et al., J. Proc. Natl. Acad. Sci. 2016, 113, 14219; Brun et al., J. Am. Chem. Soc. 2012, 134, 7676; Wang et al., Chem. Commun. 2011, 47, 11240). Silica gel P60 (SiliCycle) was used for column chromatography and SiliCycle 60 F254 silica gel (pre-coated sheets, 0.25 mm thick) were used for analytical thin layer chromatography. 1H and 13C NMR spectra were collected at 298 K in deuterated solvents from Cambridge Isotope Laboratories (Cambridge, Mass.) at 25° C. on Bruker AV-300, AVQ-400, AVB-400, AV-500, DRX-500, or AV-600 instruments at the College of Chemistry NMR Facility at the University of California, Berkeley. Low-resolution electrospray mass spectral analyses were performed using a LC-MS (Advion Expression-L Compact MS, ESI source). High-resolution mass spectral analyses (ESI-MS) were carried out at the College of Chemistry Mass Spectrometry Facility at the University of California, Berkeley.

Cell Culture Procedures.

Cells were maintained by the UC Berkeley Tissue Culture Facility. HEK 293T and HepG2 cells were maintained as a monolayer in exponential growth at 37° C. in a 5% CO2 atmosphere. HEK 293T cells were maintained in Dulbecco's Modified Eagle Medium (DMEM, Gibco) supplemented with 10% fetal bovine serum (FBS, Hyclone), and glutamax (Gibco). HepG2 cells were maintained in low glucose DMEM with L-glutamine and sodium pyruvate (Gibco). One day before ionophore treatment, cells were passaged and plated in DMEM with glutamax supplemented with 10% FBS on either poly D-lysine-coated (HEK 293T) or gelatin-coated (HepG2) sterile 6-well Corning polystyrene plates. Cells were grown to 60 to 80% confluency prior to ionophore treatment.

Cellular Ionophore Treatment and ICP-MS Assays.

Cells were washed twice with serum-free DMEM. 2 mM stock solutions of Cu(gtsm) or Gal-Cu(gtsm) were diluted in serum-free DMEM to a final ionophore concentration of 4 µM. 2 mL of vehicle (0.2% DMSO in DMEM), 4 µM Cu(gtsm), or 4 µM Gal-Cu(gtsm) were then added to the 6-well plates and incubated for three hours. For the galactose competition experiment, cells were washed twice with serum-free DMEM, then incubated with 2 mL serum-free DMEM either with or without 1 M D-galactose (Sigma Aldrich) for 15 minutes. 4 µL of DMSO, 2 mM Cu(gtsm), or 10 mM Gal-Cu(gtsm) was diluted with 300 µL of cell media, which was then mixed back into each well. Cells were then incubated for one hour. Cells were then rinsed twice with ice-cold EDTA (1 mM in 50 mM HEPES buffer, pH=7.4) to remove cell surface-bound copper and rinsed twice with ice-cold 50 mM HEPES buffer (pH=7.4), followed by the addition of 215 μL concentrated nitric acid (BDH Aristar Ultra). The plates were sealed with Parafilm and incubated on a shaker overnight. Samples (150 μL) were further diluted in 2 mL 2% nitric acid (made freshly from concentrated nitric acid and Milli-Q water) in 15 mL tubes (Sarstedt) and analyzed on a Thermo Fisher iCAP Qc ICP mass spectrometer in kinetic energy discrimination (KED) mode against a standard curve of known copper and phosphorus concentrations (CMS-5, Inorganic Ventures), with Ga (20 μg/L, Inorganic Ventures) as an internal standard. Each experiment was carried out twice and each condition was repeated in at least triplicate.

Animals.

FVB-luc+ (FVB-Tg (CAG-luc,-GFP)L2G85Chco/J) mice were obtained from our in-house breeding colony. Mice were group housed on a 12:12 hour light-dark cycle at 22° C. with free access to food and water. All animal studies were approved by and performed according to the guidelines of the Animal Care and Use Committee of the University of California, Berkeley.

General Animal Imaging Methods and Data Analysis.

A Xenogen IVIS Spectrum instrument (Caliper Life Sciences) was used for bioluminescence imaging in all animal experiments, and image analysis was performed using the Living Image software. The total photon flux for each animal was determined by drawing a region of interest around the liver and integrating photon flux over the total imaging period (area under the curve). We selected our liver region of interest based on comparing the bioluminescence data in vivo and ex vivo, as described in our previous studies with the CCL-1 probe.[27] The same region of interest around the liver was applied to analyzing both the CCL-1 and D-Luc data. The data plotted in FIG. 8A represents the ratio of CCL-1 integrated photon flux to basal D-luc integrated photon flux. Mice were anesthetized prior to injection and during imaging via inhalation of isoflurane. Isoflurane was purchased from Phoenix Pharmaceuticals, Inc. DMSO was purchased from Sigma-Aldrich, Dulbecco's phosphate buffered saline was purchased from Gibco, and medical-grade oxygen was purchased from Praxair.

In Vivo Imaging with CCL-1.

FVB-luc+ mice were given intraperitoneal (i.p.) injections of vehicle (50 μL 1:1 DMSO:DPBS), 3.46 mg/kg Cu(gtsm), or 7.26 mg/kg Gal-Cu(gtsm) under anesthesia with isoflurane. The ionophore concentrations were chosen to give an equivalent copper dose of 0.75 mg Cu/kg mouse at 0.6 mg Cu/mL vehicle. Six hours later, the same mice were anesthetized and subjected to scapular subcutaneous (s.c.) injection of CCL-1 (0.1 μmol in 50 μL DMSO/150 μL DPBS) or D-luciferin (0.1 μmol in 50 μL DMSO/150 DPBS). Five minutes after s.c. injection, mice were transferred to a Xenogen IVIS Spectrum and imaged for 40 min under 2% isoflurane anesthesia to characterize ionophoretreated liver signal response.

Tissue Harvesting and Serum Isolation.

FVB-luc+ mice were heavily anesthetized and blood was collected via cardiac puncture. Mice were immediately euthanized by cervical dislocation. Tissues were harvested, rinsed twice with DPBS, snap-frozen under liquid nitrogen, and placed on dry ice in cryotubes and stored at −80° C. until analysis. Serum was isolated by allowing blood samples to coagulate for 1 hour at room temperature, centrifuging at 1,500 g for 15 minutes at 4° C., then collecting the serum supernatant. Samples were aliquoted, snap-frozen, and stored at −80° C. until analysis.

Tissue Copper Analysis with ICP-MS.

20-100 mg portions of the harvested tissues were digested in concentrated nitric acid (100 mg tissue/mL $HNO_3$, BDH Aristar Ultra) at 95° C. for 2 h in 1.5 mL tubes (Sarstedt) with small holes poked in the caps with an 18G needle. After overnight incubation at room temperature, samples were diluted into freshly prepared 2% nitric acid and doped with a gallium internal standard (Inorganic Ventures, diluted from 1 ppm in 2% nitric acid to a 20 ppb final concentration). The copper content was determined by measuring $^{63}Cu$ using a Thermo Fisher iCAP-Qc ICP-MS in Kinetic Energy Discrimination (KED) mode. Measurements were normalized to a standard curve of known copper concentrations doped with 20 ppb Ga. The standard curve was diluted from CMS-5 (Inorganic Ventures).

Liver Tissue Histology.

FVB-luc+ mice were injected i.p. with vehicle (50 μL 1:1 DMSO:DPBS), Cu(gtsm), or Gal-Cu(gtsm) at a 0.75 mg Cu/kg mouse dose. After six hours, mice were euthanized with $CO_2$ asphyxiation followed by cervical dislocation and liver tissue was extracted. Liver sections were fixed in a 10% formalin in PBS solution and sent to Histowiz Inc. (Brooklyn, N.Y.) for further processing and hematoxylin & eosin staining.

Liver Tissue Lysis.

Frozen mouse livers were minced into 50 mg samples on dry ice and homogenized in ice-cold RIPA buffer (25 mM Tris.HCl pH 7.6, 150 mM NaCl, 1% NP-40, 1% sodium deoxycholate, 0.1% SDS) containing protease inhibitor cocktail with EDTA (Roche) at 100 mg/mL using a handheld mechanical homogenizer. Homogenates were incubated on ice for 30 min and centrifuged at 12,000×g for 20 min at 4° C. The soluble protein lysates were collected from underneath the upper lipid layer with a pipette and transferred to new tubes. Protein concentration was determined using a detergent-compatible Bradford Assay (Pierce).

Toxicity Assays of Liver Lysate and Serum.

Liver lysate (TBARS Assay via TCA Method, Cayman Chemical) and serum (BUN Assay, Invitrogen; ALT Assay, Cayman Chemical) samples were processed according to manufacturer instructions; sample concentration was selected based on initial dilution screening to fall within linear range of the standard curve. All samples were analyzed in triplicate.

Western Blot Analysis.

Protein lysates were denatured in NuPAGE lithium dodecyl sulfate sample buffer (Invitrogen) containing 10% v/v β-mercaptoethanol as a reducing agent. The samples (20 μg for CCS, CTR1, ATP7B; 50 μg for MT) were resolved by SDS-PAGE using 15-well or 17-well NuPAGE 4-12% Bis-Tris gels (Invitrogen) with MES SDS running buffer (Invitrogen) with 10 μL of loading sample. Proteins were transferred to a polyvinylidene difluoride membrane (BioRad, Munich, Germany) with the use of the Trans-Blot Turbo transfer system (BioRad, Munich, Germany)). The membranes were blocked in 5% non-fat dry milk in TBST buffer (10 mM Tris, pH 7.5, 100 mM NaCl, 0.1% Tween-20) for 1 hour at room temperature. After blocking, the membranes were incubated at 4° C. overnight with primary antibodies diluted with TBST buffer containing 5% bovine serum albumin (BSA). The anti-ATP7B (NB100-360, Novus Biologics) and anti-metallothionein (sc-11377, Santa Cruz Biotechnology) were used at 1:250 dilution. The anti-CTR1 antibody (13086, Cell Signaling Technology) was used at 1:1000 dilution. The anti-CCS (sc-20141, Santa Cruz Biotechnology) was used at 1:500 dilution. The membranes were washed 3 times for 5 minutes in TBST and incubated for 1 hour at room temperature with horseradish peroxidase (HRP)-conjugated anti-rabbit IgG secondary antibody (sc-2004, Santa Cruz Biotechnology) at a 1:2000 dilution in TBST containing 5% BSA. The membranes were washed 5 times for 5 minutes in TBST, then visualized using enhanced chemiluminescence (Western Lighting Plus for visualizing CCS and ATP7B, Perkin Elmer; Western Clarity Max for visualizing CTR1 and MT, Bio-Rad) recorded on a BioRad GelDoc imaging station. β-actin was probed to determine equal loading using anti-β-actin (sc-69879, Santa Cruz Biotechnology) and AlexaFluor 647-conjugated anti-mouse IgG (A31571, Molecular Probes) antibodies at 1:5000 and 1:2500 dilutions, respectively, with visualization using fluorescence recorded on a BioRad GelDoc imaging station.

Log P Measurements.

Log P measurements were performed with The shake-flask method based on compound partitioning between n-octanol and PBS (pH=7.4) layers. Octanol (saturated with PBS) and PBS (saturated with octanol) was obtained by vigorous mixing for one hour followed by layer separation in a separatory funnel over 24 hours. For Gal-Cu(gtsm): 500 μL of standard solutions were made with 100, 50, 20, 10, and 5 μM of Gal-Cu(gtsm) dissolved in PBS-saturated octanol. 50 mM stock solution in DMSO was diluted to 100 μM final concentration with 490/10, 480/20, and 460/40 μL of saturated octanol/PBS. For Cu(gtsm): 500 μL of standard solutions were made with 100, 50, 20, 10, and 5 μM of Gal-Cu(gtsm) dissolved in octanol-saturated PBS. 50 mM stock solution in DMSO was diluted to 100 μM final concentration with 10/490, 475/25, and 50/450 μL of saturated octanol/PBS. All standards and samples were vortexed vigorously in 1.7 mL microcentrifuge tubes for 60 seconds, then spun down at 12,000 g for 2 mins in a microcentrifuge. 200 μL of each standard and sample were added to a clear 96-well plate, and the blank-subtracted absorbance at 470 nm was read in a Synergy M2 plate reader. All standards and samples were measured in duplicate. Log P values were calculated from the subsequent partition coefficients and averaged across the three partition conditions to obtain the final log P value. Error is reported as standard deviation.

Dynamic Light Scattering Measurements.

Figure 26A:
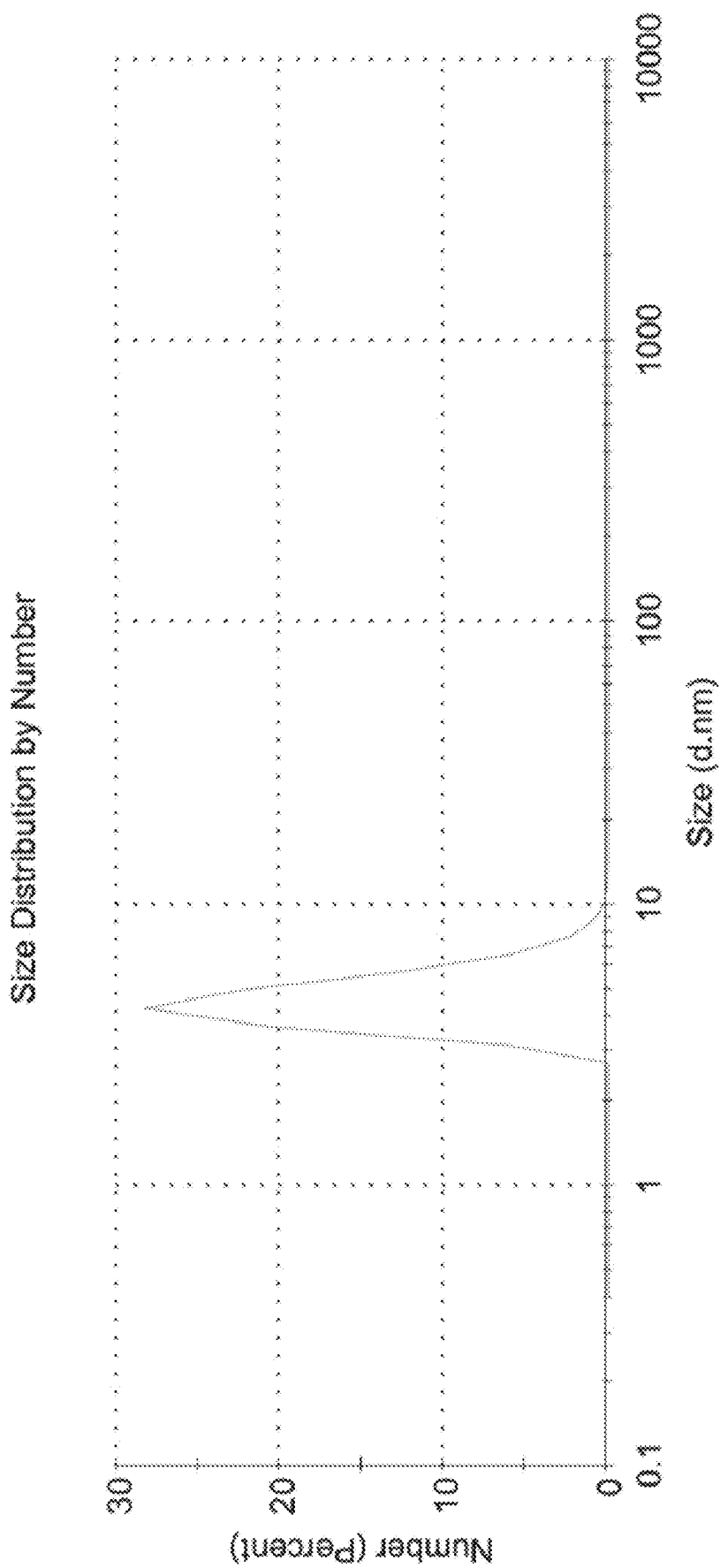
FIG. 26A shows number-weighted size distribution plot for one replicate measurement of Gal-Cu(gtsm) at 1 mM in PBS (pH=7.4) measured with dynamic light scattering.
Figure 26B:
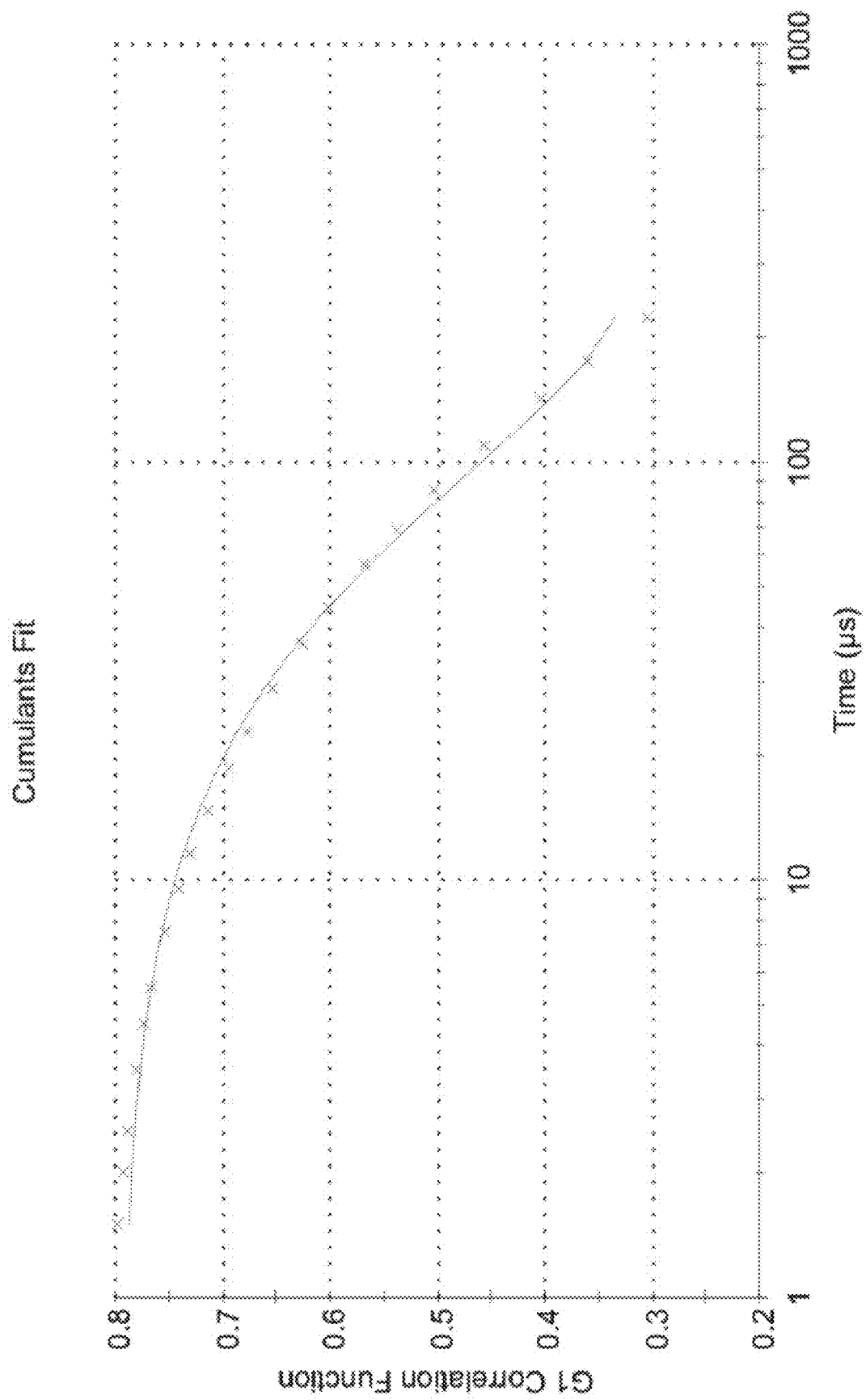
FIG. 26B shows cumulants fit plot for one replicate measurement of Gal-Cu(gtsm) at 1 mM in PBS (pH=7.4) measured with dynamic light scattering.

To assess colloidal aggregate formation, Gal-Cu(gtsm) was dissolved in PBS (pH 7.4) to a final concentration of 1 mM. The hydrodynamic diameter ($D_H$) of the formed colloidal particles were determined by dynamic light scattering (DLS) obtained on a Zetasizer® Nano Series (Malvern Instruments, UK) and reported as the number-weighted mean. Samples were filtered with a 0.2 μm syringe filter and measured with a disposable ZEN0040 cuvette. Peaks of varying sizes were found, indicating a polydisperse formation of Gal-Cu(gtsm) aggregates. Measurements were taken in triplicate. Error is reported as the standard deviation from three separate replicates. Sample data shown in FIG. 26A-B. No peaks were observed for Cu(gtsm) at 0.1 mM.

UV-vis Absorption Studies.

All spectroscopic measurements were performed in 20 mM PBS, pH 7.4 unless otherwise indicated. Absorption spectra were acquired on a Varian Cary 50 spectrophotometer.

Cell Viability Studies.

Flow cytometry experiments were performed with BD LSR Fortessa Cell Analyzer in the College of Chemistry at UC Berkeley. Gains were set to include live cells based on viability experiments using propidium iodide, with dead cells via 0.1% saponin treatment as a negative control. The standard PE-A (570 nm longpass, 586/15 nm bandpass) was used. For each biological replicate, three technical replicates of 5,000 (HepG2) or 10,000 cells (HEK 293T) were counted. Flow cytometry data was processed using FlowJo (FlowJo, LLC).

HEK 293T cells were plated in 6-well plates at 60-80% confluency. After ionophore treatment at the given concentration for three hours, cells were washed with DMEM and incubated with 3 μM propidium iodide in PBS for 15 minutes, then rinsed in PBS. HEK 293T cells were mechanically removed via pipetting off the plate with 1 mL PBS and filtered through a 35 μm nylon mesh into 5 mL culture tubes for analysis. HepG2 cells were plated in 12-well plates at 60-80% confluency. After ionophore treatment at the given concentration for three hours in low glucose DMEM, cells were rinsed with low glucose DMEM, treated with 150 μL trypsin (0.25%) for 5 minutes, inactivated with 450 μL 10% FBS in DMEM, transferred to 1.7 mL microcentrifuge tubes, spun down at 2,000 g for 5 mins Cells were re-suspended in 500 μL of 3 μM propidium iodide and incubated at 37° C. for 15 mins, spun down at 2,000 g for 5 minutes, then re-suspended in PBS for flow cytometry analysis.

Confocal Fluorescence Imaging Experiments.

Confocal fluorescence images were acquired with a Zeiss LSM710 laser-scanning microscope with a 20× objective lens. Excitation at 543 nm for CF4 was carried out with appropriate lasers, and emission was acquired from 550 to 650 nm. HepG2 cells were plated between 50-80% confluency in 8-well glass chamber slides with gelatin coating. Cells were incubated with either vehicle, Cu(gtsm), or Gal-Cu(gtsm) for 3 hours in low glucose DMEM. The media was then aspirated and replaced with CF4 or Ctrl-CF4-S2 (2 μM freshly diluted from a 1 mM stock solution) in DPBS with calcium and magnesium, then incubated at 37° C. for 30 minutes. The buffer was then replaced with fresh DPBS (+Ca, +Mg) for imaging. Image analysis and quantification was performed using ImageJ (National Institutes of Health). Mean fluorescence intensity was analyzed with a minimum threshold of 20 pixels and maximum threshold of 255 pixels.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein.

What is claimed is:

1. An ionophore compound of the formula (I):

(T-L)$_n$-(Z-M)    (I)

wherein:

T is a targeting moiety selected from the group consisting of a saccharide, a polysaccharide, a multivalent saccharide, an amino sugar, a peptide, a small molecule drug, a small molecule drug fragment and a phosphonium cation;

L is a linker;

M is a metal ion;

Z is an ionophore capable of complexing M; and n is an integer from 1 to 20.

2. The ionophore compound of claim 1, wherein T is a liver-targeting moiety, a mitochondria-targeting moiety, a nucleus-targeting moiety, an adipose-targeting moiety, a heart-targeting moiety or a brain targeting moiety.

3. The ionophore compound of claim 1, wherein T is selected from galactose, a galactose derivative, a multivalent galactose conjugate, an amino sugar derivative of galactose and a multivalent amino sugar derivative of galactose.

4. The ionophore compound of claim 1, wherein Z is selected from:

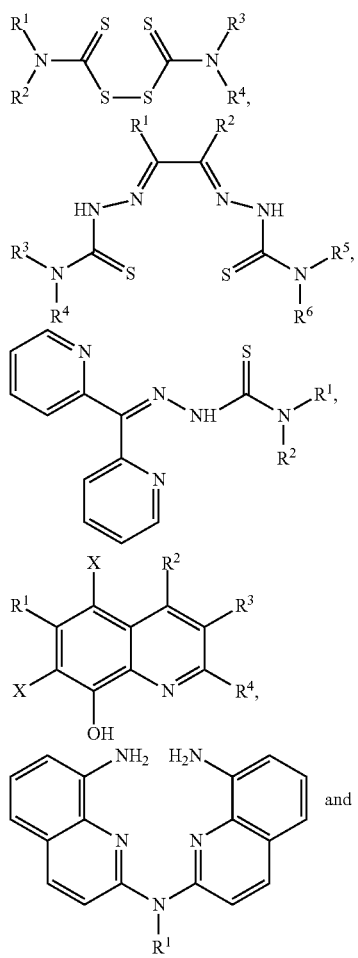

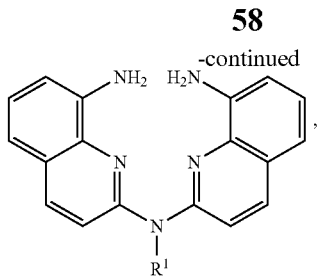

wherein:

X is a halogen; and $R^1$, $R^2$, $R^3$, $R^4$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl and substituted acyl.

5. The ionophore compound of claim 4, wherein the ionophore is:

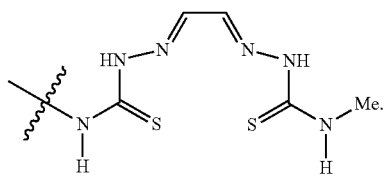

6. The ionophore compound of claim 1, wherein L is selected from a linear or branched alkyl, alkenylene, alkynylene, arylene, alkarylene, aralkylene, alkoxy, alkamine, polyethylene glycol (PEG), a modified PEG, an oligoethyleneglycol, a phosphate, a phosphonate, a boric acid, a carboxylate, a sulfate, a sulfonate, an amine, a glycerol, a sugar, an amino acid and a substituted amino acid.

7. The ionophore compound of claim 1, of the formula (II)

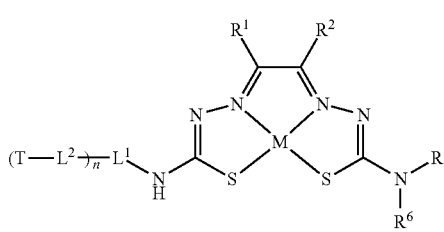

wherein:

$R^1$, $R^2$, $R^5$ and $R^6$ are each independently selected from H, alkyl, substituted alkyl, alkenyl, substituted alkenyl, alkoxy, substituted alkoxy, aryl, substituted aryl, cycloalkyl, substituted cycloalkyl, acyl, substituted acyl and -$L^1(L^2$-T$)_n$;

T is a targeting moiety;

$L^1$ is a bond or a linker;

$L^2$ are each independently a linker selected from a linear or branched alkyl, alkenylene, alkynylene, arylene, alkarylene, aralkylene, alkoxy, alkamine polyethylene glycol (PEG), a modified PEG, a oligoethyleneglycol, a phosphate, a phosphonate, a boric acid, a carboxylate, a sulfate, a sulfonate, an amine, a glycerol, a sugar, an amino acid and a substituted amino acid;

M is a metal ion; and n is an integer from 1 to 20.

8. The ionophore compound of claim 7, wherein T is selected from, a peptide comprising the sequence CKG-GRAKDC, a peptide comprising the sequence APWHLSSQYSRT, a peptide comprising the sequence TFFYGGSRGKRNNFKTEEY,

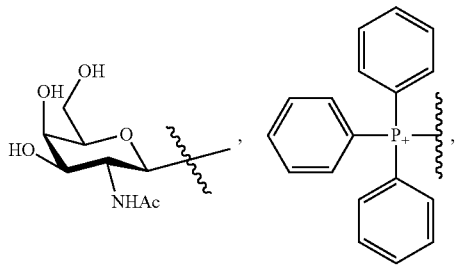

-continued

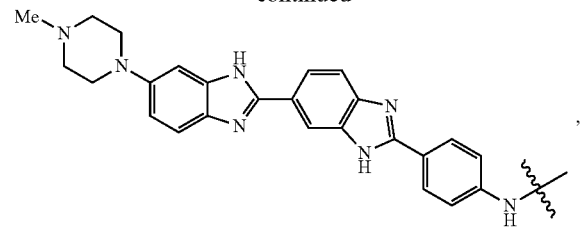

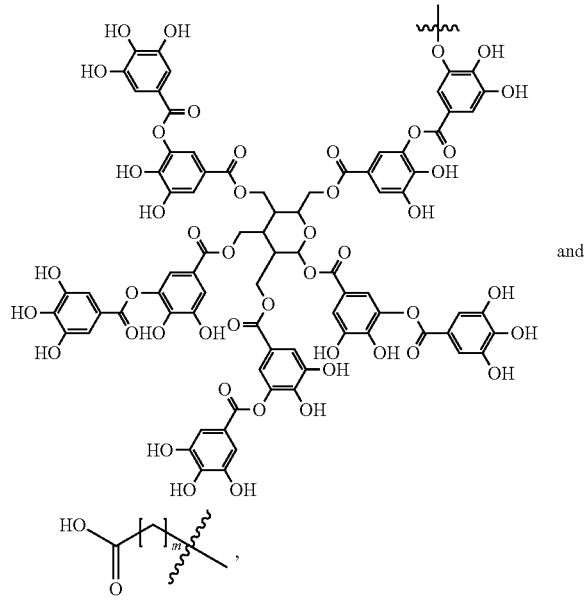

wherein m is an integer from 1 to 20.

9. The ionophore compound of claim 7, wherein each $L^2$ are independently selected from:

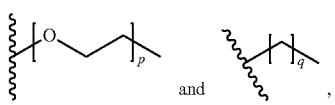

wherein p and q are each independently an integer from 1 to 20.

10. The ionophore compound of claim 1, wherein M is selected from a copper ion, an iron ion, a zinc ion, a cobalt ion and a manganese ion.

11. The ionophore compound of claim 1, having the following structure:

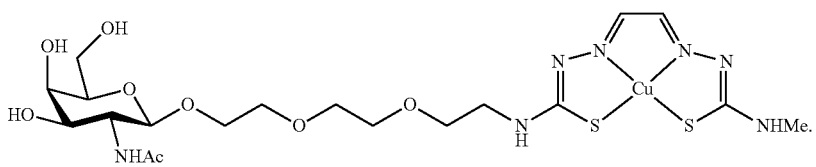

12. A method of delivering a metal intracellularly to a target cell, the method comprising:
contacting the target cell with an ionophore compound of claim 1; wherein:
M is a first ionic form ($M^1$) of the metal, wherein the ionophore has a higher affinity for $M^1$ over a second ionic form $M^2$ of the metal; and
T is a targeting moiety specific for the target cell;
to internalize the ionophore within the target cell and reduce $M^1$ to $M^2$ thereby intracellularly releasing the metal ion ($M^2$) from the ionophore.

13. The method of claim 12, wherein the cell is in vitro.

14. The method of claim 12, wherein the cell is in vivo in a human or non-human organism.

15. The method of claim 12, wherein the target cell has a reducing intracellular environment that triggers reduction of $M^1$ to $M^2$ and release of $M^2$ from the ionophore compound.

16. The method of claim 12, wherein $M^2$ is delivered to the endolysosomal pathway of the target cell by active transport via the targeting moiety.

17. A method of treating a condition associated with a metal deficiency, the method comprising:
administering to a subject in need thereof a pharmaceutical composition comprising a compound of claim 1 and a pharmaceutically acceptable excipient; and
releasing a metal ion from the ionophore compound at a targeted site in the subject to treat the subject.

18. The method of claim 17, wherein the targeted site is selected from, liver, adipose, heart and brain.

19. The method of claim 17, wherein the metal ion is copper ion.

20. The method of claim 17, wherein the condition associated with a metal deficiency is a metabolic disorder.

21. The method of claim 20, wherein the metabolic disorder is non-alcoholic fatty liver disease (NAFLD).

* * * * *

UNITED STATES PATENT AND TRADEMARK OFFICE
CERTIFICATE OF CORRECTION

| | | |
|---|---|---|
| PATENT NO. | : 11,504,394 B2 | Page 1 of 1 |
| APPLICATION NO. | : 16/594798 | |
| DATED | : November 22, 2022 | |
| INVENTOR(S) | : Christopher J. Chang et al. | |

It is certified that error appears in the above-identified patent and that said Letters Patent is hereby corrected as shown below:

In the Specification

In Column 11, Line 7, please change "-O$^-$M$^+$, -SR$^{70}$" to --- -O$^-$M$^+$, -OR$^{70}$, -SR$^{70}$ ---

Signed and Sealed this
Seventeenth Day of January, 2023

Katherine Kelly Vidal
*Director of the United States Patent and Trademark Office*